US012690798B2

(12) United States Patent
Aranda Hernandez et al.

(10) Patent No.: US 12,690,798 B2
(45) Date of Patent: Jul. 28, 2026

(54) MEDICAL DEVICE AND METHOD FOR DETECTING ARRHYTHMIA

(71) Applicant: Medtronic, Inc., Minneapolis, MN (US)

(72) Inventors: Alfonso Aranda Hernandez, Minneapolis, MN (US); Timothy A. Ebeling, Circle Pines, MN (US); Saul E. Greenhut, Denver, CO (US); Troy E. Jackson, Rogers, MN (US); Yuanzhen Liu, Minneapolis, MN (US); Irving J. Sanchez, Blaine, MN (US); James A. Vander Heyden, Delano, MN (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 642 days.

(21) Appl. No.: 18/045,135

(22) Filed: Oct. 7, 2022

(65) Prior Publication Data

US 2023/0148939 A1    May 18, 2023

Related U.S. Application Data

(60) Provisional application No. 63/278,955, filed on Nov. 12, 2021.

(51) Int. Cl.
*A61N 1/36*      (2006.01)
*A61B 5/363*     (2021.01)
(Continued)

(52) U.S. Cl.
CPC ............ *A61B 5/363* (2021.01); *A61N 1/3621* (2013.01); *A61N 1/365* (2013.01)

(58) Field of Classification Search
CPC ...... A61B 5/363; A61N 1/3621; A61N 1/365; A61N 1/3925
See application file for complete search history.

(56) References Cited

U.S. PATENT DOCUMENTS 4,940,054 A *   7/1990  Grevis ................. A61N 1/3621
                                                  607/7
6,430,435 B1    8/2002  Hsu et al.
                    (Continued)

FOREIGN PATENT DOCUMENTS

WO        2008137536 A1    11/2008

OTHER PUBLICATIONS (PCT/IB2022/059880) PCT Notification of Transmittal of the International Search Report and the Written Opinion of the International Searching Authority, Mailed Jan. 30, 2023, 12 pages.

*Primary Examiner* — Rex R Holmes

(57)        ABSTRACT

A medical device is configured to determine an amplitude metric from a cardiac signal segment sensed over a predetermined time interval and determine if the amplitude metric meets an amplitude threshold. The medical device is configured to perform a first analysis of the cardiac electrical signal segment for detecting a first arrhythmia when the amplitude metric does not meet the amplitude threshold and perform a second analysis of the cardiac electrical signal segment for detecting a second arrhythmia different than the first arrhythmia in response to the amplitude metric meeting the amplitude threshold.

30 Claims, 21 Drawing Sheets

(51) Int. Cl.
    *A61N 1/362*           (2006.01)
    *A61N 1/365*           (2006.01)

(56)           References Cited

U.S. PATENT DOCUMENTS

| | | | |
|---|---|---|---|
| 7,031,764 B2 | 4/2006 | Schwartz et al. | |
| 7,130,681 B2 | 10/2006 | Gebhardt et al. | |
| 7,248,921 B2 | 7/2007 | Palreddy et al. | |
| 7,283,865 B2 | 10/2007 | Norén | |
| 7,333,855 B2 | 2/2008 | Gunderson et al. | |
| 7,392,085 B2 | 6/2008 | Warren et al. | |
| 7,496,409 B2 | 2/2009 | Greenhut et al. | |
| 7,650,182 B2 | 1/2010 | Kim et al. | |
| 7,761,142 B2 | 7/2010 | Ghanem et al. | |
| 7,761,150 B2 | 7/2010 | Ghanem et al. | |
| 7,783,340 B2 | 8/2010 | Sanghera et al. | |
| 7,813,791 B1 | 10/2010 | Gill et al. | |
| 7,907,993 B2 | 3/2011 | Ghanem et al. | |
| 7,912,545 B2 | 3/2011 | Li et al. | |
| 7,930,020 B2 | 4/2011 | Zhang et al. | |
| 7,991,471 B2 | 8/2011 | Ghanem et al. | |
| 8,027,720 B2 | 9/2011 | Bardy et al. | |
| 8,050,751 B2 | 11/2011 | Zhang et al. | |
| 8,050,754 B2 | 11/2011 | Ostroff et al. | |
| 8,095,206 B2 | 1/2012 | Ghanem et al. | |
| 8,116,867 B2 | 2/2012 | Ostroff | |
| 8,265,749 B2 | 9/2012 | Allavatam et al. | |
| 8,478,389 B1 | 7/2013 | Brockway et al. | |
| 8,521,268 B2 | 8/2013 | Zhang et al. | |
| 8,781,585 B2 | 7/2014 | Gunderson et al. | |
| 8,825,157 B2 | 9/2014 | Warren et al. | |
| 8,909,331 B2 | 12/2014 | Sanghera et al. | |
| 8,965,530 B2 | 2/2015 | Sanghera et al. | |
| 8,983,586 B2 | 3/2015 | Zhang | |
| 9,022,962 B2 | 5/2015 | Brown | |
| 9,155,485 B2 | 10/2015 | Ostroff et al. | |
| 9,179,853 B2 | 11/2015 | Sanghera et al. | |
| 9,186,521 B2 | 11/2015 | Quan et al. | |
| 9,364,677 B2 | 6/2016 | Sanghera et al. | |
| 9,579,065 B2 | 2/2017 | Allavatam et al. | |
| 9,610,025 B2 | 4/2017 | Zhang | |
| 9,764,152 B2 | 9/2017 | Warren et al. | |
| 9,802,056 B2 | 10/2017 | Allavatam et al. | |
| 9,849,291 B2 | 12/2017 | Keefe et al. | |
| 10,136,826 B2 | 11/2018 | Sullivan et al. | |
| 10,136,860 B2 | 11/2018 | Narayan | |
| 10,252,071 B2 | 4/2019 | Cao et al. | |
| 10,299,688 B2 | 5/2019 | Brisben et al. | |
| 10,321,834 B2 | 6/2019 | Brisben et al. | |
| 10,362,948 B2 | 7/2019 | Brisben et al. | |
| 10,470,681 B2 | 11/2019 | Greenhut et al. | |
| 10,493,291 B2 | 12/2019 | Cao et al. | |
| 10,507,332 B2 | 12/2019 | Zhang et al. | |
| 10,555,684 B2 | 2/2020 | Zhang et al. | |
| 10,561,332 B2 | 2/2020 | Zhang et al. | |
| 10,675,478 B2 | 6/2020 | Marshall et al. | |
| 10,709,379 B2 | 7/2020 | Warren et al. | |
| 10,850,113 B2 | 12/2020 | Cao et al. | |
| 2014/0276160 A1 | 9/2014 | Zhang et al. | |
| 2015/0088019 A1 | 3/2015 | MacAdam et al. | |
| 2016/0106989 A1 | 4/2016 | Stadler et al. | |
| 2016/0113536 A1 | 4/2016 | Greenhut et al. | |
| 2017/0312532 A1 | 11/2017 | Zhang et al. | |
| 2017/0319862 A1* | 11/2017 | Foshee, Jr. | A61N 1/3993 |
| 2017/0354827 A1 | 12/2017 | Zhang et al. | |
| 2018/0028087 A1 | 2/2018 | Zhang et al. | |
| 2018/0177425 A1 | 6/2018 | Stadler et al. | |
| 2019/0038165 A1* | 2/2019 | Relan | A61B 5/339 |
| 2019/0117985 A1* | 4/2019 | Cao | A61N 1/365 |
| 2020/0197708 A1 | 6/2020 | Cao et al. | |
| 2021/0138243 A1 | 5/2021 | Zhang et al. | |
| 2021/0170170 A1 | 6/2021 | Mischler et al. | |

* cited by examiner

400

402 — DETERMINE MEAN RECTIFIED AMPLITUDE

404 — DETERMINE NORMALIZED MRA

406 — DETERMINE MUSCLE NOISE PULSE COUNT(S)

408 — DETERMINE MEAN PERIOD

500

600

602 — DETERMINE LOW PASS FILTERED SIGNAL

C

604 — DETERMINE GRADIENT SIGNAL

606 — GRADIENT SIGNAL MEETS ASYSTOLE CONDITION?

YES

612 — ASYSTOLE SEGMENT

NO

614 — NON-ASYSTOLE SEGMENT

616 — N ASYSTOLE SEGMENTS?

NO

YES

618 — DETECT ASYSTOLE

620 — DELIVER PACING PULSE(S)

A

<u>700</u>

702 — DETERMINE LOW PASS FILTERED SIGNAL

704 — DETERMINE GRADIENT SIGNAL

706 — DETERMINE ZERO CROSSINGS

708 — IDENTIFY WINDOWS WITH THRESHOLD NUMBER OF ZERO CROSSINGS

710 — DETERMINE GRADIENT SIGNAL AMPLITUDE OF IDENTIFIED WINDOWS

712 — ESTABLISH ASYSTOLE RANGE

MEDICAL DEVICE AND METHOD FOR DETECTING ARRHYTHMIA

REFERENCE TO RELATED APPLICATIONS

This application claims the benefit of provisional U.S. Patent Application No. 63/278,955, filed on Nov. 12, 2021, the entire contents of which is incorporated by reference herein.

TECHNICAL FIELD

The disclosure relates generally to a medical device and method for sensing cardiac signals and detecting arrhythmia.

BACKGROUND

Medical devices may sense electrophysiological signals from the heart, brain, nerve, muscle or other tissue. Such devices may be implantable, wearable or external devices using implantable and/or surface (skin) electrodes for sensing the electrophysiological signals. In some cases, such devices may be configured to deliver a therapy based on the sensed electrophysiological signals. For example, implantable or external cardiac pacemakers, cardioverter defibrillators, cardiac monitors and the like, sense cardiac electrical signals from a patient's heart. The medical device may sense cardiac electrical signals from a heart chamber and deliver electrical stimulation therapies to the heart chamber using electrodes carried by a transvenous medical electrical lead that positions electrodes within the patient's heart.

A cardiac pacemaker or cardioverter defibrillator may deliver therapeutic electrical stimulation to the heart via electrodes carried by one or more medical electrical leads coupled to the medical device. The electrical stimulation may include electrical pulses such as pacing pulses and/or cardioversion or defibrillation shocks. In some cases, a medical device may sense cardiac electrical signals attendant to the intrinsic depolarizations of the myocardium and control delivery of stimulation pulses to the heart based on sensed cardiac electrical signals. Cardiac signals sensed within a heart chamber using endocardial electrodes carried by transvenous leads, for example, generally have a high signal strength and quality for reliably sensing cardiac electrical events, such as ventricular R-waves sensed from within a ventricle. Upon detection of an abnormal rhythm, such as bradycardia, tachycardia or fibrillation, an appropriate electrical stimulation pulse or pulses may be delivered to restore or maintain a more normal rhythm of the heart. For example, an implantable cardioverter defibrillator (ICD) may deliver pacing pulses to the heart of the patient upon detecting bradycardia or tachycardia or deliver cardioversion or defibrillation (CV/DF) shocks to the heart upon detecting tachycardia or fibrillation.

SUMMARY

In general, this disclosure is directed to a medical device and techniques for sensing cardiac electrical signals and detecting arrhythmias. In some examples, the medical device may be coupled to extracardiac medical leads carrying electrodes positioned outside of the heart for sensing cardiac electrical signals and delivering electrical stimulation pulses, including pacing pulses and/or CV/DF shocks. A medical device operating according to the techniques disclosed herein is configured to sense a cardiac electrical signal and determine an amplitude metric from a cardiac signal segment of the cardiac electrical signal received over a predetermined time interval. Based on the amplitude metric, the medical device may determine whether to perform a first analysis for detecting asystole or a second analysis for detecting tachyarrhythmia. The first analysis may be performed when the amplitude metric is less than an amplitude threshold and may include an analysis of stability of the cardiac electrical signal amplitude for detecting asystole. When asystole is detected, the medical device may deliver one or more cardiac pacing pulses.

The second analysis may be performed for detecting ventricular tachyarrhythmia when the amplitude metric is greater than or equal to an amplitude threshold. The second analysis may include determining morphology parameters that are compared to tachyarrhythmia detection criteria. The tachyarrhythmia detection criteria may be determined to be met based on a low slope content, a spectral width, and/or a mean period determined from the cardiac signal segment in some examples. In other examples, the second analysis may include determining a pulse interval metric from the cardiac signal segment. When the pulse interval metric is less than a tachyarrhythmia threshold interval, and the morphology parameters meet tachyarrhythmia detection criteria, the cardiac signal segment may be determined to be tachyarrhythmia. In still other examples, at least one noise metric may be determined from the cardiac signal segment. The cardiac signal segment may be determined to be tachyarrhythmia when the cardiac signal segment is determined not to be a noisy segment based on the noise metric and other tachyarrhythmia detection criteria are met. The medical device may deliver a therapy, such as anti-tachyarrhythmia pacing (ATP) and/or CV/DF shock when a threshold number of cardiac signal segments are determined to meet the tachyarrhythmia detection criteria for detecting ventricular tachycardia or ventricular fibrillation (VT/VF).

In one example, the disclosure provides a medical device including a sensing circuit configured to sense at least one cardiac electrical signal and a control circuit in communication with the sensing circuit. The control circuit is configured to: determine an amplitude metric from a first cardiac signal segment of the at least one cardiac electrical signal sensed by the sensing circuit over a first predetermined time interval; determine if the amplitude metric meets an amplitude threshold; and perform one of: a first analysis of the first cardiac electrical signal segment for detecting a first arrhythmia in response to the amplitude metric not meeting the amplitude threshold; or a second analysis of the first cardiac electrical signal segment for detecting a second arrhythmia different than the first arrhythmia in response to the amplitude metric meeting the amplitude threshold. The medical device further includes a therapy delivery circuit in communication with the control circuit. The therapy delivery circuit is configured to deliver one of: a first electrical stimulation therapy in response to the control circuit detecting the first arrhythmia based on the first analysis or a second electrical stimulation therapy different than the first electrical stimulation therapy in response to the control circuit detecting the second arrhythmia based on the second analysis.

In some examples, the control circuit is further configured to determine the amplitude metric by identifying signal pulses from the first cardiac signal segment, determining a peak amplitude of each of the identified signal pulses and determining the amplitude metric based on the determined peak amplitudes.

In some examples, the control circuit is further configured to identify the signal pulses from the first cardiac signal segment by identifying a plurality of subsegments of the first cardiac signal segment, determining a local maximum from each of the plurality of subsegments, determining a signal pulse amplitude threshold based on the local maximums, and identifying the signal pulses from the first cardiac signal segment by identifying pulses having an amplitude greater than the signal pulse amplitude threshold. In some examples, the control circuit is further configured to identify the signal pulses by identifying pulses that are at least a minimum time interval apart.

In some examples, the control circuit is further configured to perform the second analysis of the first cardiac signal segment for detecting the second arrhythmia by identifying signal pulse peaks from the first cardiac signal segment, determining peak intervals between the identified signal pulse peaks, determining a peak interval metric based on the determined peak intervals, and determining if the peak interval metric meets a ventricular tachyarrhythmia threshold interval.

In some examples, the control circuit is further configured to determine that the peak interval metric does not meet the ventricular tachyarrhythmia threshold interval and terminate the second analysis of the first cardiac signal segment for detecting the ventricular tachyarrhythmia when the peak interval metric does not meet the ventricular tachyarrhythmia threshold interval.

In some examples, the control circuit is further configured to perform the second analysis of the first cardiac signal segment for detecting the second arrhythmia by determining a noise metric from the first cardiac signal segment, determining that the noise metric does not meet noisy segment criteria, and detecting the second arrhythmia based on the second analysis of the first cardiac signal segment in response to the noise metric not meeting the noisy segment criteria.

In some examples, the control circuit is further configured to determine the noise metric by determining at least one of: a mean rectified amplitude of the first cardiac signal segment; a normalized mean rectified amplitude of the first cardiac signal segment; or a mean period of the first cardiac signal segment.

In some examples, the control circuit is further configured to: determine a subsegment count of noise pulses in each of a plurality of subsegments of the first cardiac signal segment; determine the noise metric by determining a maximum count of the subsegment counts of noise pulses; and determine that the noisy segment criteria are not met when the maximum count is less than a first threshold value.

In some examples, the control circuit is further configured to: determine a subsegment count of noise pulses in each of a plurality of subsegments of the first cardiac signal segment; identify each subsegment of the plurality of subsegments that has a subsegment count of noise pulses that is greater than a second threshold value; determine the noise metric by determining a count of the identified subsegments having the subsegment count of noise pulses that is greater than the second threshold value; determine that the count of the identified subsegments is less than a third threshold value; and determine that the noisy segment criteria are not met when the count of the identified subsegments is less than the third threshold value.

In some examples, the sensing circuit of the medical device is configured to sense ventricular event signals, and the control circuit is further configured to: determine sensed event data from the at least one cardiac electrical signal in response to each of a plurality of ventricular event signals sensed by the sensing circuit; determine that suspected undersensing criteria are met based on the sensed event data; and determine the amplitude metric from the first cardiac signal segment in response to the suspected undersensing criteria being met. In some examples, the control circuit is further configured to determine the sensed event data by determining a ventricular sensed event interval from the ventricular event signals sensed by the sensing circuit. The control circuit may determine that the ventricular sensed event interval meets an undersensing threshold interval and determine that the suspected undersensing criteria are met in response to the ventricular sensed event interval meeting the undersensing threshold interval. In some examples the control circuit is further configured to determine the sensed event data by determining a peak amplitude from the ventricular event signals sensed by the sensing circuit, determine that the peak amplitude is less than an undersensing amplitude threshold, and determine that the suspected undersensing criteria are met in response to the peak amplitude being less than the undersensing threshold amplitude.

In some examples, the control circuit is further configured to determine the sensed event data by determining a morphology matching score between each of the plurality of ventricular event signals sensed by the sensing circuit and an R-wave template, determine that a threshold number of the morphology matching scores are less than a match threshold, and determine that the suspected undersensing criteria are met in response to the threshold number of the morphology matching scores being less than the match threshold.

In some examples, the control circuit is further configured to perform the second analysis of the first cardiac signal segment for detecting the second arrhythmia by determining at least one of: a low slope content from the first cardiac signal segment; a spectral width from the first cardiac signal segment; and a mean period from the first cardiac signal segment. The control circuit may determine that at least one of the low slope content, the spectral width and the mean period meet ventricular tachyarrhythmia segment criteria; and detect the second arrhythmia by detecting ventricular tachyarrhythmia in response to the at least one of the low slope content, the spectral width and the mean period meeting the ventricular tachyarrhythmia segment criteria.

In some examples the control circuit is further configured to perform the second analysis on a second cardiac signal segment of the at least one cardiac electrical signal sensed by the sensing circuit over a second predetermined time interval; determine that the first cardiac signal segment and the second signal segment are tachyarrhythmia signal segments based on the second analysis; and detect the second arrhythmia by detecting ventricular tachyarrhythmia in response to the first cardiac signal segment and the second cardiac signal segment being tachyarrhythmia signal segments.

In some examples, the control circuit is further configured to detect the first arrhythmia by detecting asystole based on the first analysis of the first cardiac signal segment. The control circuit may be further configured to perform the first analysis when the amplitude metric does not meet the amplitude threshold by determining a gradient signal from the first cardiac signal segment and determining that the gradient signal is within an asystole amplitude range for a detection time interval. The control circuit may detect the first arrhythmia based on the first analysis by detecting asystole in response to the gradient signal being within the asystole amplitude range for the detection time interval.

The therapy delivery circuit may be further configured to deliver the first electrical stimulation therapy by delivering at least one pacing pulse in response to the control circuit detecting the first arrhythmia based on the first analysis. In some examples, therapy delivery circuit of the medical device is further configured to deliver the second electrical stimulation therapy by delivering a tachyarrhythmia therapy in response to the control circuit detecting the second arrhythmia based on the second analysis.

In another example, the disclosure provides a method that includes sensing at least one cardiac electrical signal, determining an amplitude metric from a first cardiac signal segment of the at least one cardiac electrical signal sensed over a first predetermined time interval, determining if the amplitude metric meets an amplitude threshold, and performing one of a first analysis of the first cardiac electrical signal segment for detecting a first arrhythmia in response to the amplitude metric not meeting the amplitude threshold or a second analysis of the first cardiac electrical signal segment for detecting a second arrhythmia different than the first arrhythmia in response to the amplitude metric meeting the amplitude threshold. The method may further include delivering one of a first electrical stimulation therapy in response to detecting the first arrhythmia based on the first analysis or a second electrical stimulation therapy different than the first electrical stimulation therapy in response to detecting the second arrhythmia based on the second analysis.

The method may include determining the amplitude metric by identifying signal pulses from the first cardiac signal segment, determining a peak amplitude of each of the identified signal pulses; and determining the amplitude metric based on the determined peak amplitudes. The method may further include identifying the signal pulses from the first cardiac signal segment by identifying a plurality of subsegments of the first cardiac signal segment, determining a local maximum from each of the plurality of subsegments, determining a signal pulse amplitude threshold based on the local maximums; and identifying the signal pulses from the first cardiac signal segment by identifying pulses having an amplitude greater than the signal pulse amplitude threshold. The method may further include identifying the signal pulses by identifying pulses that are at least a minimum time interval apart.

The method may further include performing the second analysis of the first cardiac signal segment for detecting the second arrhythmia by identifying signal pulse peaks from the first cardiac signal segment, determining peak intervals between the identified signal pulse peaks, determining a peak interval metric based on the determined peak intervals, and determining if the peak interval metric meets a ventricular tachyarrhythmia threshold interval. In some examples, the method may further include determining that the peak interval metric does not meet the ventricular tachyarrhythmia threshold interval; and terminating the second analysis of the first cardiac signal segment for detecting the ventricular tachyarrhythmia when the peak interval metric does not meet the ventricular tachyarrhythmia threshold interval.

In some examples, the method may further include performing the second analysis of the first cardiac signal segment for detecting the second arrhythmia by determining a noise metric from the first cardiac signal segment; determining that the noise metric does not meet noisy segment criteria; and detecting the second arrhythmia based on the second analysis of the first cardiac signal segment in response to the noise metric not meeting the noisy segment criteria. The method may include determining the noise metric by determining at least one of: a mean rectified amplitude of the first cardiac signal segment; a normalized amplitude of the first cardiac signal segment; a normalized mean rectified amplitude of the first cardiac signal segment; and a mean period of the first cardiac signal segment.

In some examples, the method may further include determining a subsegment count of noise pulses in each of a plurality of subsegments of the first cardiac signal segment; determining the noise metric by determining a maximum count of the subsegment counts of noise pulses; and determining that the noisy segment criteria are not met when the maximum count is less than a first threshold value.

In some examples, the method may further include: determining a subsegment count of noise pulses in each of a plurality of subsegments of the first cardiac signal segment; identifying each subsegment of the plurality of subsegments that has a subsegment count of noise pulses that is greater than a second threshold value; determining the noise metric by determining a count of the identified subsegments having the subsegment count of noise pulses that is greater than the second threshold value; determining that the count of the identified subsegments is less than a third threshold value; and determining that the noisy segment criteria are not met when the count of the identified subsegments is less than the third threshold value.

In some examples, the method may further include sensing ventricular event signals, determining sensed event data from the at least one cardiac electrical signal in response to each of a plurality of sensed ventricular event signals, determining that suspected undersensing criteria are met based on the sensed event data; and determining the amplitude metric from the first cardiac signal segment in response to the suspected undersensing criteria being met. The method may include determining the sensed event data by determining a ventricular sensed event interval from the sensed ventricular event signals, determining that the ventricular sensed event interval meets an undersensing threshold interval; and determining that the suspected undersensing criteria are met in response to the ventricular sensed event interval meeting the undersensing threshold interval. In some examples, the method may further include determining the sensed event data by determining a peak amplitude from the sensed ventricular event signals, determining that the peak amplitude is less than an undersensing amplitude threshold; and determining that the suspected undersensing criteria are met in response to the peak amplitude being less than the undersensing threshold amplitude.

In some examples, the method may further include determining the sensed event data by determining a morphology matching score between each of the plurality of sensed ventricular event signals and an R-wave template, determining that a threshold number of the morphology matching scores are less than a match threshold, and determining that the suspected undersensing criteria are met in response to the threshold number of the morphology matching scores being less than the match threshold.

In some examples, the method may further include performing the second analysis of the first cardiac signal segment for detecting the second arrhythmia by determining at least one of: a low slope content from the first cardiac signal segment; a spectral width from the first cardiac signal segment; a mean period from the first cardiac signal segment. The method may further include determining that at least one of the low slope content, the spectral width and the mean period meet ventricular tachyarrhythmia segment criteria and detecting the second arrhythmia by detecting ventricular tachyarrhythmia in response to the at least one of the low slope content, the spectral width and the mean period meeting the ventricular tachyarrhythmia segment criteria.

The method may further include performing the second analysis on a second cardiac signal segment of the at least one cardiac electrical signal sensed over a second predetermined time interval, determining that the first cardiac signal segment and the second cardiac signal segment are tachyarrhythmia signal segments based on the second analysis, and detecting the second arrhythmia by detecting ventricular tachyarrhythmia in response to the first cardiac signal segment and the second cardiac signal segment being tachyarrhythmia signal segments.

In some examples, method may include detecting the first arrhythmia by detecting asystole based on the first analysis of the first cardiac signal segment. The method may include performing the first analysis when the amplitude metric does not meet the amplitude threshold by determining a gradient signal from the first cardiac signal segment, determining that the gradient signal is within an asystole amplitude range for a detection time interval, detecting the first arrhythmia based on the first analysis by detecting asystole in response to the gradient signal being within the asystole amplitude range for the detection time interval.

The method may include delivering the first electrical stimulation therapy by delivering at least one pacing pulse in response to detecting the first arrhythmia based on the first analysis. The method may include delivering the second electrical stimulation therapy by delivering a tachyarrhythmia therapy in response to detecting the second arrhythmia based on the second analysis.

In another example, the disclosure provides a non-transitory computer-readable medium storing a set of instructions which, when executed by a control circuit of a medical device, cause the medical device to sense at least one cardiac electrical signal; determine an amplitude metric from a cardiac signal segment of the at least one cardiac electrical signal sensed over a predetermined time interval; and determine if the amplitude metric meets an amplitude threshold. The instructions may further cause the device to perform one of: a first analysis of the cardiac electrical signal segment for detecting a first arrhythmia in response to the amplitude metric not meeting the amplitude threshold; or a second analysis of the cardiac electrical signal segment for detecting a second arrhythmia different than the first arrhythmia in response to the amplitude metric meeting the amplitude threshold. The instructions may further cause the device to deliver one of: a first electrical stimulation therapy in response to detecting the first arrhythmia based on the first analysis; or a second electrical stimulation therapy different than the first electrical stimulation therapy in response to detecting the second arrhythmia based on the second analysis.

In another example, the disclosure provides a medical device including a sensing circuit configured to sense a cardiac electrical signal and a control circuit in communication with the sensing circuit. The control circuit may be configured to: determine an amplitude metric from a first cardiac signal segment of the cardiac electrical signal sensed by the sensing circuit over a first predetermined time interval; determine that the amplitude metric meets an amplitude threshold; perform an analysis of the first cardiac electrical signal segment for detecting a tachyarrhythmia in response to the amplitude metric meeting the amplitude threshold; and detect the tachyarrhythmia based on the analysis of the cardiac electrical signal segment. The medical device may further include a therapy delivery circuit in communication with the control circuit, the therapy delivery circuit configured to deliver a tachyarrhythmia therapy in response to the control circuit detecting the tachyarrhythmia.

In some examples, the control circuit is further configured to perform the analysis of the first cardiac signal segment for detecting the tachyarrhythmia by: identifying signal pulse peaks from the first cardiac signal segment; determining peak intervals between the identified signal pulse peaks; determining a peak interval metric based on the determined peak intervals; and determining that the peak interval metric is less than a ventricular tachyarrhythmia threshold interval.

In some examples, the control circuit is further configured to perform the analysis of the first cardiac signal segment for detecting the tachyarrhythmia by determining a noise metric from the first cardiac signal segment; determining that the noise metric does not meet noisy segment criteria; and detecting the tachyarrhythmia based on the analysis of the first cardiac signal segment when the noise metric does not meet the noisy segment criteria.

In some examples, the control circuit is further configured to perform the analysis of the first cardiac signal segment for detecting the tachyarrhythmia by determining at least one of: a low slope content from the first cardiac signal segment; a spectral width from the first cardiac signal segment; and a mean period from the first cardiac signal segment. The control circuit may be configured to determine that each of the low slope content, the spectral width and the mean period meet tachyarrhythmia segment criteria; and detect the tachyarrhythmia in response to the low slope content, the spectral width and the mean period meeting the tachyarrhythmia segment criteria.

The control circuit may be further configured to perform the analysis on a second cardiac signal segment of the cardiac electrical signal sensed by the sensing circuit over a second predetermined time interval, determine that the first cardiac signal segment and the second signal segment are tachyarrhythmia signal segments based on the analysis, and detect the tachyarrhythmia in response to the first cardiac signal segment and the second cardiac signal segment being tachyarrhythmia signal segments.

In yet another example, the disclosure provides a medical device comprising a sensing circuit configured to sense a cardiac electrical signal and a control circuit coupled to the sensing circuit and configured to determine an amplitude metric from a cardiac signal segment of the cardiac electrical signal sensed over a predetermined time interval, determine that the amplitude metric is less than an amplitude threshold and perform an analysis of the cardiac signal segment for detecting asystole in response to the amplitude metric being less than the amplitude threshold. The control circuit may be further configured to detect asystole based on the analysis of the cardiac signal segment and schedule a cardiac pacing pulse in response to detecting the asystole. The medical device may further include a therapy delivery circuit in communication with the control circuit, the therapy delivery circuit configured to deliver the scheduled cardiac pacing pulse in response to the control circuit detecting the asystole.

In some examples, the control circuit may be configured to perform the analysis for detecting asystole by determining a gradient signal from the cardiac signal segment and determining that the gradient signal is within an asystole amplitude range for a detection time interval. The control circuit may detect the asystole in response to the gradient signal being within the asystole amplitude range for the detection time interval. In some examples, the control circuit may be further configured to determine a low pass filtered signal from the cardiac signal segment; and determine the gradient signal from the low pass filtered signal.

In some examples, the control circuit may be further configured to establish the asystole amplitude range by determining a gradient signal from the cardiac electrical signal sensed by the sensing circuit, identifying zero crossings of the gradient signal, identifying a plurality of time windows having at least a threshold number of zero crossings, determining a representative amplitude of the gradient signal in the identified plurality of time windows, and setting the asystole amplitude range based on the representative amplitude.

The control circuit may be further configured to perform the analysis of the cardiac signal segment for detecting asystole by determining a gradient signal from the cardiac signal segment, setting a plurality of time windows in the cardiac signal segment, identifying each time window of the plurality of time windows in which a threshold number of gradient signal sample points are within an asystole amplitude range and detecting the asystole when the identified time windows of the plurality of time windows in which the threshold number of gradient signal sample points are within the asystole amplitude range reaches a threshold number of time windows.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes a medical device and techniques for detecting arrhythmia. In various examples, the medical device performing the techniques disclosed herein may be included in an ICD system capable of sensing cardiac electrical signals, detecting arrhythmia based on an analysis of the sensed cardiac electrical signals, and delivering electrical stimulation therapy for treating the arrhythmia. In some examples, the ICD is coupled to an extra-cardiovascular lead. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. In other examples, a transvenous extra-cardiac lead may carry implantable electrodes that can be positioned intravenously but outside the heart in an extra-cardiac location, e.g., within the internal thoracic vein, jugular vein, or other vein, for sensing cardiac electrical signals and delivering cardiac pacing pulses.

Figure 1A:
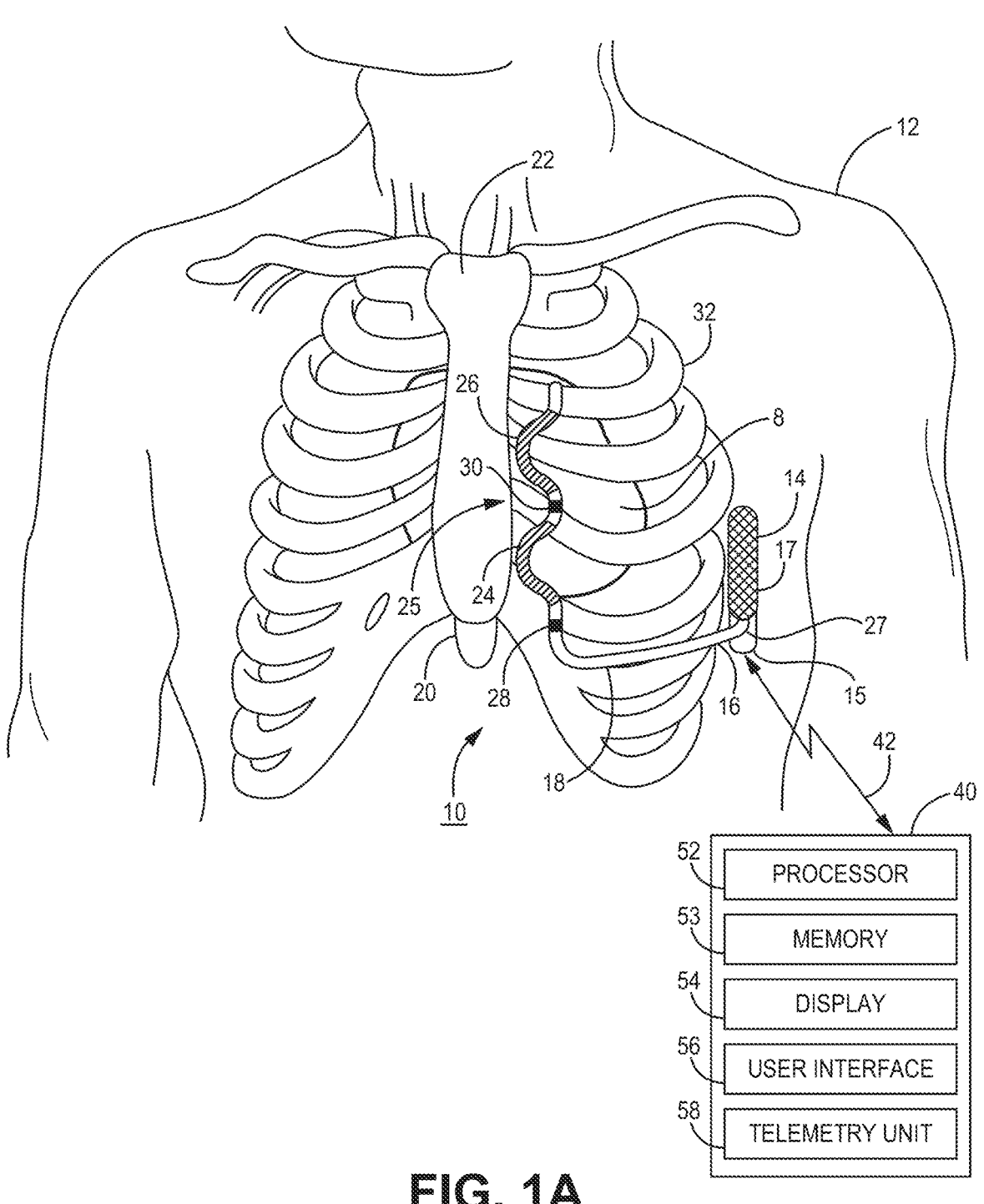
FIGS. 1A and 1B are conceptual diagrams of one example of an ICD system that may be configured to sense cardiac event signals, detect arrhythmia and deliver electrical stimulation therapy according to the techniques disclosed herein.
Figure 1B:
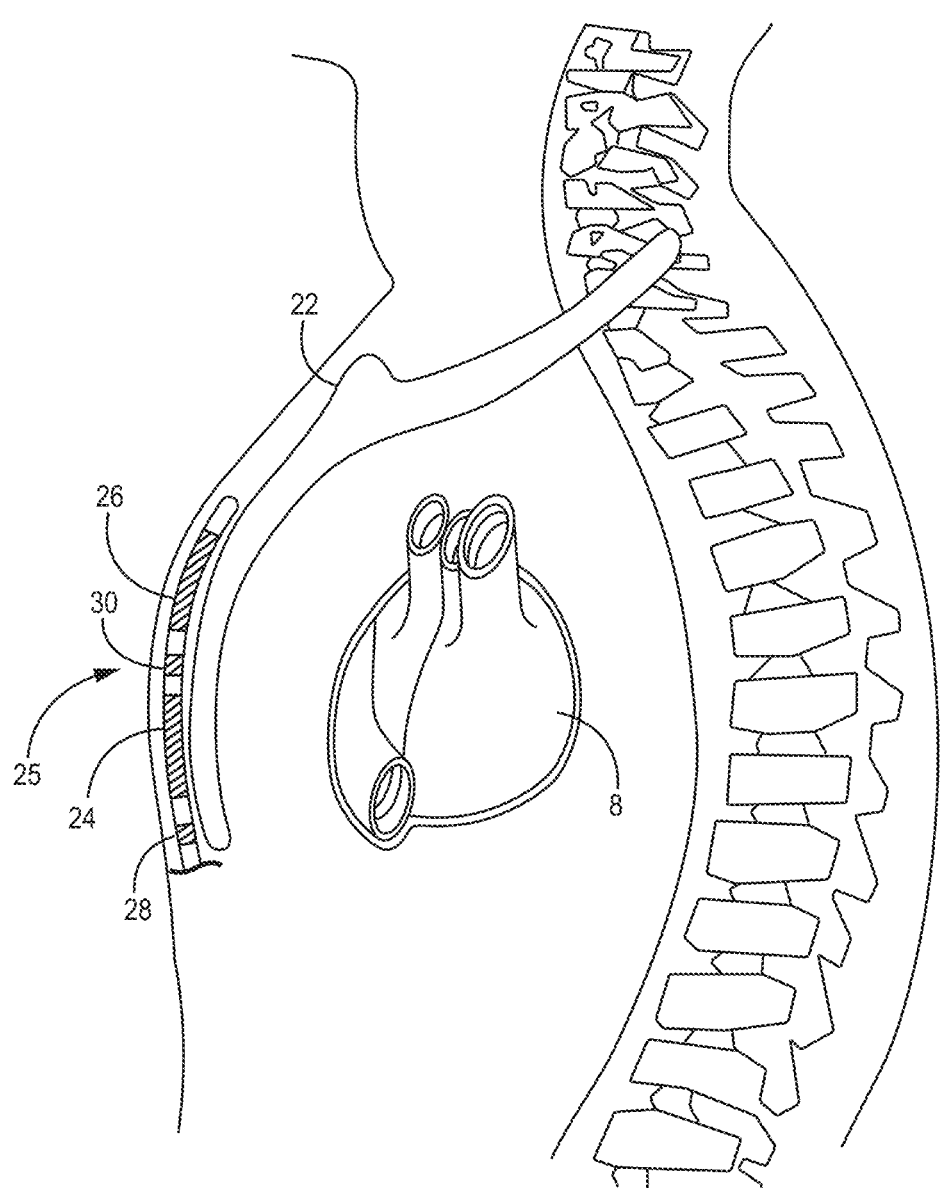

FIGS. 1A and 1B are conceptual diagrams of one example of an ICD system 10 that may be configured to sense cardiac electrical signals, detect arrhythmia and deliver electrical stimulation therapy according to the techniques disclosed herein. FIG. 1A is a front view of ICD system 10 implanted within patient 12. FIG. 1B is a side view of ICD system 10 implanted within patient 12. ICD system 10 includes an ICD 14 connected to an electrical stimulation and sensing lead 16, positioned in an extra-cardiovascular location in this example. FIGS. 1A and 1B are described in the context of an ICD system 10 capable of providing high voltage CV/DF shocks and/or cardiac pacing pulses in response to detecting a cardiac arrhythmia based on processing of sensed cardiac electrical signals. The techniques for detecting arrhythmia as disclosed herein may be implemented in a cardiac monitoring device that does not include cardiac pacing and/or CV/DF shock delivery capabilities in some examples. Furthermore, the techniques disclosed herein for sensing cardiac electrical signals and detecting arrhythmia may be implemented in a variety of medical devices including external or implantable cardiac monitors, pacemakers, and ICDs.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, relatively lower voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processing circuits, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., CV/DF shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, either of electrodes 24 and 26 may be used as a sensing electrode in a sensing electrode vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 28 and 30 may provide only pacing functionality, only sensing functionality or both.

ICD 14 may obtain cardiac electrical signals corresponding to electrical activity of heart 8 via a combination of sensing electrode vectors that include combinations of electrodes 24, 26, 28 and/or 30. In some examples, housing 15 of ICD 14 is used in combination with one or more of electrodes 24, 26, 28 and/or 30 in at least one sensing electrode vector. Various sensing electrode vectors utilizing combinations of electrodes 24, 26, 28, and 30 and housing 15 are described below for sensing one or more cardiac electrical signals. Each cardiac electrical signal that is sensed by ICD 14 may be sensed using a different sensing electrode vector, which may be selected by sensing circuitry included in ICD 14. As described herein, in some examples the cardiac electrical signal(s) received via a selected sensing electrode vector may be used by ICD 14 for sensing cardiac event signals attendant to intrinsic depolarizations of the myocardium, e.g., R-waves attendant to ventricular depolarization and in some cases P-waves attendant to atrial depolarization. Sensed cardiac event signals may be used for determining the heart rate and determining a need for cardiac pacing, e.g., for treating bradycardia or asystole for preventing a long ventricular pause, or for determining a need for tachyarrhythmia therapies, e.g., anti-tachycardia pacing (ATP) or CV/DF shocks.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors.

The techniques disclosed herein are not limited to a particular path of lead 16 or final locations of electrodes 24, 26, 28 and 30.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit electrical stimulation pulses from a therapy delivery circuit within ICD 14 to one or more of defibrillation electrodes 24 and 26 and/or pace/sense electrodes 28 and 30 and transmit electrical signals produced by the patient's heart 8 from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zigzagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in U.S. Pat. No. 10,675,478 (Marshall, et al.), incorporated herein by reference in its entirety. The techniques disclosed herein are not limited to any particular lead body design, however. In other examples, lead body 18 is a flexible elongated lead body without any pre-formed shape, bends or curves.

ICD 14 analyzes the cardiac electrical signal(s) received from one or more sensing electrode vectors to monitor for abnormal rhythms, such as asystole, bradycardia, ventricular tachycardia (VT) and/or ventricular fibrillation (VF). ICD 14 may analyze the heart rate and/or morphology of the cardiac electrical signals to monitor for tachyarrhythmia in accordance with tachyarrhythmia detection techniques. ICD 14 generates and delivers electrical stimulation therapy in response to detecting a tachyarrhythmia, e.g., VT or VF (VT/VF) using a therapy delivery electrode vector which may be selected from any of the available electrodes 24, 26, 28 30 and/or housing 15. ICD 14 may deliver ATP in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15.

In the absence of a ventricular event signal, ICD 14 may generate and deliver a cardiac pacing pulse, such as a post-shock pacing pulse or bradycardia pacing pulse when asystole is detected or when a pacing escape interval expires prior to sensing a ventricular event signal, e.g., when AV block is present. The cardiac pacing pulses may be delivered using a pacing electrode vector that includes one or more of the electrodes 24, 26, 28, and 30 and the housing 15 of ICD 14.

As described below, at least one sensing electrode vector may be selected for sensing a cardiac signal segment over a predetermined time interval to detect asystole or tachyarrhythmia occurring during the time interval. In some examples, a threshold number of cardiac signal segments may be required to meet asystole detection criteria for detecting asystole and delivering a cardiac pacing pulse in response to the asystole detection. In other instances, a threshold number of cardiac signal segments may be required to meet tachyarrhythmia detection criteria in order to detect tachyarrhythmia and deliver ATP and/or CV/DF shocks.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space. FIGS. 1A and 1B are illustrative in nature and should not be considered limiting in the practice of the techniques disclosed herein.

A medical device operating according to techniques disclosed herein may be coupled to a transvenous or non-transvenous lead in various examples for carrying electrodes for sensing cardiac electrical signals and delivering electrical stimulation therapy. For example, the medical device, such as ICD 14, may be coupled to an extra-cardiovascular lead as illustrated in the accompanying drawings, referring to a lead that positions electrodes outside the blood vessels, heart, and pericardium surrounding the heart of a patient. Implantable electrodes carried by extra-cardiovascular leads may be positioned extra-thoracically (outside the ribcage and sternum), subcutaneously or submuscularly, or intra-thoracically (beneath the ribcage or sternum, sometimes referred to as a sub-sternal position) and may not necessarily be in intimate contact with myocardial tissue. An extra-cardiovascular lead may also be referred to as a "non-transvenous" lead.

In other examples, the medical device may be coupled to a transvenous lead that positions electrodes within a blood vessel, which may remain outside the heart in an "extra-cardiac" location or be advanced to position electrodes within a heart chamber. For instance, a transvenous medical lead may be advanced along a venous pathway to position electrodes in an extra-cardiac location within the internal thoracic vein (ITV), an intercostal vein, the superior epigastric vein, or the azygos, hemiazygos, or accessory hemiazygos veins, as examples. In still other examples, a transvenous lead may be advanced to position electrodes within the heart, e.g., within an atrial and/or ventricular heart chambers.

An external device 40 is shown in telemetric communication with ICD 14 by a wireless communication link 42 in FIG. 1A. External device 40 may include a processor 52, memory 53, display 54, user interface 56 and telemetry unit 58. Processor 52 controls external device operations and processes data and signals received from ICD 14. Display unit 54, which may include a graphical user interface, displays data and other information to a user for reviewing ICD operation and programmed parameters as well as cardiac electrical signals retrieved from ICD 14.

User interface 56 may include a mouse, touch screen, keypad or the like to enable a user to interact with external device 40 to initiate a telemetry session with ICD 14 for retrieving data from and/or transmitting data to ICD 14, including programmable parameters for controlling cardiac event signal sensing, arrhythmia detection and therapy delivery. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, battery status, and histories of detected rhythm episodes and delivered therapies, etc., may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or handheld device. External device 40 may be used to program cardiac signal sensing parameters, cardiac rhythm detection parameters and therapy control parameters used by ICD 14. At least some control parameters used in sensing cardiac event signals and detecting arrhythmias according to the techniques disclosed herein as well as therapy delivery may be programmed into ICD 14 using external device 40 in some examples.

Figure 2A:
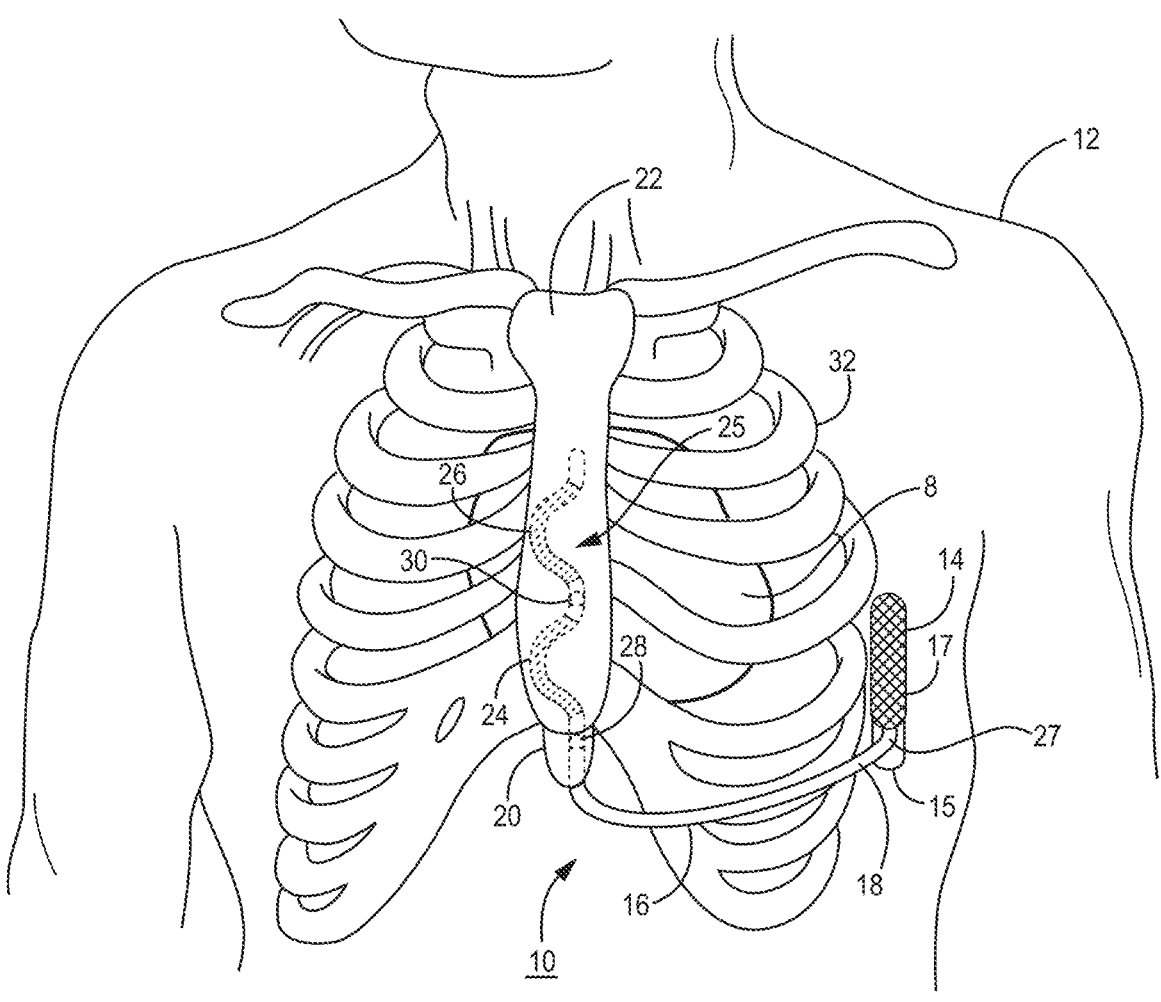
FIGS. 2A-2C are conceptual diagrams of a patient implanted with an ICD system in a different implant configuration than the arrangement shown in FIGS. 1A-1B.
Figure 2B:
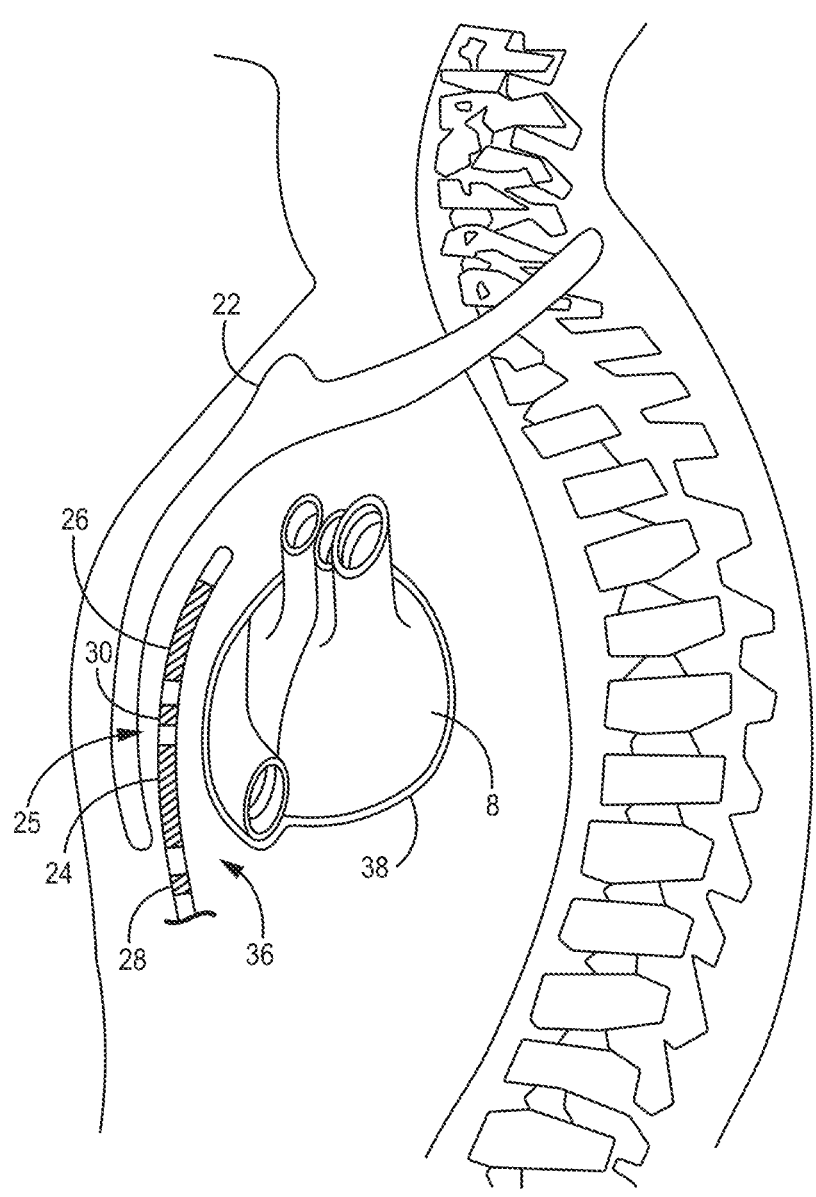
Figure 2C:
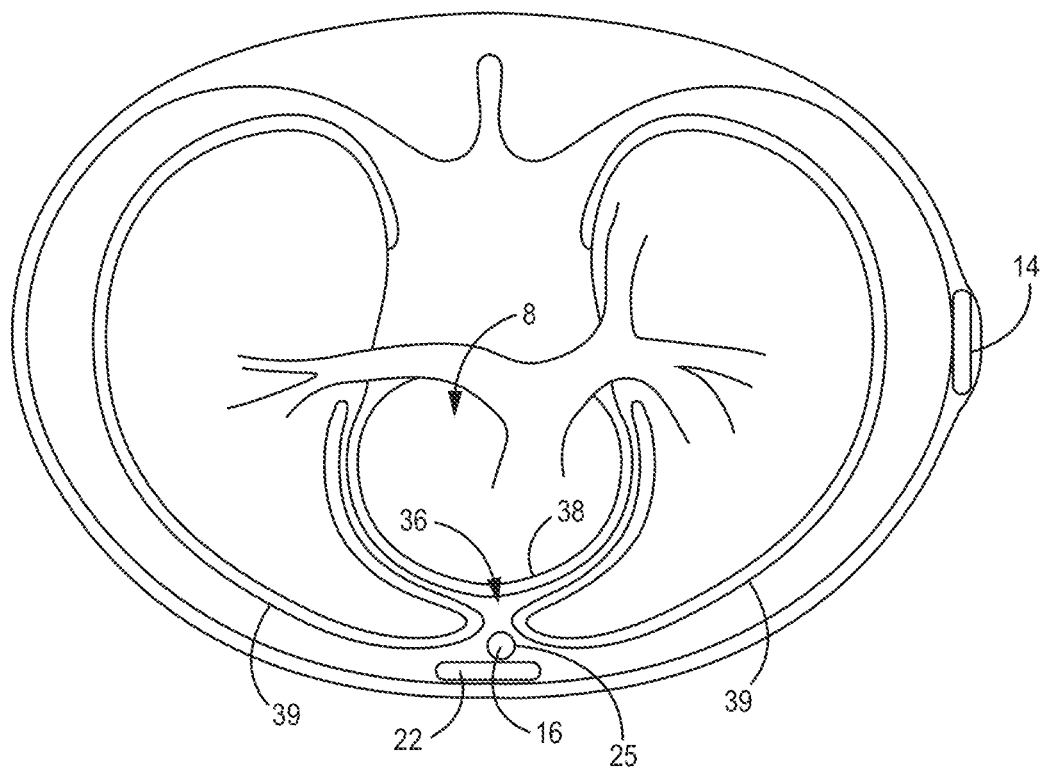

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 (see FIG. 2C) in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiac, intra-thoracic locations, including in the pleural cavity or around the perimeter of and adjacent to the pericardium 38 of heart 8.

In the various example implant locations of lead 16 and electrodes 24, 26, 28 and 30 shown and described herein, cardiac signals sensed by ICD 14 may have a relatively low and/or variable signal strength, e.g., caused by postural changes, respiration or other body movement, and/or may be contaminated by skeletal muscle myopotentials and/or environmental EMI. Undersensing of R-waves or fibrillation waves may result in an undetected tachyarrhythmia when ATP or CV/DF therapy may be needed. Oversensing of P-waves, T-waves, skeletal muscle myopotentials or other noise may lead to a false tachyarrhythmia detection resulting in unnecessary ATP or CV/DF shock delivery. In other instances, oversensing of cardiac noise (P-waves or T-waves) or non-cardiac noise (skeletal muscle myopotentials, EMI or other electrical noise) may result in withholding of pacing pulses when cardiac pacing is needed to prevent a long ventricular pause. Techniques disclosed herein provide improvements in detecting arrhythmias by an implantable medical device. Improvements in detecting arrhythmias with high sensitivity and specificity can improve the performance of the implantable medical device in delivering appropriate electrical stimulation therapy for successful treating the detected arrhythmia.

Figure 3:
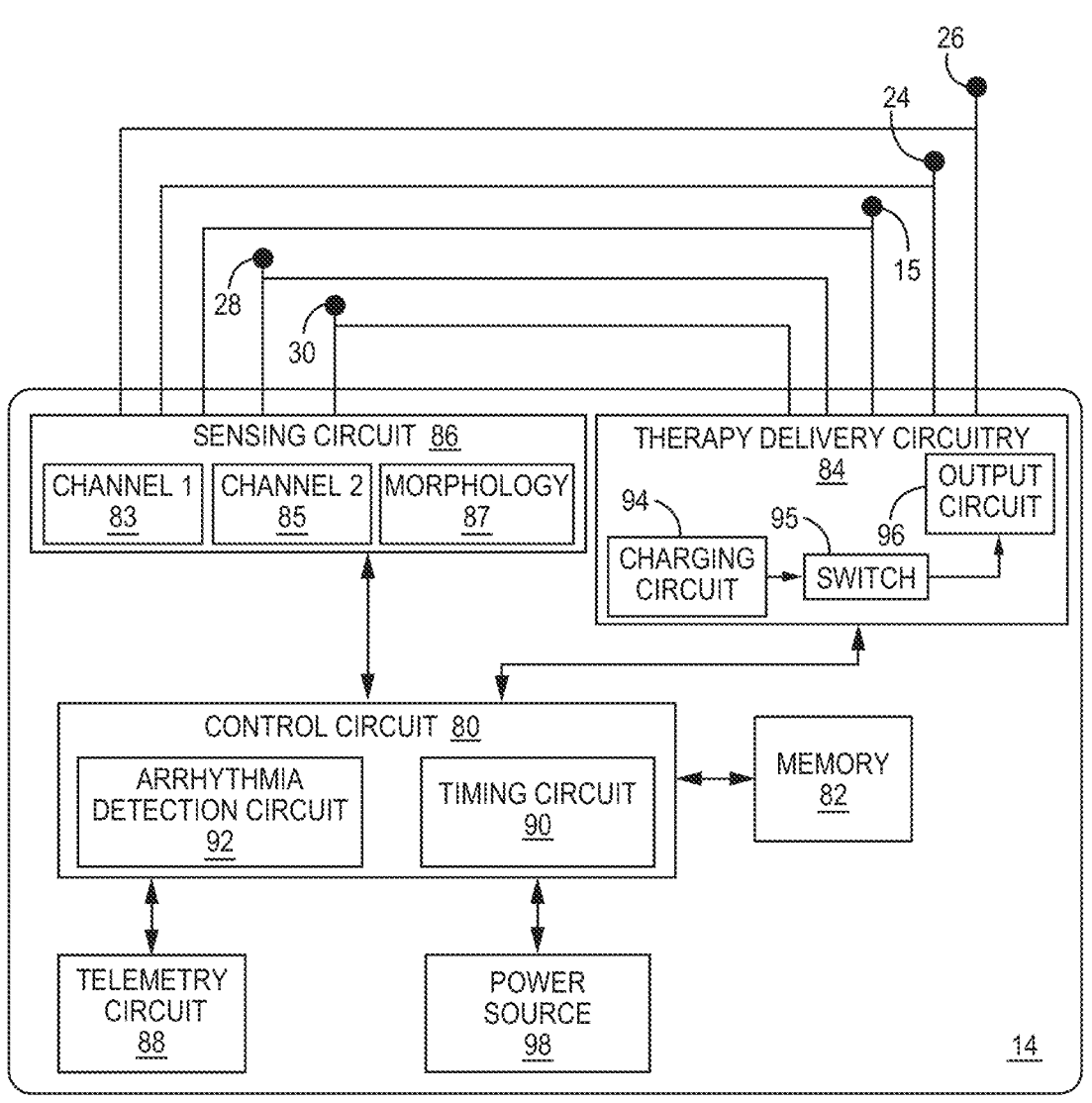
FIG. 3 is a conceptual diagram of an ICD according to one example.

FIG. 3 is a conceptual diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapy as needed according to programmed therapy delivery algorithms and control parameters. ICD 14 may be coupled to a lead, such as lead 16 carrying electrodes 24, 26, 28, and 30, for delivering electrical stimulation pulses to the patient's heart and for sensing cardiac electrical signals.

ICD 14 includes a control circuit 80, memory 82, therapy delivery circuit 84, cardiac electrical signal sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3 but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol. Power source 98 is also coupled to components of cardiac electrical signal sensing circuit 86, such as sense amplifiers, analog-to-digital converters, switching circuitry, etc. as needed.

The circuits shown in FIG. 3 represent functionality included in ICD 14 and may include any discrete and/or integrated electronic circuit components that implement analog and/or digital circuits capable of producing the functions attributed to ICD 14 herein. Functionality associated with one or more circuits may be performed by separate hardware, firmware and/or software components, or integrated within common hardware, firmware and/or software components. For example, cardiac electrical signal sensing and analysis for detecting arrhythmia may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

Control circuit 80 may include hardware configured to perform subroutines of signal processing and analysis techniques disclosed herein to reduce the processing burden associated with firmware and/or software execution of processing routines. For example hardware subroutines (HSRs) may be implemented in control circuit 80 to perform specific processing functions such as dedicated math operations, which may include any of sum, absolute value, difference, extrema, histogram counts, signal filtering (e.g., biquad filter, difference filter or other filters), etc. These HSRs could be called by control circuit firmware when processing and analyzing a cardiac signal for detecting arrhythmia, which may include a low pass filter, difference filter, gradient filter or other signal processing. HSRs may be called when control circuit 80 is determining various morphology parameters from a cardiac signal for detecting arrhythmia as described herein, which may include any of a mean period, spectral width, low slope content, signal pulse amplitudes, signal pulse intervals, etc. These HSRs can unload the processing burden associated with firmware and/or software processing to reduce current drain of power source 98 and thereby extend the useful life of ICD 14.

The various circuits of ICD 14 may include an application specific integrated circuit (ASIC), an electronic circuit, a processor (shared, dedicated, or group) and memory that execute one or more software or firmware programs, a combinational logic circuit, state machine, HSR, or other suitable components or combinations of components that provide the described functionality. The particular form of software, hardware and/or firmware employed to implement the functionality disclosed herein will be determined primarily by the particular system architecture employed in the ICD and by the particular sensing, detection and therapy delivery methodologies employed by the ICD. Providing software, hardware, and/or firmware to accomplish the described functionality in the context of any modern medical device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical signals, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Cardiac electrical signal sensing circuit 86 (also referred to herein as "sensing circuit" 86) may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to receive cardiac electrical signals from at least one sensing electrode vector selected from the available electrodes 24, 26, 28, 30, and housing 15 in some examples. At least two, three or more cardiac electrical signals from two, three or more different sensing electrode vectors may be received simultaneously by sensing circuit 86 in some examples. Sensing circuit 86 may monitor one or more cardiac electrical signals for sensing cardiac event signals, e.g., R-waves attendant to intrinsic ventricular myocardial depolarizations. In some examples, sensing circuit 86 may be configured to monitor two cardiac electrical signals simultaneously for sensing cardiac event signals. At least one cardiac electrical signal may be received by sensing circuit 86 and passed to control circuit 80 for processing and analysis for determining when morphology-based criteria for detecting asystole or a tachyarrhythmia are met. As described below, a cardiac electrical signal received over a predetermined time interval may be analyzed for detecting asystole or tachyarrhythmia. In the example shown, sensing circuit 86 may include switching circuitry for selecting which of electrodes 24, 26, 28, 30, and housing 15 are coupled as a first sensing electrode vector to a first sensing channel 83 for receiving a first cardiac electrical signal, which electrodes are coupled as a second sensing electrode vector to a second sensing channel 85 of sensing circuit 86 for receiving a second cardiac electrical signal, and which electrodes are coupled as a third sensing electrode vector to a morphology signal channel 87 for receiving a third cardiac electrical signal.

Each sensing channel 83 and 85, when included, may be configured to amplify, filter and digitize the cardiac electrical signal received from selected electrodes coupled to the respective sensing channel to improve the signal quality for sensing cardiac event signals, such as R-waves. The cardiac event detection circuitry within sensing circuit 86 may include one or more sense amplifiers, filters, rectifiers, threshold detectors, comparators, analog-to-digital converters (ADCs), timers or other analog and/or digital components as described further in conjunction with FIG. 4. A cardiac event sensing threshold may be automatically adjusted by each sensing channel 83 and 85 under the control of control circuit 80, based on sensing threshold control parameters, such as various timing intervals and sensing threshold amplitude values that may be determined by control circuit 80, stored in memory 82, and/or controlled by hardware, firmware and/or software of control circuit 80 and/or sensing circuit 86.

First sensing channel 83 and second sensing channel 85 may each control a cardiac event sensing threshold, e.g., an R-wave sensing threshold, that is applied to the incoming cardiac electrical signal for sensing cardiac event signals, e.g., R-waves. Upon sensing a cardiac event signal based on a sensing threshold crossing, first sensing channel 83 may produce a sensed event signal that is passed to control circuit 80. For example, upon detecting an R-wave sensing threshold crossing by the cardiac electrical signal received via a first sensing electrode vector, the first sensing channel 83 may generate a ventricular sensed event signal that is passed to control circuit 80. Similarly, upon detecting an R-wave sensing threshold crossing by a second cardiac electrical signal received by second sensing channel 85, the second sensing channel 85 may generate a ventricular sensed event signal that is passed to control circuit 80. The first and second sensing channels 83 and 85 may be configured to automatically adjust the R-wave sensing threshold used by each channel separately. The ventricular sensed event signals and relative timing from each other may be used by control circuit 80 for determining sensed event intervals for use in detecting tachyarrhythmia and/or controlling bradycardia pacing pulse delivery.

Ventricular sensed event signals received from sensing circuit 86 by control circuit 80 can be used by control circuit 80 for determining sensed event intervals, which are referred to herein as RR intervals (RRIs). An RRI is the time interval between two ventricular sensed event signals received by control circuit 80 from the same sensing channel 83 or 85, which may also be referred to as an "in-channel" sensed event interval. Control circuit 80 may include a timing circuit 90 for determining RRIs between consecutive ventricular sensed event signals received from a given sensing channel 83 or 85. Based on RRIs, control circuit 80 may detect VT/VF in some examples. In some instances, when a ventricular sensed event signal is received following a delivered pacing pulse, the RRI is determined from the pacing pulse to the ventricular sensed event signal. As such, RRIs may include time intervals between consecutive ventricular sensed event signal and intervals between a delivered pacing pulse and a ventricular sensed event signal.

Illustrative techniques disclosed herein are described in conjunction with sensing circuit 86 configured to receive two different cardiac electrical signals by the two cardiac event sensing channels 83 and 85 for sensing R-waves from the two cardiac electrical signals and for receiving a third cardiac electrical signal by morphology signal channel 87 for passing a digitized electrocardiogram (ECG) signal to control circuit 80 for morphology analysis. The three cardiac electrical signals sensed by sensing circuit 86 may be received using three different sensing electrode vectors selected from the available electrodes 24, 26, 28 and 30 and housing 15. In other examples, two cardiac electrical signals may be received by sensing circuit 86 from two different sensing electrode vectors, with one signal passed to the first sensing channel 83 and the other signal passed to the second sensing channel 85. Either or both of the two signals may be passed to control circuit 80 as a multi-bit digital ECG signal used by control circuit 80 for morphology analysis for analysis of a predetermined time segment of the ECG signal for detecting asystole and tachyarrhythmia according to the techniques disclosed herein.

Sensing channels 83 and 85 may be optional in some examples, however. Aspects of the techniques disclosed herein for detecting arrhythmia may be performed by processing and analyzing a single cardiac electrical signal sensed by morphology signal channel 87. As described below, one or more time segments of a multi-bit digital ECG signal received from morphology signal channel 87 may be analyzed by control circuit 80 for detecting asystole or tachyarrhythmia without requiring ventricular sensed event signals from sensing channels 83 and 85.

Timing circuit 90 may be configured to control various timers and/or counters used in setting various intervals and windows used in sensing ventricular event signals, determining time intervals between received ventricular sensed event signals, performing morphology analysis and controlling the timing of cardiac pacing pulses generated by therapy delivery circuit 84. Timing circuit 90 may start a timer in response to receiving ventricular sensed event signals from sensing channels 83 and 85 for timing the RRIs between consecutively received in-channel ventricular sensed event signals (and in some instances from a delivered pacing pulse to a ventricular sensed event signal). Control circuit may pass the RRI to arrhythmia detection circuit 92 for determining and counting tachyarrhythmia intervals.

Control circuit 80 may include an arrhythmia detection circuit 92 configured to analyze RRIs received from timing circuit 90 and cardiac electrical signals received from morphology signal channel 87 for detecting arrhythmia. Arrhythmia detection circuit 92 may be configured to detect asystole and tachyarrhythmia based on sensed cardiac electrical signals meeting respective asystole or tachyarrhythmia detection criteria. For example, when a threshold number of ventricular sensed event signals from one sensing channel 83 or 85 each occur at a sensed event interval (RRI) that is less than a tachyarrhythmia detection interval, control circuit 80 may detect VT/VF. An RRI that is less than the tachyarrhythmia detection interval is referred to as a "tachyarrhythmia interval." In some examples, a tachyarrhythmia detection based on the threshold number of tachyarrhythmia intervals being reached may be confirmed or rejected based on morphology analysis of a cardiac electrical signal.

In other examples, asystole or VT/VF may be detected by arrhythmia detection circuit 92 based on morphology analysis of a cardiac electrical signal sensed by morphology signal channel 87 over a predetermined time interval, e.g., 0.5 seconds to 8 seconds, or 3 seconds in an example, without requiring a determination of RRIs. In some examples, arrhythmia detection circuit 92 may perform morphology analysis of cardiac signal segments for detecting arrhythmia without analyzing RRIs determined from ventricular sensed event signals received from sensing channels 83 and 85. In other examples, morphology analysis of cardiac signal segments by arrhythmia detection circuit 92 may be triggered by control circuit 80 when undersensing of R-waves by sensing channels 83 and 85 is suspected. Methods for determining suspected undersensing of ventricular event signals by sensing channels 83 and 85 are described below in conjunction with FIGS. 19 and 20.

Arrhythmia detection circuit 92 may be implemented in control circuit 80 as hardware, software and/or firmware that processes and analyzes signals received from sensing circuit 86 for detecting arrhythmia, including asystole and VT/VF. Arrhythmia detection circuit may identify signal pulses for determining amplitude and/or pulse interval metrics of a time segment of a cardiac electrical signal for use in detecting arrhythmia as further described below. Arrhythmia detection circuit 92 may be configured to determine morphology metrics of cardiac signal segments that are correlated to the stability, slope content, and/or frequency content of the cardiac signal segment(s). The morphology metrics may be compared to criteria for detecting asystole or for detecting VT/VF for enabling therapy delivery circuit 84 to deliver an appropriate cardiac pacing and/or CV/DF shock therapy in response to an arrhythmia detection.

In some examples, arrhythmia detection circuit 92 may include comparators and counters for counting RRIs determined by timing circuit 90 from ventricular sensed event signals received from sensing channel 83 and/or sensing channel 85 that fall into various rate detection zones for determining a ventricular rate or performing other rate- or interval-based assessment of ventricular sensed event signals for detecting and discriminating VT and VF. For example, arrhythmia detection circuit 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter. The VF detection interval threshold may be set to 300 to 350 milliseconds (ms), as an example. For instance, if the VF detection interval is set to 320 ms, RRIs that are less than 320 ms are counted by the VF interval counter. When VT detection is enabled, the VT detection interval may be programmed to be in the range of 350 to 420 ms, or 400 ms as an example. RRIs that are less than the VT detection interval but greater than or equal to the VF detection interval may be counted by a VT interval counter. VT or VF may be detected when the respective VT or VF interval counter (or a combined VT/VF interval counter) reaches a threshold number of intervals to detect (NID).

As an example, the NID to detect VT may require that the VT interval counter reaches 18 VT intervals, 24 VT intervals, 32 VT intervals or other selected NID. In some examples, the VT intervals may be required to be consecutive intervals, e.g., 18 out of 18, 24 out of 24, or 32 out of 32 or 100 out of the most recent 100 consecutive RRIs. The NID required to detect VF may be programmed to a threshold number of X VF intervals out of Y consecutive RRIs. For instance, the NID required to detect VF may be 18 VF intervals out of the most recent 24 consecutive RRIs, 30 VF intervals out 40 consecutive RRIs, or as high as 120 VF intervals out of 160 consecutive RRIs as examples. When a VT or VF interval counter reaches a respective NID, a ventricular tachyarrhythmia may be detected by arrhythmia detection circuit 92. The NID may be programmable and range from as low as 12 to as high as 120, with no limitation intended. VT or VF intervals may reach a respective NID when detected consecutively or non-consecutively out of a specified number of most recent RRIs. In some cases, a combined VT/VF interval counter may count both VT and VF intervals and detect a tachyarrhythmia episode based on the fastest intervals detected when a specified NID is reached.

Arrhythmia detection circuit 92 may be configured to perform other signal analysis for determining if other detection criteria are satisfied before detecting VT or VF based on an NID being reached, such as R-wave morphology criteria, onset criteria, stability criteria and noise and oversensing rejection criteria. To support these additional analyses, sensing circuit 86 may pass a digitized ECG signal to control circuit 80, e.g., from morphology signal channel 87, for morphology analysis performed by arrhythmia detection circuit 92 for detecting and discriminating heart rhythms. A cardiac electrical signal received by the morphology signal channel 87 (and/or sensing channel 83 and/or sensing channel 85) may be passed through a filter and amplifier, provided to a multiplexer and thereafter converted to a multi-bit digital signal by an analog-to-digital converter, all included in sensing circuit 86, for storage in memory 82. Memory 82 may include one or more circulating buffers to temporarily store digital cardiac signal segments for analysis performed by control circuit 80. Control circuit 80 may be a microprocessor-based controller, which may include HSRs, that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves.

Therapy delivery circuit 84 includes at least one charging circuit 94, including one or more charge storage devices such as one or more high voltage capacitors for generating high voltage shock pulses for treating VT/VF. Charging circuit 94 may include one or more low voltage capacitors for generating relatively lower voltage pulses, e.g., for cardiac pacing therapies. Therapy delivery circuit 84 may include switching circuitry 95 that controls when the charge storage device(s) are discharged through an output circuit 96 across a selected pacing electrode vector or CV/DF shock vector.

In response to detecting VT/VF, control circuit 80 may schedule a therapy and control therapy delivery circuit 84 to generate and deliver the therapy, such as ATP and/or CV/DF shock(s). Therapy can be generated by initiating charging of high voltage capacitors of charging circuit 94. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit 96 of therapy delivery circuit 84 via a control bus. The output circuit 96 may include an output capacitor through which the charged high voltage capacitor is discharged via switching circuitry, e.g., an H-bridge, which determines the electrodes used for delivering the cardioversion or defibrillation pulse and the pulse wave shape. Therapy delivery circuit may be configured to deliver electrical stimulation pulses for inducing tachyarrhythmia, e.g., T-wave shocks or trains of induction pulses, upon receiving a programming command from external device 40 (FIG. 1A) during ICD implant or follow-up testing procedures.

In some examples, the high voltage therapy circuit configured to deliver CV/DF shock pulses can be controlled by control circuit 80 to deliver pacing pulses, e.g., for delivering ATP, post shock pacing pulses, bradycardia pacing pulses or asystole pacing pulses. Therapy delivery circuit 84 may be configured to generate and deliver cardiac pacing pulses using the high voltage capacitor(s) that are chargeable to a shock voltage amplitude by charging the high voltage capacitor(s) to a relatively lower voltage corresponding to a cardiac pacing pulse amplitude for capturing and pacing the ventricular myocardium. Therapy delivery circuit 84 may include a low voltage therapy circuit including one or more separate or shared charging circuits, switch circuits and output circuits for generating and delivering relatively lower voltage pacing pulses for a variety of pacing needs. Charging of capacitors to a programmed pulse amplitude and discharging of the capacitors for a programmed pulse width may be performed by therapy delivery circuit 84 according to control signals received from control circuit 80 for delivering cardiac pacing pulses. As described above, timing circuit 90 may include various timers or counters that control when cardiac pacing pulses are delivered. The microprocessor of control circuit 80 may set the amplitude, pulse width, polarity or other characteristics of cardiac pacing pulses, which may be based on programmed values stored in memory 82.

Control parameters utilized by control circuit 80 for sensing cardiac event signals, detecting arrhythmias, and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40.

Figure 4:
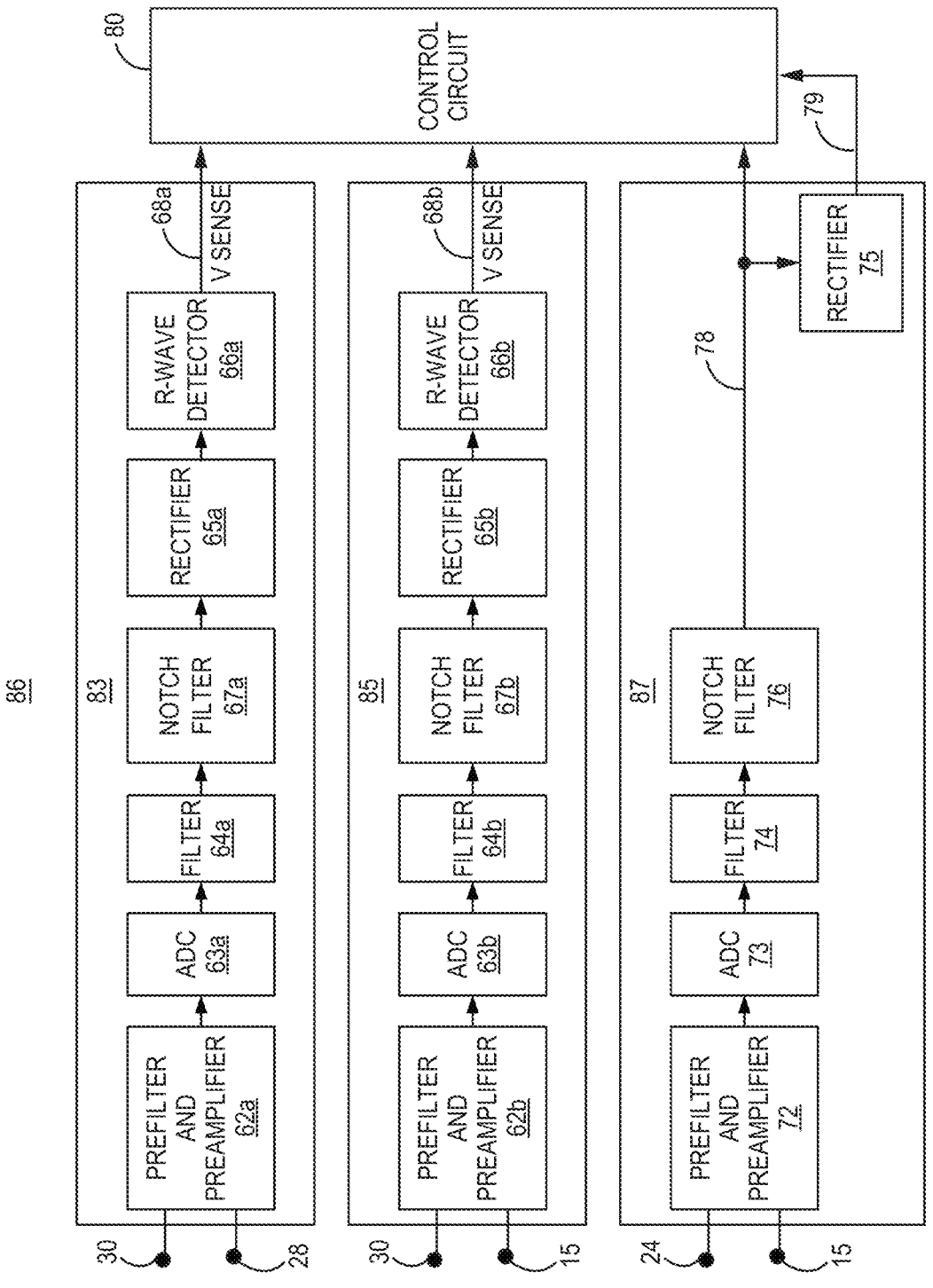
FIG. 4 is a conceptual diagram of circuitry that may be included in a sensing circuit of the ICD shown in FIG. 3 according to one example.

FIG. 4 is a conceptual diagram of circuitry that may be included in sensing circuit 86 shown in FIG. 3 according to one example. Sensing circuit 86 may include a first sensing channel 83, second sensing channel 85 and morphology signal channel 87 according to one example. First sensing channel 83 and second sensing channel 85 may each be selectively coupled via switching circuitry included in sensing circuit 86 to a respective sensing electrode vector including at least one electrode carried by extra-cardiovascular lead 16. First sensing channel 83 may be coupled to a first sensing electrode vector for receiving a first cardiac electrical signal, and second sensing channel 85 may be coupled to a second sensing electrode vector, different than the first sensing electrode vector for receiving a second cardiac electrical signal, different than the first cardiac electrical signal. In some examples, first sensing channel 83 may be coupled to a sensing electrode vector that is a short bipole, having a relatively shorter inter-electrode distance than the sensing electrode vector coupled to the second sensing channel 85 or to morphology signal channel 87. In the example shown, the first sensing channel 83 is coupled to pace/sense electrodes 28 and 30 carried by lead 16. In some examples, first sensing channel 83 may be coupled to a sensing electrode vector that is approximately vertical (when the patient is in an upright position) or approximately aligned with the cardiac axis to increase the likelihood of a relatively high R-wave signal amplitude relative to the P-wave signal amplitude. A relatively short inter-electrode distance, e.g., between electrodes 28 and 30 carried by lead 16, may be relatively less likely to be contaminated by skeletal muscle myopotential noise, EMI or other non-cardiac noise compared to a relatively longer inter-electrode distance but may have greater variability in R-wave signal strength compared to a relatively longer inter-electrode distance.

The second sensing channel 85 may be coupled to a second sensing electrode vector that is a short bipole or a relatively longer bipole compared to the first sensing electrode vector. The second sensing electrode vector may also be generally vertical or aligned with the cardiac axis. However, the second sensing electrode vector may be orthogonal or transverse relative to the first sensing electrode vector in other examples. In the example shown, the second sensing channel 85 is coupled to pace/sense electrode 30 and housing 15 such that it is a relatively longer bipole that is substantially transverse to the sensing electrode vector coupled to the first sensing channel 83. In other examples, the first or second sensing channels may be coupled to either of pace/sense electrodes 28 or 30 paired with housing 15, either of pace/sense electrodes 28 or 30 paired with coil electrode 24, or either of pace sense electrodes 28 or 30 paired with coil electrode 26, as long as at least one electrode is different between the two sensing electrode vectors. In further examples, either or both of first or second sensing channels 83 or 85 may be coupled to a sensing electrode vector that does not necessarily include one of pace/sense electrodes 28 or 30. For example, a sensing electrode vector may be coupled to sensing channel 83 or sensing channel 85 that includes one or both of coil electrodes 24 or 26 and/or housing 15.

Sensing circuit 86 may include a morphology signal channel 87 for sensing a third cardiac electrical signal. For instance, morphology signal channel 87 may receive a raw cardiac electrical signal from a third sensing electrode vector, for example from a vector that includes one electrode 24, 26, 28 or 30 carried by lead 16 paired with housing 15. Morphology signal channel 87 may be selectively coupled to a relatively long bipole having an inter-electrode distance or spacing that is greater than the sensing electrode vector coupled to first sensing channel 83 and/or second sensing channel 85 in some examples. The third sensing electrode vector may be, but not necessarily, approximately orthogonal to at least one of the first channel sensing electrode vector or the second channel sensing electrode vector. In the example shown, coil electrode 24 and housing 15 may be coupled to morphology signal channel 85 to provide the third sensed cardiac electrical signal. The third cardiac electrical signal received by morphology signal channel 87 may be used by control circuit 80 for morphology analysis to determine when morphology-based tachyarrhythmia detection criteria are met. In some examples, the sensing electrode vector coupled to morphology signal channel 87 may provide a relatively far-field or more global cardiac signal compared to a relatively shorter bipole that may be coupled to the first sensing channel 83 or the second sensing channel 85. In other examples, any vector selected from the available electrodes, e.g., electrodes 24, 26, 28, 30 and/or housing 15, may be included in a sensing electrode vector coupled to morphology signal channel 87. The sensing electrode vectors coupled to first sensing channel 83 and second sensing channel 85 and, at least in some examples, morphology signal channel 87 may be different sensing electrode vectors, which may have no common electrodes or only one common electrode but not both electrodes in common between the different sensing electrode vectors. In other examples, however, the sensing electrode vector coupled to one of the first sensing channel 83 or the second sensing channel 85 may be the same sensing electrode vector coupled to the morphology signal channel 87. In this case, a sensing channel 83 or 85 and the morphology signal channel 87 may be combined or include shared components such that a morphology signal and ventricular sensed event signals may be output to control circuit 80 from one sensing channel.

The first sensing channel 83 and the second sensing channel 85 may each receive a cardiac electrical signal for sensing ventricular event signals in response to the cardiac electrical signal crossing an R-wave sensing threshold. The morphology signal channel 87 may receive a third cardiac electrical signal for passing a multi-bit digital ECG signal to control circuit 80 for morphology analysis. In the illustrative example shown in FIG. 4, the signals received by first sensing channel 83, second sensing channel 85 and morphology signal channel 87 are provided as differential input signals to a pre-filter and pre-amplifier 62a, 62b, and 72, respectively. Non-physiological high frequency and DC signals may be filtered by a low pass or bandpass filter included in each of pre-filter and pre-amplifiers 62a, 62b and 72, and high voltage signals may be removed by protection diodes included in pre-filter and pre-amplifiers 62a, 62b and 72. Pre-filter and pre-amplifiers 62a, 62b and 72 may amplify the pre-filtered signal by a gain of between 10 and 100, and in one example a gain of 17, though each channel may have a different gain and filter bandwidth. Pre-filter and pre-amplifiers 62a, 62b and 72 may convert the differential input signal to a single-ended output signal passed to an analog-to-digital converter (ADC) 63a, 63b, and 73, respectively. Pre-filter and pre-amplifiers 62a, 62b and 72 may provide anti-alias filtering and noise reduction prior to digitization.

ADC 63a, ADC 63b and ADC 73, respectively, convert the first cardiac electrical signal, second cardiac electrical signal and third cardiac electrical signal from an analog signal to a digital bit stream, which may be sampled at 128 or 256 Hz, as examples. ADC 63a, ADC 63b and ADC 73 may be sigma-delta converters (SDC), but other types of ADCs may be used. In some examples, the outputs of ADC 63a, ADC 63b and ADC 73 may be provided to decimators (not shown), which function as digital low-pass filters that increase the resolution and reduce the sampling rate of the respective cardiac electrical signals.

The digital outputs of ADC 63a, ADC 63b and ADC 73 are each passed to respective filters 64a, 64b and 74, which may be digital bandpass filters. The bandpass filters 64a, 64b and 74 may have the same or different bandpass frequencies. For example, filters 64a and 64b may have a bandpass of approximately 10 Hz to 50 Hz, or approximately 13 Hz to 39 Hz, for passing cardiac electrical signals such as R-waves typically occurring in this frequency range. Filter 74 of the morphology signal channel 87 may have a relatively wider bandpass of approximately 2.5 to 100 Hz. In some examples, each of sensing channel 83, sensing channel 85 and morphology signal channel 87 may further include a notch filter 67a, 67b, and 76, respectively, to filter 50 Hz and 60 Hz noise signals. Each notch filter 67a, 67b, and 76 may be individually turned on or off in some examples.

The narrow bandpass and notch-filtered signal (if notch filter is turned on) in first sensing channel 83 and second sensing channel 85 is passed from respective filter 64a or filter 64b (or 67a or 67b) to rectifier 65a or rectifier 65b to produce a filtered, rectified signal output to respective R-wave detectors 66a and 66b. First sensing channel 83 includes an R-wave detector 66a for sensing ventricular event signals in response to the first cardiac electrical signal crossing an R-wave sensing threshold. Second sensing channel 85 includes an R-wave detector 66b for sensing ventricular event signals in response to the second cardiac electrical signal crossing an R-wave sensing threshold, which may be controlled separately from the R-wave sensing threshold controlled by R-wave detector 66a. R-wave detectors 66a and 66b may each include an auto-adjusting sense amplifier, comparator and/or other detection circuitry that compares the incoming filtered and rectified cardiac electrical signal to an R-wave sensing threshold and produces a ventricular sensed event signal 68a or 68b when the respective first or second cardiac electrical signal crosses the respective R-wave sensing threshold outside of a post-sense (or post-pace) blanking interval.

The R-wave sensing threshold may be a multi-level sensing threshold, e.g., as disclosed in U.S. Pat. No. 10,252,071 (Cao, et al.), incorporated herein by reference in its entirety. Briefly, the multi-level sensing threshold may have a starting sensing threshold value held for a first drop time interval, which may be equal to a tachycardia detection interval or an expected R-wave to T-wave interval, then drops, e.g., in a single step decrement, to a second sensing threshold value held until a second drop time interval expires, which may be 0.3 to 2.5 seconds long in some examples, or 0.5 to 2.5 seconds long in other examples, and can be 2.15 seconds (from the ventricular sensed event signal) in one example. After the second drop time interval, the sensing threshold drops, e.g., in a single step decrement, to a minimum sensing threshold, which may be equal to a programmed sensitivity and is also referred to herein as the "sensing floor" because it represents the minimum amplitude of the cardiac electrical signal that may be sensed as a ventricular event. The R-wave sensing thresholds used by R-wave detector 66a and 66b may each be set to a starting value based on a maximum peak amplitude of the respective first or second cardiac electrical signal determined by the R-wave detector 66a or 66b during the most recent post-sense blanking interval. In some examples, an R-wave peak tracking period may be defined as a portion of the post-sense blanking period during which the maximum peak amplitude is determined. The starting R-wave sensing threshold of each sensing channel 83 and 85 may decrease over time according to one or more stepwise drops and/or linear or non-linear decay rates until reaching the minimum sensing threshold (or until an R-wave sensing threshold crossing by the cardiac electrical signal occurs). In some instances, the R-wave sensing threshold may be adjusted to the minimum sensing threshold before the expiration of the first drop time interval or before the expiration of the second drop time interval depending on the maximum peak amplitude determined during the R-wave peak tracking period.

The techniques described herein are not limited to a specific behavior of the sensing threshold or specific R-wave sensing techniques. Instead, other decaying, stepwise adjusted or other automatically adjusted sensing thresholds may be utilized for sensing ventricular event signals from the respective first and second cardiac electrical signals. R-wave detector 66a or 66b may produce a ventricular sensed event signal 68a or 68b in response to the respective first cardiac electrical signal or second cardiac electrical signal crossing the R-wave sensing threshold. The ventricular sensed event signal 68a or 68b is passed to control circuit 80.

The wideband-filtered, digital cardiac electrical signal 78 output from morphology signal channel 87 may be passed to control circuit 80 for performing morphology-based arrhythmia detection according to the techniques disclosed herein. In some examples, the digital cardiac electrical signal 78 is passed to rectifier 75 and a rectified wideband filtered signal 79 is passed to control circuit 80 for processing and analysis. In some cases, both the filtered, non-rectified signal 78 and the rectified signal 79 are passed to control circuit 80 from morphology signal channel 87 for use in determining morphology features of the ECG signal. As described below, an n-second ECG signal segment may be buffered in memory 82 by control circuit 80 for processing and analysis for detecting asystole and tachyarrhythmia. The n-second ECG signal segment(s) analyzed by arrhythmia detection circuit 92 may undergo additional low pass, bandpass and/or high pass filtering and/or other signal processing prior to analysis for determining morphology features or other features of the ECG signal segment for arrhythmia detection.

The configuration of sensing channels 83 and 85 and morphology signal channel 87 as shown in FIG. 4 is illustrative in nature and should not be considered limiting of the techniques described herein. Sensing circuit 86 may include more or fewer components than illustrated and described in FIG. 4 and some components may be shared between sensing channels 83 and 85 and morphology signal channel 87. For example, a common cardiac electrical signal from a selected sensing electrode vector may be received by a prefilter and preamplifier circuit and ADC and subsequently be passed to a narrowband filter in one of sensing channels 83 or 85 and to a wideband filter in morphology signal channel 87. In other examples, sensing circuit 86 may include none, one or more than two sensing channels, each configured to produce a ventricular sensed event signal, and/or more than one morphology signal channel. In other examples, a wideband filtered morphology signal may be passed to control circuit 80 from one of sensing channels 83 or 85 for performing analysis of cardiac signal segments according to the techniques disclosed herein for use in detecting arrhythmia. Furthermore, the components for filtering, amplifying, digitizing, rectifying, etc. may be arranged in a different order or combination than shown in FIG. 4.

Figure 5:
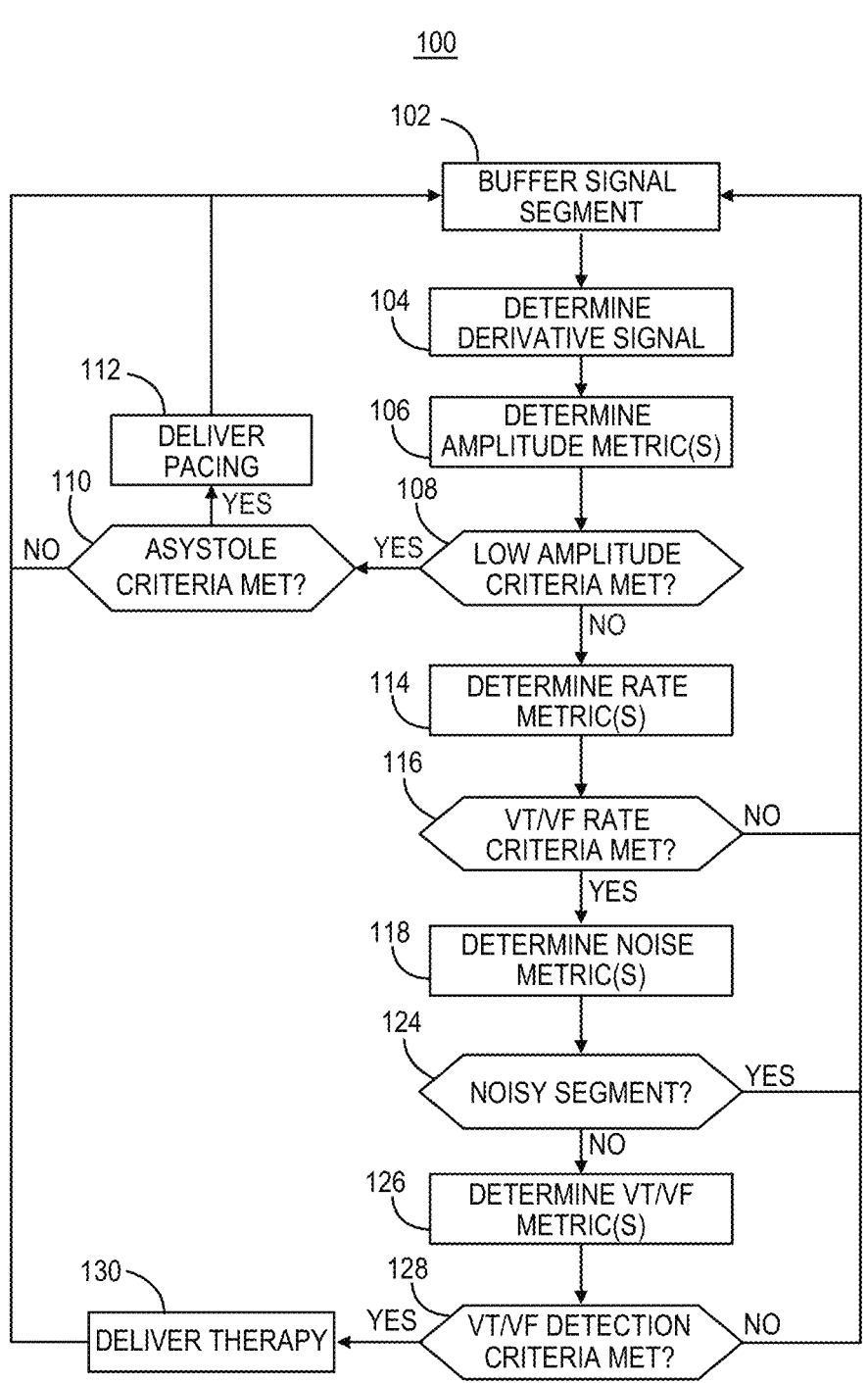
FIG. 5 is a flow chart of a method for detecting arrhythmia by an ICD according to some examples.

FIG. 5 is a flow chart 100 of a method for detecting arrhythmia by ICD 14 according to some examples. At block 102, control circuit 80 receives a cardiac electrical signal from sensing circuit 86, e.g., from morphology signal channel 87, and buffers the cardiac electrical signal in memory 82 over a predetermined n-second time interval to obtain a cardiac signal segment. The cardiac signal segment may begin and/or end independent of the timing of ventricular sensed event signals received from sensing circuit 86. In some instances, control circuit 80 may not be receiving any ventricular sensed event signals from sensing circuit 86 before or during the n-second time interval, e.g., due to undersensing of R-waves or fibrillation waves by sensing channels 83 and 85. In the illustrative examples presented herein, the cardiac signal segment is three seconds long but could be longer or shorter than three seconds. The duration of the cardiac signal segment may be 0.5 seconds to several seconds, e.g., 1 to 6 seconds, in order to include multiple ventricular cycles during high heart rates. In various examples, with no limitation intended, the time interval over which the cardiac signal segment is received may be at least four times a tachyarrhythmia detection interval, at least 8 times a tachyarrhythmia detection interval, or at least 10 times a tachyarrhythmia detection interval. The cardiac electrical signal may be sampled at a rate of 256 Hz over a three second interval to obtain 768 sample points in illustrative examples presented herein though other sampling rates and time intervals may be used.

Control circuit 80 is configured to process and analyze the cardiac electrical signal segment received from morphology signal channel 87 for detecting arrhythmias, e.g., asystole and/or VT/VF. As described below in conjunction with the flow charts and diagrams presented herein, arrhythmia detection circuit 92 may determine various parameters and metrics, e.g., parameters or metrics relating to amplitude content, frequency content, and slope content as examples, from time segments of the cardiac electrical signal received from morphology signal channel 87 for detecting arrhythmia. The cardiac electrical signal received from morphology signal channel 87 may undergo different processing, e.g., different types of filtering, by control circuit 80 for determining different parameters and metrics from the cardiac signal segments.

Control circuit 80 may determine a first derivative signal of the cardiac signal segment at block 104. The first derivative signal may be approximated as a first order difference signal by determining the difference between consecutive sample points in the cardiac signal segment without dividing by the time interval between sample points. In other examples, a second order or other higher order difference signal can be used. In still other examples control circuit 80 may determine a gradient signal, e.g., using central difference methods at block 104. Determination of a derivative signal from the cardiac electrical signal received from morphology signal channel 87 may be performed by calling upon an HSR implemented in control circuit 80. The derivative signal, which may be determined as a difference signal or gradient signal without requiring a division step, is representative of the variation in slope in the signal received from morphology signal channel 87.

Control circuit 80 may include one or more bandpass filters for filtering the derivative signal. In one example, control circuit 80 includes at least two bandpass filters for filtering the derivative signal according to two different passbands. Each bandpass filter may be implemented as an HRS filter or other hardware, firmware, or software implemented filter. In some examples, a gradient signal is determined from the cardiac signal segment by control circuit 80 using a central difference method, followed by bandpass filtering, e.g., between 1 to 35 Hz or between 3 Hz to 23 Hz or between 3 Hz and 32 Hz as examples, and determination of the first order difference signal at block 104. Control circuit 80 may subsequently rectify the bandpass filtered, derivative signal for determining parameters from the cardiac signal segment used in detecting arrhythmia. Depending on the parameter being determined from the derivative signal of the cardiac signal segment, control circuit 80 may apply different filtering of the derivative signal, e.g., different low pass and/or high pass filtering, for improving the specificity and sensitivity of arrhythmia detection based on the morphology parameter or metric being determined.

At block 106, control circuit 80 determines an amplitude metric from the derivative signal. The amplitude metric is representative of amplitudes of signal peaks identified from the derivative signal. A method for determining an amplitude metric is described below in conjunction with FIG. 6. Control circuit 80 may compare the amplitude metric to low amplitude criteria at block 108. For example, the amplitude metric may be compared to a low amplitude threshold, which may be 0.050 to 0.2 millivolts (mV) or about 0.1 mV in an example. When the amplitude metric is less than the low amplitude threshold, asystole may be present. At block 110, control circuit 80 may perform a first analysis of the cardiac signal segment for detecting asystole when the amplitude metric is less than the low amplitude threshold. Methods for performing the first analysis for determining that asystole criteria are met at block 110 are described below, e.g., in conjunction with FIG. 16. When the asystole criteria are not met at block 110, control circuit 80 may return to block 102 to buffer the next cardiac signal segment.

When asystole criteria are met, control circuit 80 may deliver at least one cardiac pacing pulse at block 112. In some examples, a cardiac pacing pulse may be delivered by therapy delivery circuit 84 when at least one cardiac signal segment meets the asystole criteria. In other examples, asystole may be detected by control circuit 80 when at least two or another threshold number of cardiac signal segments meet the asystole criteria at block 110. The number of cardiac signal segments required to meet the asystole criteria at block 110 for detecting asystole and delivering a pacing pulse may depend on the total duration of the cardiac signal segment(s). For instance, a pacing pulse may be delivered when asystole is detected to be present based on the analysis of one 3-second segment, at least two 2-second segments, at least two 3-second segments, or at least eight 0.5 second segments, as illustrative examples. In other examples, as described below in conjunction with FIG. 18, control circuit 80 may determine when an asystole condition is detected and persists for a threshold time interval. In response to the asystole condition persisting for a threshold time interval, control circuit 80 may schedule a pacing pulse that can be delivered by therapy delivery circuit 84 when a ventricular sensed event signal is not received from sensing circuit 86 by control circuit 80 after detecting the asystole and prior to delivering the pacing pulse.

When the low amplitude criteria are not met at block 108, control circuit 80 may perform a second analysis of the cardiac signal segment for detecting tachyarrhythmia. The second analysis may optionally include determining a morphology-based rate metric from the cardiac signal segment for estimating the ventricular rate during the 3-second segment. Control circuit 80 may determine a rate metric at block 114 by identifying and counting signal pulses and/or determining intervals between signal pulses that are identified by control circuit 80 based on an analysis of the amplitude of the cardiac signal segment. Techniques for determining a rate metric are described below, e.g., in conjunction with FIG. 6. Control circuit 80 may determine if VT/VF rate criteria are met at block 116 based on the rate metric. The rate metric may be compared to a threshold for determining if the ventricular rate is likely to be in a VT or VF rate zone during the 3-second time interval based on the number and/or interval(s) between signal pulses identified during the 3-second time interval. If the VT/VF rate criteria are not met, no further analysis of the cardiac signal segment may be executed in some examples. Control circuit 80 may terminate the second analysis of the cardiac signal segment for detecting VT/VF and return to block 102 to obtain the next 3-second cardiac signal segment.

Additionally or alternatively, the second analysis may optionally include a determination of whether the cardiac signal segment is a noisy segment. Control circuit 80 may be configured to determine one or more noise metrics from the cardiac signal segment at block 118. Example noise metrics that may be determined by control circuit 80 are described below in conjunction with FIGS. 9 and 10. One or more noise metrics may be compared to noisy segment criteria at block 124. Control circuit 80 may analyze the cardiac signal segment for detecting noise in order to reduce the likelihood that noise, such as skeletal muscle myopotential signals or other noise, is falsely detected as VT/VF. Example criteria that may be applied at block 124 for detecting a noisy signal segment are described below in conjunction with FIG. 11. When the cardiac signal segment is determined to be a noisy segment at block 124, control circuit 80 may return to block 102 to obtain the next cardiac signal segment. When a noisy segment is detected, control circuit 80 may terminate the second analysis of the cardiac signal segment for detecting VT/VF in some examples.

In some examples, when the rate metric meets VT/VF rate criteria at block 116 and the noise metric(s) do not meet noisy segment criteria at block 124, control circuit 80 may advance to block 126 for determining VT/VF morphology metrics from the cardiac signal segment. In other examples, control circuit 80 may determine the rate metric(s) at block 114 for comparison to rate criteria at block 116 but determining the noise metrics for comparison to noisy segment criteria at block 124 may be omitted. When VT/VF rate criteria are met at block 116 based on the rate metric(s), control circuit 80 may advance directly to block 126 to determine VT/VF morphology metrics. In another example, control circuit 80 may determine the noise metrics at block 118 for comparison to noisy segment criteria at block 124 without determining the rate metric(s) at block 114. In still other examples, the determination of the rate metric(s) at block 114 and the determination of the noise metric(s) at block 118 may both be omitted. In this case, control circuit 80 may advance directly to block 126 after determining that low amplitude criteria are not met at block 108.

Control circuit 80 may determine VT/VF morphology metrics at block 126 that represent the slope and/or frequency content of the cardiac signal segment. The VT/VF morphology metrics provide discrimination between the slope and/or frequency content of a cardiac signal segment that is likely to include a VT/VF rhythm (e.g., R-waves occurring at a fast rate or fibrillation waves) and a cardiac signal segment that is unlikely to include a VT/VF rhythm, e.g., as further described in conjunction with FIGS. 13-15. Control circuit 80 may compare the VT/VF morphology metrics to VT/VF detection criteria at block 128. Methods for determining VT/VF morphology metrics and determining when VT/VF detection criteria are met are described below in conjunction with FIG. 12.

When control circuit 80 determines that the VT/VF detection criteria are not met at block 128, control circuit 80 may return to block 102 to obtain the next cardiac signal segment. In some examples, control circuit 80 may count consecutively or non-consecutively detected VT/VF signal segments. VT/VF detection criteria applied at block 128 may require that two or more consecutive cardiac signal segments or a threshold number X out of Y cardiac signal segments, e.g., two out three segments, be determined to be VT/VF segments before detecting VT/VF. When the VT/VF morphology metrics for the current cardiac signal segment do not meet VT/VF segment detection criteria at block 128, the count of VT/VF segments may be reset to zero in some examples or otherwise used to update an X of Y counter for detecting a threshold number of non-consecutive VT/VF segments.

In response to the VT/VF detection criteria being met at block 128, therapy delivery circuit 84 may deliver tachyarrhythmia therapy at block 130. The therapy delivered at block 130 may include one or more ATP sequences, which may be performed before and/or during charging of high voltage capacitor(s) for generating a CV/DF shock pulse. ATP may be delivered before a shock pulse in an attempt to terminate the VT/VF without requiring shock delivery. Control circuit 80 may determine that the VT/VF is still present in a cardiac signal segment (and/or based on ventricular sensed event signals) after ATP delivery and subsequently deliver a CV/DF shock when ATP does not terminate the VT/VF. In other examples, control circuit 80 may charge the high voltage capacitor(s) in response to detecting VT/VF at block 128 without delivering ATP. A CV/DF shock may be delivered at block 130 one or more times until VT/VF is no longer detected by control circuit 80. After shock delivery, control circuit 80 may return to block 102 to obtain the next cardiac signal segment.

Prior to delivering a shock therapy at block 130, control circuit 80 may determine the VT/VF morphology metrics from one or more cardiac signal segments, e.g., during high voltage capacitor charging, for confirming that VT/VF is still being detected prior to shock delivery. In some examples, when one or more cardiac signal segments are determined to be non-VT/VF segments during capacitor charging based on the VT/VF morphology metrics, control circuit 80 may detect termination of the detected VT/VF rhythm, cancel the CV/DF shock, and return to block 102 to obtain the next cardiac signal segment. For instance, when less than 2 out of the most recent 3 cardiac signal segments or less than 5 out of the most recent 8 cardiac signal segments are VT/VF signal segments, control circuit 80 may determine that the detected VT/VF rhythm is terminated, e.g., either spontaneously or by ATP therapy, prior to shock delivery.

Figure 6:
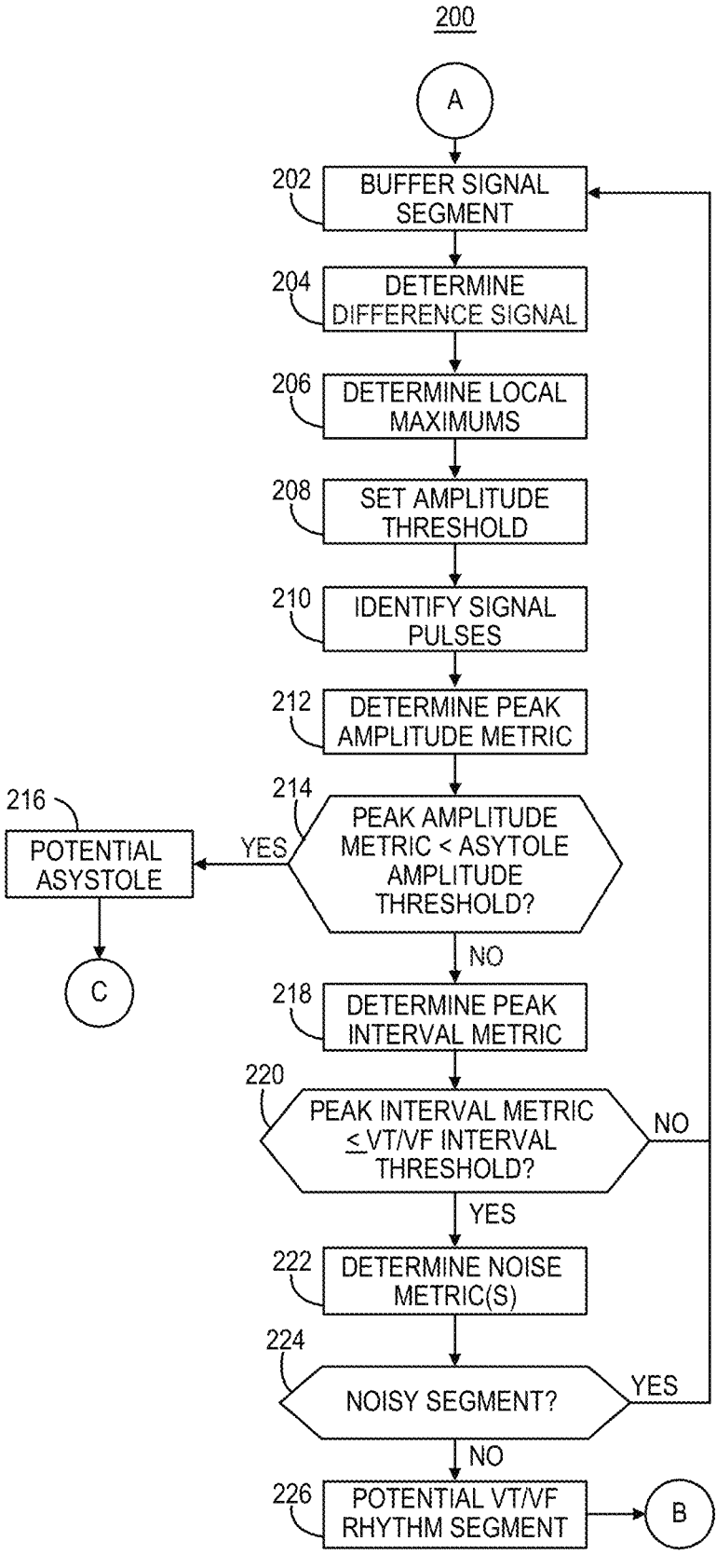
FIG. 6 is a flow chart of a method for performing morphology analysis for detecting asystole and VT/VF according to another example.

FIG. 6 is a flow chart 200 of a method for performing cardiac signal analysis for detecting asystole and VT/VF according to another example. At block 202, control circuit 80 buffers a cardiac signal segment in memory 82. The cardiac signal segment may be received from morphology signal channel 87 and may be three seconds in duration in some examples. While the illustrative examples presented herein refer to an analysis of cardiac signal segments obtained from the morphology signal channel 87, it is to be understood that in other examples, a cardiac signal segment that is analyzed for detecting arrhythmia according to the techniques disclosed herein may be obtained from sensing channel 83 or sensing channel 85. For the sake of illustration, the cardiac signal segment is described in conjunction with FIG. 6 as being three seconds long. It is to be understood that the signal segment may be longer or shorter than three seconds in other examples.

At block 204, control circuit 80 determines a first derivative signal as described above, which may be estimated as a first order difference signal by determining the difference between consecutively sampled points. The derivative signal can be rectified for facilitating analysis of the cardiac signal segment for identifying signal pulses that may be associated with ventricular activity for use in determining a rate metric. As described above, prior to determining the rectified difference signal, a gradient signal may be determined from the cardiac signal segment, which may be bandpass filtered before determining the first order difference signal. Control circuit 80 may determine a rate metric from the rectified, derivative signal when the low amplitude criteria are not met by the rectified, derivative signal (e.g., estimated as a first order difference signal). As described above in conjunction with FIG. 5, when low amplitude criteria are met, an absence of ventricular activity or asystole may be suspected. When low amplitude criteria are not met, ventricular event signals are likely present in the cardiac signal segment, and a rate metric may be derived from the cardiac signal segment that is expected to be representative of the rate of ventricular event signals, e.g., R-waves or fibrillation waves, in the cardiac signal segment. The rate metric derived from the cardiac signal segment may be determined for comparison to VT/VF rate criteria as described above in conjunction with FIG. 5.

One method for determining an amplitude metric begins by determining local maximums at block 206. At block 206, control circuit 80 may divide the cardiac signal segment, which is now a rectified, difference signal, into multiple subsegments for determining local maximums of the cardiac signal segment. Each subsegment may be 0.25 to 1.0 seconds long in some examples. In the example of a 3-second cardiac signal segment, control circuit 80 may divide the segment into four 0.75 second subsegments that each include 192 sample points when the sampling rate is 256 Hz.

Control circuit 80 determines local maximums from each sub-segment of the cardiac signal segment at block 206. In some examples, the greatest local maximum of the cardiac signal segment is identified and compared to each of the other local maximums. When a local maximum for a given subsegment is less than 30%, 20%, 10% or other selected percentage or fraction of the greatest local maximum, control circuit 80 may replace the local maximum for that subsegment with the greatest local maximum. At block 208, the local maximums are used to establish a signal pulse amplitude threshold. Control circuit 80 may determine a mean, median, maximum, minimum or other representative amplitude from the local maximums and set the signal pulse amplitude threshold to a percentage of the representative amplitude in some examples. For instance, control circuit 80 may set the signal pulse amplitude threshold to 25% of the mean amplitude of the four local maximums determined from the four subsegments of the cardiac signal segment.

At block 210, control circuit 80 identifies each signal pulse during the cardiac signal segment that has an amplitude greater than the signal pulse amplitude threshold. In some examples, control circuit 80 may identify signal pulse peaks of the rectified difference signal that are greater than the signal pulse amplitude threshold and separated by at least a threshold time interval from other signal pulse peaks. For example, starting from the beginning of the cardiac signal segment, the first earliest signal pulse that is greater than the signal pulse amplitude threshold may be identified. The next earliest signal pulse that is greater than the signal pulse amplitude threshold and has a peak that is at least 100 ms later than the first signal pulse peak may be identified and so on. In this way, the earliest signal pulse that is at least 100 ms after the most recently identified signal pulse is identified as a signal pulse. In other examples, if more than one signal pulse peak that is greater than the signal pulse amplitude threshold occur within 100 ms of each other, the signal pulse peak having the greatest amplitude may be identified as a signal pulse peak and other signal pulse peaks that are within 100 ms of the identified signal pulse peak may be ignored. In this way, a single R-wave or fibrillation wave that may have more than one peak is not identified twice. Example techniques for identifying signal pulses are described below in conjunction with FIGS. 7A-8B. The signal pulses that are identified based on the amplitude threshold and are spaced at least a minimum time interval apart may be representative of ventricular event signals, e.g., R-waves or fibrillation waves, if present in the cardiac signal segment.

Control circuit 80 may determine a peak amplitude metric from the identified signal pulses at block 212. Control circuit 80 may determine the peak amplitude metric by determining a mean, median, maximum, minimum, range, and/or standard deviation or other representative value(s) of the peak amplitudes of the signal pulses identified at block 210. At block 214, control circuit 80 may compare the peak amplitude metric to low amplitude criteria. Control circuit 80 may determine that low amplitude criteria are met at block 214 when the peak amplitude metric is less than an amplitude threshold. In an example, control circuit 80 may determine that low amplitude criteria are met at block 214 when the mean peak amplitude of the identified signal pulses in the rectified difference signal of the cardiac signal segment is less than an asystole amplitude threshold. The asystole amplitude threshold may be a predetermined or programmable threshold value and may be between 0.05 and 0.2 millivolts, as examples. In one example the amplitude threshold is 0.1 millivolt but other thresholds may be selected. The amplitude threshold may be based on the minimum expected amplitude of fibrillation waves. The amplitude threshold may be referred to as an "asystole amplitude threshold" because the amplitude threshold may represent a minimum amplitude of the cardiac signal segment when ventricular activity is present, e.g., R-waves or fibrillation waves. When the peak amplitude metric is less than the asystole amplitude threshold, ventricular asystole may be present.

When control circuit 80 determines that the low amplitude criteria are met at block 214, ventricular event signals may be absent from the cardiac signal segment. The cardiac signal segment may be identified as potential asystole at block 216. Control circuit 80 may advance to the process of FIG. 16 (as shown by connector "C") to perform an asystole analysis of the cardiac signal segment for detecting asystole.

When control circuit 80 determines that the low amplitude criteria are not met at block 214, the signal pulses identified at block 210 may correspond to ventricular event signals. Control circuit 80 may perform a VT/VF analysis of the cardiac signal segment for detecting VT/VF. In some examples, control circuit 80 may advance directly to the flow chart of FIG. 12 (as indicated by connector "B") to determine morphology metrics of the cardiac signal segment that are compared to VT/VF detection criteria. In the example of FIG. 6, control circuit 80 may start the VT/VF analysis by first verifying that a ventricular rate estimate determined from the cardiac signal segment is faster than a VT/VF rate threshold and/or that the cardiac signal segment is not a noisy segment.

At block 218, control circuit 80 may determine peak intervals as the time intervals between the peaks of consecutive signal pulses identified at block 210. Control circuit 80 may determine one or more peak interval metrics at block 218 by determining a mean, median, maximum, minimum, range, standard deviation, and/or other representative value of the peak intervals. The peak interval metric may be correlated to the rate of ventricular event signals in the cardiac signal segment and provide evidence for detecting VT/VF without requiring or in the absence of ventricular sensed event signals from sensing circuit 86 (e.g., from sensing channels 83 and 85). Additionally or alternatively, control circuit 80 may determine a count of the signal peaks identified in the cardiac signal segment. The identified signal peaks are at least a threshold time interval apart and, based on the time duration of the cardiac signal segment, a count of the identified signal peaks is an indication of the average rate of signal pulses during the cardiac signal segment. A metric of the peak intervals and/or the count of identified signal pulses may be compared to VT/VF rate criteria at block 220.

At block 220, control circuit 80 may determine that VT/VF rate criteria are met when the peak interval metric is less than a VT/VF interval threshold. The VT/VF interval threshold may be programmable and may be between 220 and 500 ms and is 260 ms as an example. In one example, the peak interval metric is determined as the mean of all peak intervals at block 218. When the mean peak interval is greater than or equal to 260 ms (or any other selected VT/VF interval threshold), control circuit 80 may determine that the cardiac signal segment is not VT/VF and return to block 202 to obtain the next cardiac signal segment ("no" branch of block 220). Control circuit 80 may terminate the analysis of the cardiac signal segment for detecting VT/VF in response to the peak interval metric being greater than the VT/VF interval threshold.

When control circuit 80 determines that the VT/VF rate criteria are met at block 220, e.g., based on the peak interval metric being less than a VT/VF interval threshold, control circuit 80 may continue the cardiac signal segment analysis for detecting VT/VF by advancing to block 222. At block 222, control circuit 80 may determine one or more noise metrics. Example noise metrics that may be determined at block 222 are described below in conjunction with FIGS. 9 and 10 and may include a mean rectified amplitude of the cardiac signal segment, a normalized mean rectified amplitude, a muscle noise pulse count and/or a mean period of the cardiac signal segment. Noisy segment criteria that may be applied to the noise metrics at block 224 are described below in conjunction with FIG. 11. When noisy segment criteria are met, control circuit 80 may terminate the analysis of the cardiac signal segment for detecting VT/VF and return to block 202 to obtain the next cardiac signal segment. In some examples, blocks 222 and 224 may be optional. Control circuit 80 may determine that the cardiac signal segment is a potential VT/VF rhythm segment at block 226 based on the peak interval metric determined from processing and analysis of the cardiac signal segment being less than the VT/VF interval threshold and advance to the flow chart of FIG. 12 (as indicated by connector "B") for determining if the cardiac signal segment meets VT/VF detection criteria.

Figure 7A:
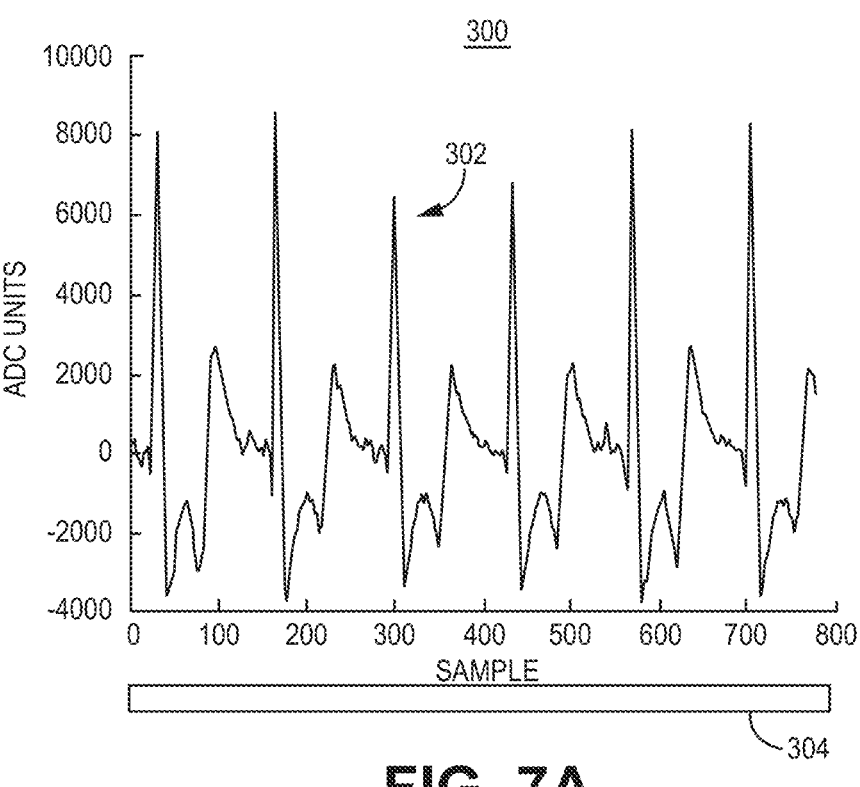
FIG. 7A is a diagram of an example cardiac signal segment that may be analyzed for detecting VT/VF.
Figure 7B:
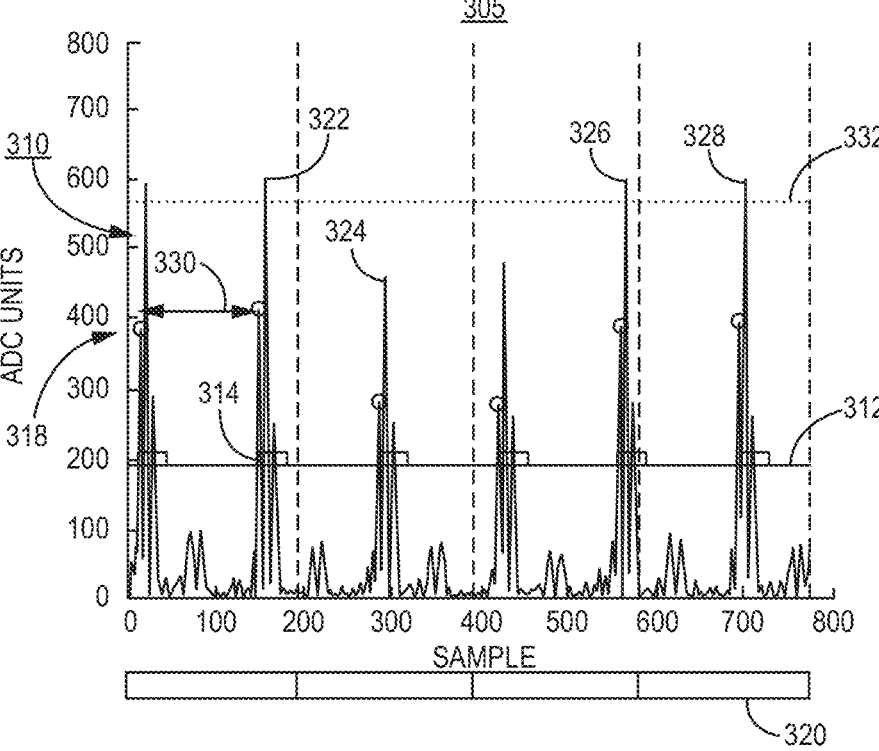
FIG. 7B is a diagram of a rectified, difference signal determined from the cardiac signal segment of FIG. 7A.

FIG. 7A is a diagram 300 of an example cardiac signal segment 302 that may be analyzed for detecting an arrhythmia. FIG. 7B is a diagram 305 of a rectified, difference signal 310 determined from the cardiac signal segment of FIG. 7A that may be analyzed for detecting arrhythmia according to the techniques disclosed herein. In the example of FIG. 7A, the cardiac electrical signal 302 is obtained during a non-VT/VF rhythm, e.g., a supraventricular rhythm which may be a normal sinus rhythm such as sinus tachycardia. The cardiac signal segment 302 of FIG. 7A is acquired over time segment 304, e.g., a three second time segment, and sampled at a 256 Hz sampling rate in this example. The cardiac signal segment 302 may be a bandpass and notch filtered signal segment received from morphology signal channel 87. Control circuit 80 may be configured to determine the difference signal, e.g., by passing the cardiac signal segment 302 through a first order difference filter. The cardiac signal received from morphology signal channel 87 may be filtered by a bandpass filter, e.g., 3-23 Hz bandpass filter, and subsequently passed through a difference filter and rectified to obtain the rectified difference signal 310 of FIG. 7B. In some examples, a gradient signal is determined from the cardiac signal received from morphology signal channel 87, which may be subsequently bandpass filtered prior to determining the rectified, difference signal from the cardiac signal 302 over time segment 304.

In some examples, zero crossings of the first order difference signal may be set prior to rectification by identifying consecutive sample points of the difference signal having opposite polarity. For example, a positive sample point followed by a negative sample point may be identified as a zero crossing, or a negative sample point followed by a positive sample point may be identified as a zero crossing. Control circuit 80 may compare the absolute values of the two signal sample points identified as a zero crossing. The sample point of the difference signal having the smaller absolute value amplitude may be set to zero amplitude to clearly demarcate each zero crossing of the difference signal.

In this way, two consecutive zero crossings define a signal pulse occurring between the two zero crossings.

Control circuit 80 may determine a peak amplitude metric and a peak interval metric from the rectified difference signal 310 of FIG. 7B. Control circuit 80 may establish a signal pulse amplitude threshold 312 used for identifying signal pulses in the difference signal 310. In some examples, the control circuit 80 divides the time segment 304 into multiple subsegments 320, shown as four subsegments in the example of FIG. 7B. Control circuit 80 determines the local maximum amplitude 322, 324, 326 and 328 of each subsegment 320. If a local maximum amplitude is less than a percentage, e.g., less than 30%, less than 25%, or less than 20% of the overall maximum peak amplitude 322 of the entire difference signal 310 over time segment 304, control circuit 80 may set the local maximum amplitude to be equal to the overall maximum peak amplitude. Control circuit 80 may determine a signal pulse amplitude threshold 312 as a predetermined percentage, e.g., 15 to 50% or about one-sixth to one-half of the average of the local maximum amplitudes 322, 324, 326 and 328 of the subsegments 320. In the example shown, the signal pulse amplitude threshold 312 is determined as one-third of the mean amplitude 332 of the four local maximum amplitudes 322, 324, 326 and 328.

Control circuit 80 may identify each signal pulse of the difference signal 310 having an amplitude that is greater than the signal pulse amplitude threshold 312 and is separated by a minimum predetermined number of sample points, e.g., 25 sample points or about 97.6 seconds as an example, shown by minimum time interval 314. The maximum peaks 318 of signal pulses having an amplitude greater than amplitude threshold 312 and separated by a minimum time interval 314 are each marked by a circle in FIG. 7B to indicate signal pulses identified by control circuit 80. These identified signal pulses may correspond to ventricular event signals, e.g., R-waves or fibrillation waves, and are used for determining an estimate of the ventricular rate from the 3-second segment 304.

Control circuit 80 may determine various metrics from the difference signal 310 spanning the time segment 304 (of the entire cardiac signal segment 302) based on the amplitudes and intervals between the identified signal pulse peaks 318 for detecting VT/VF without requiring ventricular sensed event signals from sensing circuit 86. For example, at block 106 of FIG. 5 or block 212 of FIG. 6, control circuit 80 may determine a peak amplitude metric as a representative amplitude of all of the identified signal pulse peaks 318. The representative amplitude is determined as a mean amplitude of all of the identified signal pulse peaks 318 in some examples. Control circuit 80 may additionally or alternatively determine a peak amplitude metric by determining the maximum peak amplitude 322 of all the identified signal pulse peaks 318. In various examples, control circuit 80 may determine one or more peak amplitude metrics from the identified signal peaks by determining a mean, median, maximum, minimum, range, and/or standard deviation or other metric of the identified signal pulse peaks 318. As described above, the peak amplitude metric may be used for determining whether to perform a first analysis of the cardiac signal segment for detecting asystole or a second analysis of the cardiac signal segment for detecting VT/VF. The peak amplitude metric(s) may be correlated to the likelihood of ventricular activity being present in the cardiac signal segment 304. The peak amplitude metric(s) may additionally be used during the first and/or second analyses for detecting asystole or VT/VF, respectively, in some examples.

At block 114 of FIG. 5 or block 218 of FIG. 6, control circuit 80 may determine a rate metric by determining the peak intervals 330 as the time intervals between consecutively identified signal pulse peaks 318. Control circuit 80 may determine the rate metric as the mean of all peak intervals determined during the cardiac signal segment. Control circuit 80 may additionally or alternatively determine a median, minimum, maximum, standard deviation, range and/or other metric of the peak intervals 330. As described above in conjunction with FIG. 6, the peak interval metric may be compared to an interval threshold corresponding to a VT/VF rate for detecting VT/VF in some examples. In the example shown, the mean peak interval is approximately 550 ms corresponding to a heart rate of about 110 beats per minute, which is slower than a VT/VF rate. When the peak interval metric is greater than or equal to a VT/VF interval threshold, e.g., 220 to 350 ms or 260 ms as an example, the cardiac signal segment is not likely to include VT/VF. Control circuit 80 may advance to the next cardiac signal segment for processing and analysis. The VT/VF interval threshold may correspond to the VT interval zone or the VF interval zone, which may be programmable by a user.

In some examples, in addition to or alternatively to determining the peak interval metric, the number of signal pulses identified in the cardiac signal segment may be counted. The count of identified signal pulses may be compared to a threshold value that corresponds to a VT/VF threshold rate of ventricular event signals occurring within the time segment 304. For example, if the VT/VF interval threshold is 260 ms corresponding to a rate of about 230 beats per minute, and time segment 304 is 3 seconds, a count of at least 12 signal pulses identified in the cardiac signal segment would be required to meet VT/VF rate criteria, e.g., at block 116 of FIG. 5. In the example of FIG. 7B, six signal pulses are identified as marked by signal pulse peaks 318, which is fewer than the threshold count of 12 that would be present if the signal pulses are occurring at the VT/VF threshold rate within the 3-second time segment 304.

Figure 8A:
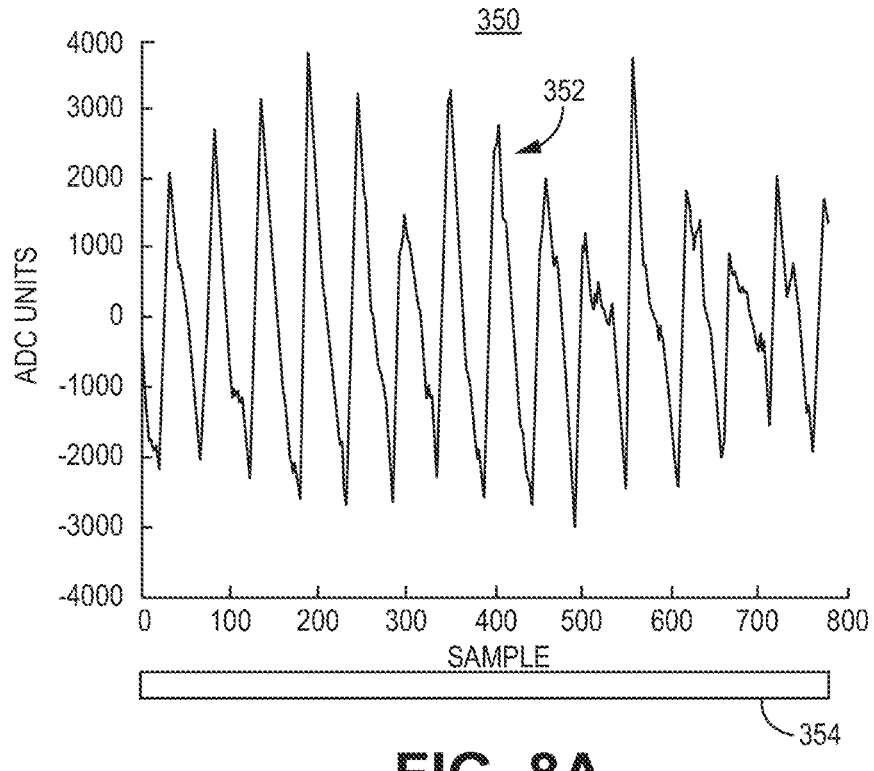
FIG. 8A is a diagram of another example of a cardiac signal segment that may be analyzed for detecting VT/VF.
Figure 8B:
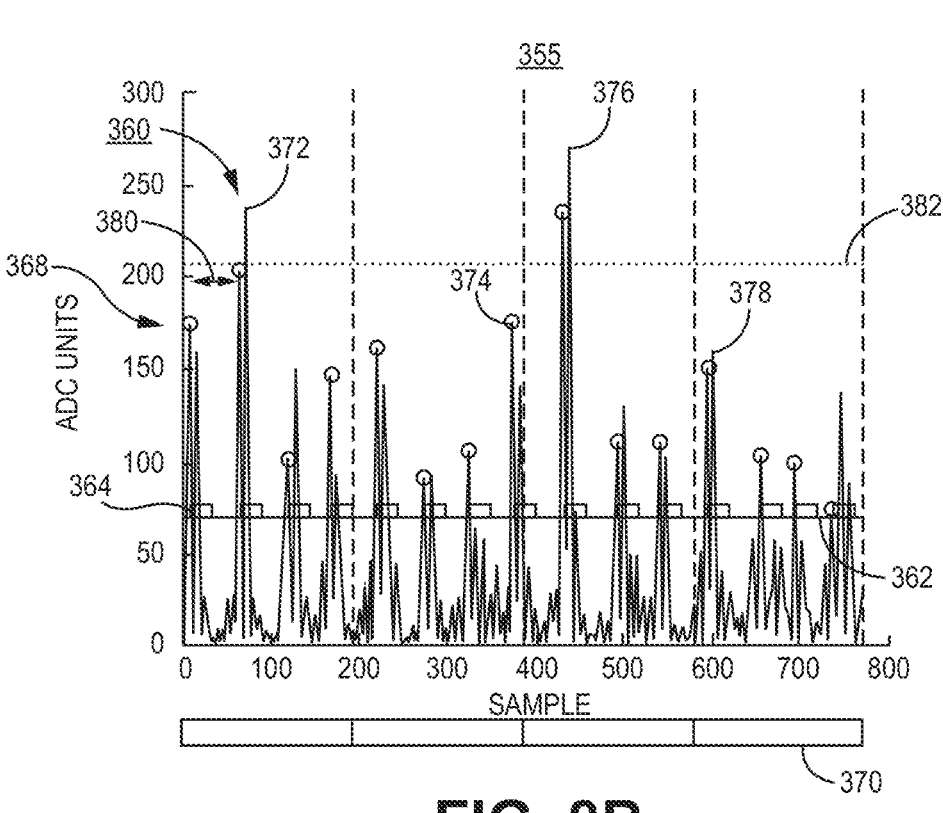
FIG. 8B is a diagram of a rectified, difference signal determined from the cardiac signal segment of FIG. 8A.

FIG. 8A is a diagram 350 of another example of a cardiac signal segment 352 that may be analyzed for detecting arrhythmia according to the techniques disclosed herein. FIG. 8B is a diagram 355 of a rectified, difference signal 360 determined from the cardiac signal segment of FIG. 8A. In this example, the cardiac signal segment 352 is acquired during VF over the predetermined time segment 354. Control circuit 80 determines the rectified difference signal 360 as shown in FIG. 8B and identifies signal pulse peaks 368 using the techniques described above in conjunction with FIG. 7B. Signal pulse peaks 368 may be identified as the signal peaks having an amplitude greater than a signal pulse amplitude threshold 362 and are separated by a minimum time interval 364, e.g., about 100 ms. The signal pulse amplitude threshold 362 may be determined by control circuit 80 as one-third (or other fraction or percentage) of the mean 382 of the local maximum peaks 372, 374, 376 and 378 of each of the subsegments 370, e.g., as generally described above in conjunction with FIG. 7B.

Control circuit 80 may determine a peak amplitude metric as the mean peak amplitude of all identified signal pulse peaks 368. Control circuit 80 may determine a peak interval metric as an estimate of ventricular event intervals (corresponding to a ventricular rate estimate) during time segment 354. The peak interval metric may be determined as the mean of all peak intervals 380 determined by control circuit 80 as the time intervals between consecutive signal pulse peaks 368. As described above, control circuit 80 may determine one or more peak amplitude metrics and/or one or more peak interval metrics including any of the examples described herein. When the mean peak amplitude of all signal pulse peaks 368 is less than an asystole amplitude threshold, control circuit 80 may perform a first analysis of the cardiac signal segment 352 for detecting asystole. When the mean peak amplitude of all signal pulse peaks 368 is greater than or equal to the asystole amplitude threshold, control circuit 80 may perform a second analysis of the cardiac signal segment 352 for detecting VT/VF. The asystole amplitude threshold may be 0.1 mV in an example and may correspond to a minimum R-wave or fibrillation wave amplitude expected in the cardiac signal segment 352.

The second analysis performed by control circuit 80 for detecting VT/VF when the peak amplitude metric is greater than or equal to the asystole amplitude threshold may include comparing the mean of the peak intervals 380 to a VT/VF interval threshold (and/or a count of the identified signal pulses to a threshold value). In the example shown, the mean peak interval is approximately 210 ms which is less than a VT/VF interval threshold of 260 ms, as an example. In this case, control circuit 80 may continue the second analysis for detecting VT/VF in response to the peak interval metric being less than the VT/VF interval threshold by determining VT/VF morphology features from the cardiac signal segment 352, e.g., as described below in conjunction with FIGS. 12-15. As shown in FIG. 6, control circuit 80 may optionally advance from block 220 to block 222 to determine noise metrics from the cardiac signal segment for determining if the cardiac signal segment is a noisy segment or a non-noisy segment (block 224 of FIG. 6). When the cardiac signal segment is determined to be a non-noisy segment, further analysis of the potential VT/VF rhythm segment may be performed for detecting VT/VF.

Figure 9:
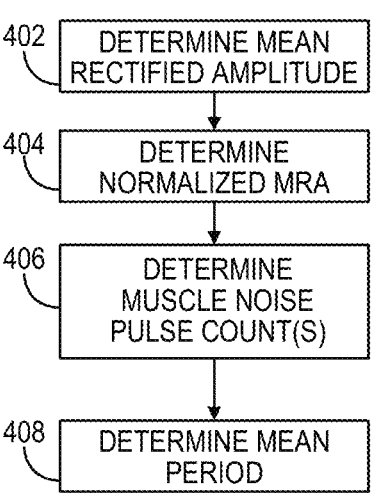
FIG. 9 is a flow chart of a method for determining noise metrics according to some examples.

FIG. 9 is a flow chart 400 of a method for determining noise metrics according to some examples for use in detecting a noisy signal segment during an analysis of a cardiac signal segment for detecting VT/VF. The method of flow chart 400 may optionally be performed by control circuit 80 at block 118 of FIG. 5 or block 222 of FIG. 6. In some examples, the metrics determined at blocks 402, 404, 406 and 408 are determined by first dividing the cardiac signal segment into multiple subsegments. For example, a 3-second cardiac signal segment of 768 samples (256 Hz sampling rate) may be divided into four subsegments of 192 samples. Each noise metric may be determined for each subsegment so that each noise metric for the overall cardiac signal segment may be determined by averaging the respective noise metrics determined for each subsegment. In other examples, the noise metrics may be determined for the entire cardiac signal segment without first dividing the segment into subsegments. Arrhythmia detection circuit 92 may determine the noise metrics from a rectified difference signal determined from the cardiac electrical signal received from morphology signal channel 87 after bandpass filtering the cardiac signal segment, e.g., using a passband of 3 to 32 Hz.

At block 402, control circuit 80 determines a mean rectified amplitude (MRA) of the cardiac signal segment. The MRA may be determined by summing all sample points in the rectified cardiac signal segment (or subsegment) and dividing by the total number of sample points. The MRA may be used at block 404 for determining the normalized MRA (NMRA). The NMRA may be determined by control circuit 80 by determining the absolute maximum peak amplitude during the cardiac signal segment (or subsegment) and dividing the MRA by the absolute maximum peak amplitude.

At block 406, control circuit 80 may determine a muscle noise pulse count (MNPC). Control circuit 80 may determine the MNPC by determining a bandpass filtered, first order difference signal from the notch-filtered cardiac electrical signal segment received from morphology signal channel 87. Zero crossings of the difference signal may be set using the techniques described above in conjunction with FIG. 7A. To further facilitate counting signal pulses, which may be noise pulses, the difference signal with zero crossings set may be rectified. Control circuit 80 may determine a noise pulse amplitude threshold by determining the maximum amplitude of the rectified difference signal over the entire cardiac signal segment (or a subsegment if determining MNPCs for multiple subsegments first) and setting the noise pulse amplitude threshold to a portion or percentage of the maximum amplitude. For instance, the noise pulse amplitude threshold may be set to be one-eighth of the maximum amplitude of the rectified difference signal. In other examples, the noise pulse amplitude threshold may be established by control circuit 80 using the techniques generally described above in conjunction with FIGS. 7B and 8B for setting a signal pulse amplitude threshold, e.g., by determining local maximums and setting a noise pulse amplitude threshold based on local maximums. In some examples, the noise pulse amplitude threshold is equal to or less than the signal pulse amplitude threshold and can be determined to be one-fourth to one-sixth (or other fraction) of the average of the local maximum amplitudes of multiple subsegments of the rectified, difference signal. The noise pulse amplitude threshold and the signal pulse amplitude threshold can be determined separately to separately identify signal pulses that are likely ventricular event signals and signal pulses that are likely noise signals. The noise signal pulses may be identified from a rectified, first order difference signal segment after different bandpass filtering of the cardiac signal segment than the bandpass filtering applied to the cardiac signal segment for identifying signal pulses that are likely ventricular event signals.

Each signal pulse having an amplitude equal to or greater than the noise pulse amplitude threshold and having a pulse width (the time interval or number of sample points between zero-crossings) that is less than or equal to a pulse width threshold (e.g., 6 sample points between zero-crossings) may be counted as a muscle noise pulse at block 406. Other example techniques for determining a muscle noise pulse count are generally disclosed in U.S. Pat. No. 10,561,331 (Zhang, et al.), incorporated herein by reference in its entirety. As indicated above, control circuit 80 may determine the MNPC for the entire cardiac signal segment or determine the MNPC for multiple subsegments and then determine the MNPC for the entire segment as the average of the subsegment MNPCs.

In some examples, the MNPC is determined for each one of multiple cardiac signal subsegments, and a maximum MNPC of the subsegment MNPCs may be determined as a noise metric. Additionally or alternatively, control circuit 80 may identify subsegments having a subsegment MNPC that is at least a threshold value, e.g., at least 6 to 8. Control circuit 80 may determine a noise metric at block 406 as a count of the subsegments having a subsegment MNPC that is at least the threshold value. Example techniques for determining noise metrics that include determining MNPCs are described below in conjunction with FIG. 10.

At block 408, control circuit 80 may determine the mean period of the cardiac signal segment. The mean period may be calculated as the inverse of the mean frequency of the cardiac signal segment, which is an estimate of the center frequency of the cardiac signal segment. The mean frequency may be determined by control circuit 80 as the ratio of the average absolute amplitude of the rectified first order difference signal (sum of all sample point amplitudes of the rectified difference signal divided by the total number of sample points) to the average absolute amplitude of the rectified cardiac signal segment (sum of all sample point amplitudes of the rectified cardiac signal segment divided by total number of sample points). As such, the mean period may be estimated as the ratio of the sum of all sample point amplitudes of the rectified cardiac signal segment to the sum of all sample point amplitudes of the rectified first order difference signal. The mean period may optionally be converted to a radian measure by multiplying this ratio by the factor $2\Pi$/(sampling frequency). The noise metrics determined according to flow chart 400 may be determined in a different order than the order shown or determined during parallel processing. In some examples, a different combination of noise metrics may be determined than the MRA, NMRA, MNPCs and mean period described here.

Figure 10:
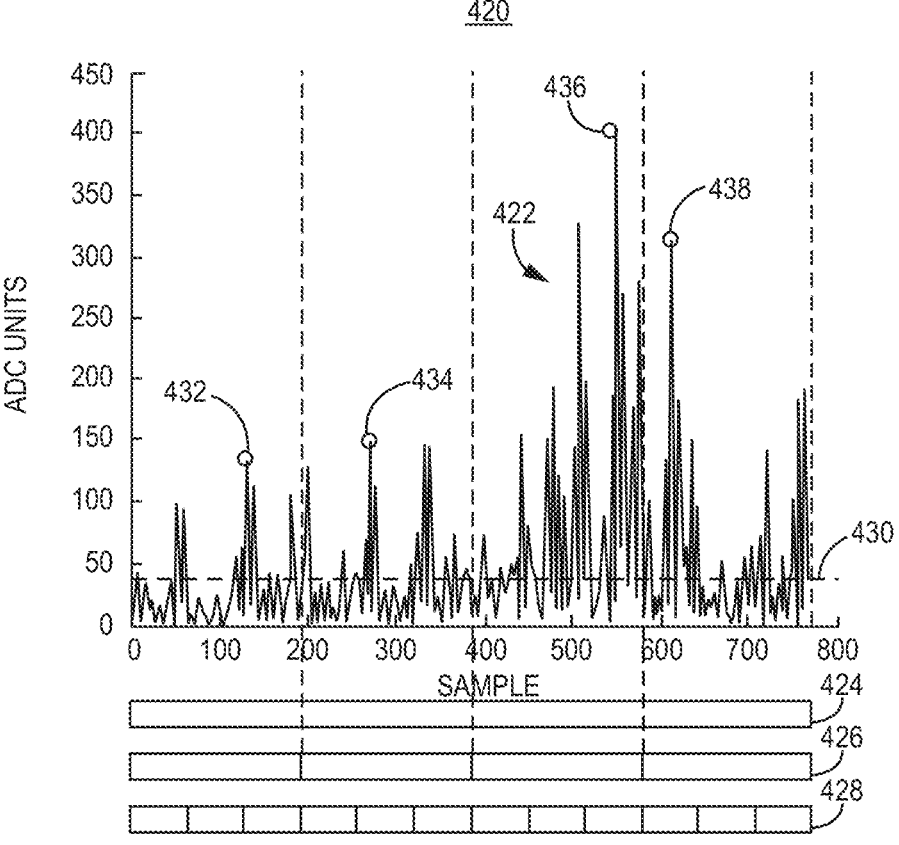
FIG. 10 is a diagram illustrating a method for determining noise metrics according to some examples.

FIG. 10 is a diagram 420 illustrating a method for determining MNPCs according to some examples. A rectified difference signal 422 is shown that is determined from a cardiac signal segment acquired over a time segment 424 that is three seconds long in this example (768 sample points when the sampling rate is 256 Hz). Control circuit 80 may receive the cardiac signal segment from morphology signal channel 87. The rectified difference signal 422 may be determined from a bandpass filtered signal, e.g., 0.5 Hz to 32 Hz bandpass filtered signal in an example, though other lower and upper cutoff frequencies may be used. The cardiac signal segment may be notch filtered by sensing circuit 86 to remove 50 Hz and 60 Hz noise and subsequently processed by a bandpass filter, difference filter and rectifier, for determining noise metrics. Control circuit 80 may set zero crossing points of the difference signal determined from the cardiac signal segment as generally described above and rectify the signal to obtain the filtered, rectified difference signal 422 shown in FIG. 10. In this example, the cardiac signal segment is noise contaminated.

Control circuit 80 may establish noise pulse amplitude threshold 430 used for identifying noise signal pulses. For example, control circuit 80 may divide the time segment 424 into first subsegments 426, which may be four equal subsegments as shown in FIG. 10. Control circuit 80 determines the local maximum 432, 434, 436 and 438 of each first subsegment 426. If the local maximum of a given subsegment is less than 20% (or other selected percentage) of the overall maximum peak amplitude 436 of the rectified difference signal 422 over the entire time segment 424, control circuit 80 may set the local maximum to be equal to the overall maximum amplitude. The noise pulse amplitude threshold 430 may be set to a percentage of the average of the local maximums 432, 434, 436 and 438. In some examples the noise pulse amplitude threshold 430 is set to one-eighth to one-fourth of the average of four local maximum amplitudes 432, 434, 436 and 438 determined from four subsegments 426 of the rectified, difference signal 422. In an example, the pulse amplitude threshold 430 is set to one-sixth of the average of the four local maximum amplitudes 432, 434, 436 and 438 determined from the four subsegments 426.

It is to be understood that the noise pulse amplitude threshold 430 for identifying signal pulses for determining MNPCs may be determined the same or differently than the signal pulse amplitude threshold used for identifying signal pulses for determining a peak amplitude metric and a peak interval metric as described in conjunction with FIGS. 7B and 8B. For instance, the noise pulse amplitude threshold 430 used for identifying and counting noise pulses may be set relatively lower, e.g., to one sixth of the mean of the local maximum amplitudes of the subsegments 426. The signal pulse amplitude threshold determined for identifying signal peaks for determining a peak amplitude metric and a peak interval metric as described in conjunction with FIGS. 7A and 7B may be relatively higher, e.g., one-third of the mean of the local maximum amplitudes of the subsegments of the rectified difference signal. Furthermore, the rectified difference signals may be filtered according to different passbands prior to identifying signal pulses (e.g., 3 to 23 Hz passband) and prior to identifying noise pulses (e.g., 3 to 32 Hz). In still other examples, the noise pulse amplitude threshold 430 used for identifying and counting noise pulses and the signal pulse amplitude threshold used for identifying signal pulses for determining a peak amplitude metric and a peak interval metric may be established by control circuit 80 using different methods, which may or may not require determining local maximum peaks of multiple subsegments of the rectified, difference signal.

In some examples, when the noise pulse amplitude threshold 430 is less than a minimum amplitude threshold, e.g., less than 3 ADC units, control circuit 80 may determine that the cardiac signal segment is not a noisy segment. The cardiac signal segment may be determined to be too low amplitude for detecting noise. When the noise pulse amplitude threshold 430 is at least the minimum amplitude threshold, control circuit 80 may proceed with determining noise metrics of the cardiac signal segment.

In some examples, control circuit 80 may further divide the time segment 424 into second subsegments 428 that are shorter than the first subsegments 426 in a process for determining noise metrics. In the example shown, control circuit 80 divides the overall time segment 424 into twelve equal subsegments 428 for determining noise pulse counts during each of the second subsegments 428, which may be referred to as subsegment MNPCs. Control circuit 80 counts the number of signal pulses having an amplitude greater than the noise pulse amplitude threshold 430 for each of the second subsegments 428. Signal pulses may additionally be required to have a signal width that is less than or equal to a pulse width threshold. A skeletal muscle myopotential pulse is a relatively narrow pulse. Signal pulses having at least a minimum amplitude and no more than a maximum pulse width may be counted by control circuit 80 for determining a MNPC. The subsegment MNPC may be determined by counting all signal pulses meeting the amplitude and pulse width requirements, without ignoring signal pulses that are less than a threshold time interval from another signal pulse as described above in conjunction with FIGS. 7B and 8B for determining a peak amplitude metric and a peak interval metric.

It is to be understood that the signal pulses counted as likely noise pulses for determining noise metrics, such as the MNPCs, are identified by control circuit 80 according to different criteria than the signal pulses identified as likely ventricular event signals for determining the peak amplitude metric and peak interval metric as described above in conjunction with FIGS. 7B and 8B. The peak amplitude and peak interval metrics are determined to estimate a ventricular rate and are therefore based on criteria for identifying signal pulses that are most likely to be true R-waves or fibrillation waves, not noise pulses. In FIG. 10, all signal pulse peaks that have an amplitude greater than noise pulse amplitude threshold 430 and have a signal width less than or equal to a pulse width threshold may be counted as a muscle noise signal pulse in each of the subsegments 428 to determine the subsegment MNPC for each of the subsegments 428.

Control circuit 80 may compare each subsegment MNPC to a threshold value to identify the number of subsegments 428 that are noisy subsegments. When the subsegment MNPC is at least 7, the subsegment can be identified as a noisy subsegment, in an example. Control circuit 80 may count the number of noisy subsegments out of all subsegments 428 as a noisy subsegment count to be used as a noise metric for identifying the cardiac signal segment received over time segment 424 as either a noisy segment or a non-noisy segment.

Additionally or alternatively, control circuit 80 may determine the subsegment having the highest subsegment MNPC out of all of the second subsegments 428. The highest subsegment MNPC may be determined as a noise metric for identifying the cardiac signal segment received over time segment 424 as either a noisy segment or a non-noisy segment. A noisy cardiac signal segment may include a high number of subsegments 428 having a moderately high MNPC and/or at least one subsegment out of second subsegments 428 having a very high MNPC. Either of these conditions may result in control circuit 80 identifying the associated cardiac signal segment as a noisy segment.

Figure 11:
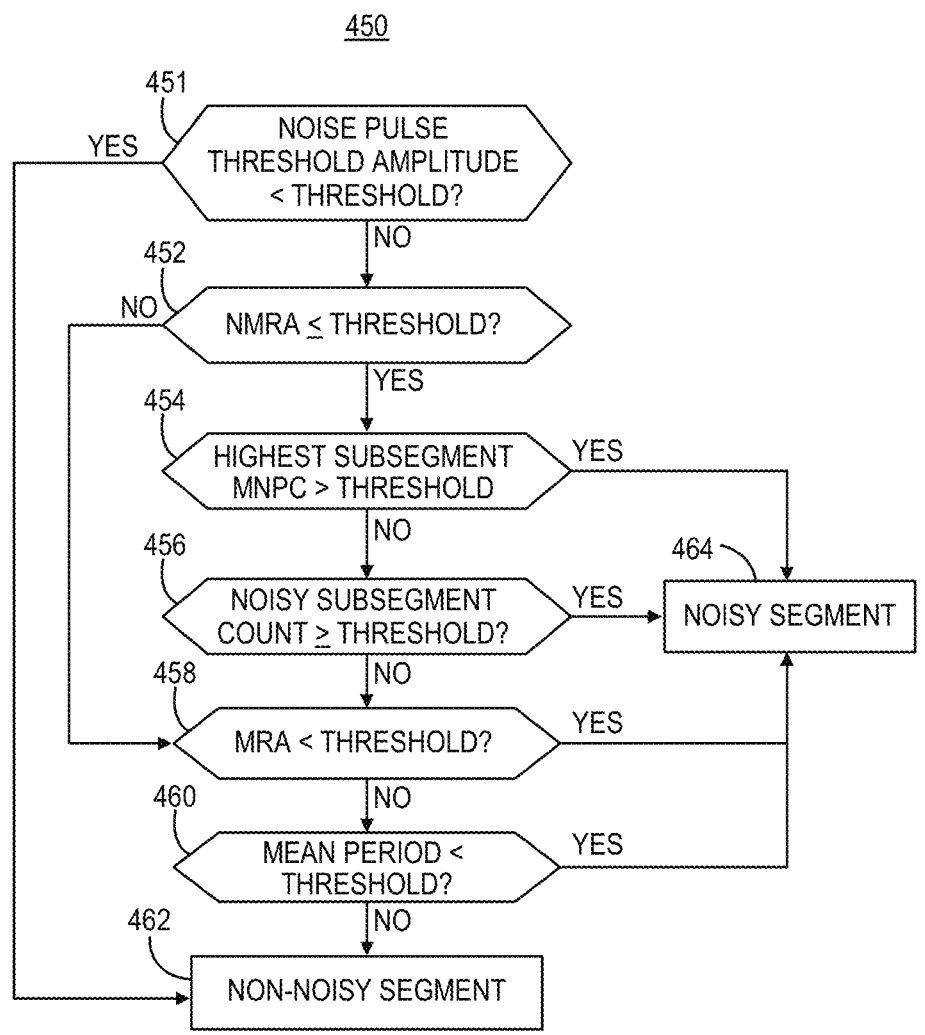
FIG. 11 is a flow chart of a method for determining when a cardiac signal meets noisy segment criteria according to some examples.

FIG. 11 is a flow chart 450 of a method for determining when a cardiac signal segment meets noisy segment criteria. The method of flow chart 450 may optionally be performed at block 124 of FIG. 5 or block 224 of FIG. 6, for example, using the noise metrics described in conjunction with FIG. 9. At block 451, control circuit 80 may compare the noise pulse threshold amplitude to a minimum threshold. As described above in conjunction with FIG. 10, the noise pulse threshold amplitude may be determined by control circuit 80 based on local maximum amplitudes. When the noise pulse threshold amplitude is less than a minimum threshold, the cardiac signal segment may be determined to be a non-noisy segment at block 462. When the noise pulse threshold amplitude is at least the minimum threshold, control circuit 80 may compare the noise metrics to various criteria for identifying the cardiac signal segment as a noisy segment or a non-noisy segment.

At blocks 452, 454 and 456, a first set of criteria are applied to the NMRA and the subsegment MNPCs to determine if the cardiac signal segment is a noisy segment. As described below, when these first criteria are unmet, alternative criteria may be applied to other noise metrics by control circuit 80 for determining if the signal segment is a noisy segment. The first set of criteria requires that the NMRA is less than or equal to a threshold (block 452) and either the highest subsegment MNPC is greater than a threshold (block 454) or the noisy subsegment count is greater than or equal to a threshold (block 456). At block 452, control circuit 80 may compare the NMRA to a corresponding threshold. When the NMRA is less than or equal to the threshold, the deviation of the cardiac signal from baseline is relatively low, which may indicate a noisy segment because the cardiac signal is frequently near or crossing the baseline. A relatively high degree of deviation from the baseline, as indicated by a relatively high NMRA, may be evidence of true VT/VF because fewer, relatively larger signals may be present in the cardiac signal segment. As such, if the NMRA is not less than or equal to the corresponding threshold at block 452, control circuit 80 may determine the cardiac signal segment to be a non-noisy segment at block 462. However, in the example of FIG. 11, control circuit 80 advances to block 458 to evaluate alternative criteria for detecting a noisy signal segment when the NMRA does not meet noisy segment criteria at block 452.

Referring again to block 452, when the NMRA is less than or equal to the corresponding threshold, control circuit 80 may determine that the cardiac signal segment is a noisy segment at block 464. In the example of FIG. 11, however, control circuit 80 applies additional noisy segment criteria at block 454 and/or block 456 for detecting the cardiac signal segment as a noisy segment based on both the NMRA and the subsegment MNPCs. In the example shown, if the highest subsegment MNPC determined from the second subsegments 428 (see FIG. 10) of the rectified difference signal is greater than a threshold value at block 454, control circuit 80 may determine that the cardiac signal segment is a noisy segment at block 464. As described above in conjunction with FIG. 10, a subsegment having a relatively high MNPC is indicative of a noisy cardiac signal segment. Control circuit 80 may detect a noisy segment at block 464 in response to the NMRA being less than or equal to a corresponding threshold and the maximum subsegment MNPC determined from all cardiac signal subsegments being greater than a threshold value ("yes" branch of block 454). The NMRA threshold may be between 40 and 50 in some examples. The threshold value compared to the highest subsegment MNPC may be between 8 and 12 in some examples. In an illustrative example, when the NMRA is less than or equal to 47 and the highest subsegment MNPC is greater than 10, control circuit 80 may determine that the cardiac signal segment is a noisy segment at block 464.

When the highest subsegment MNPC is not greater than a threshold value ("no" branch of block 454), control circuit 80 may compare the count of noisy subsegments (e.g., subsegments having a subsegment MNPC that is greater than seven or other selected threshold number) to a threshold number at block 456. Either a single subsegment having a high MNPC (as determined at block 454) or a threshold number of subsegments having a moderately high MNPC (as determined at block 456) can be an indication of a noisy segment. For example, when at least 2, 3, 4 or other selected number of subsegments are determined to be noisy subsegments (e.g., having a subsegment MNPC of at least 7), control circuit 80 may determine that the threshold number of noisy subsegments is met at block 456. When the count of noisy subsegments is greater than a threshold number, and the NMRA is less than or equal to a corresponding threshold, control circuit 80 may detect a noisy cardiac signal segment at block 464. In an example, when the NMRA is less than or equal to 47 and the count of noisy subsegments is greater than three, control circuit 80 may detect a noisy segment at block 464.

In other examples, a MNPC for the entire cardiac signal segment may be determined, which may be determined by counting all signal pulses greater than the noise pulse amplitude threshold and having a pulse width less than the width threshold across the entire cardiac signal segment. In still other examples, a MNPC for the entire cardiac signal segment may be determined by averaging the subsegment MNPCs, with each subsegment MNPC determined by counting all signal pulses greater than the noise pulse amplitude threshold and narrower than the width threshold within each subsegment (e.g., four to twelve subsegments). The MNPC for the entire cardiac signal segment may be compared to a threshold value for detecting the cardiac signal segment as a noisy segment, alone or in combination with the NMRA being less than or equal to a corresponding threshold and/or in combination with other noise metric criteria disclosed herein.

Control circuit 80 may additionally or alternatively detect a noisy segment when the MRA is determined to be less than a threshold at block 458. When the first criteria applied at blocks 452, 454, and 456 relating to NMRA and subsegment MNPCs are not met, control circuit 80 may apply criteria to the MRA. When the MRA is low, the relatively low amplitude cardiac signal segment is unlikely to include true R-waves or fibrillation waves and may be determined to be a noisy segment at block 464. The MRA threshold may be between 30 and 40, as examples, and can be 33 in an example.

Control circuit 80 may additionally or alternatively detect a noisy segment in response to the mean period being less than a respective threshold at block 460. When the mean period is less than 80, 85, 90 or other selected threshold, control circuit 80 may detect a noisy segment at block 464. A relatively high mean period may indicate relatively low frequency R-waves or fibrillation waves are present in the cardiac signal segment as opposed to relatively higher frequency noise pulses. When the noise metrics determined for the cardiac signal segment do not meet the noisy segment criteria applied at blocks 452 through 456, or the alternative criteria applied at block 458 or at block 460, control circuit 80 can determine that the cardiac signal segment is a non-noisy segment at block 462.

Figure 12:
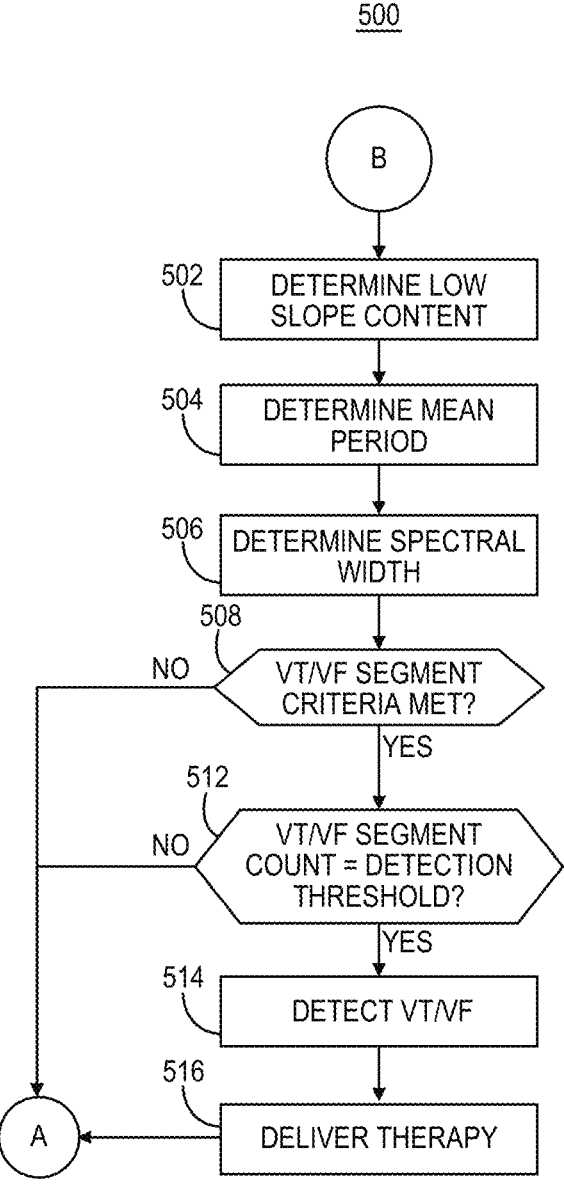
FIG. 12 is a flow chart of a method that may be performed during an analysis for detecting VT/VF when a peak amplitude metric of the cardiac signal segment is greater than an amplitude threshold.

FIG. 12 is a flow chart 500 of a method that control circuit 80 may perform during the second analysis for detecting VT/VF when the peak amplitude metric is greater than an asystole amplitude threshold as generally described above in conjunction with FIGS. 5 and 6. Referring to FIG. 6, when control circuit 80 determines that the cardiac signal segment is a potential VT/VF rhythm segment at block 226, control circuit 80 may advance to the process of flow chart 500 as indicated by connector "B."

Control circuit 80 may determine one or more morphology metrics from the cardiac signal segment that discriminate between true VT/VF rhythms and other conditions, such as a supraventricular tachycardia, rapidly conducted atrial fibrillation, or oversensing of P-waves, T-waves, and/or non-cardiac noise. The morphology metrics can be determined from sample points spanning the entire cardiac signal segment and are not dependent on identifying cardiac signal segments that include the time of a ventricular sensed event signal received from sensing channel 83 or 85. In some instances, no ventricular sensed event signals may be received from sensing circuit 86 during the cardiac signal segment being analyzed for VT/VF detection. As described above, the cardiac signal segment may be received from the morphology signal channel 87 and may be a bandpass and notch filtered signal. In some examples, the cardiac electrical signal is filtered using a 2 Hz to 40 Hz bandpass filter, a 3 Hz to 32 Hz bandpass filter, or a 4 Hz to 30 Hz bandpass filter in various examples. Control circuit 80 may determine a gradient signal and/or bandpass filtered signal from the signal received from morphology signal channel 87 followed by determining a first order difference signal that is rectified for determining the VT/VF morphology metric(s) from the cardiac signal segment.

In the example shown in FIG. 12, control circuit 80 determines the low slope content (LSC) of the n-second cardiac signal segment at block 502. The LSC may be determined as the total number of sample points of the rectified, first order difference signal that have an amplitude less than a low slope amplitude threshold. Control circuit 80 may establish the low slope amplitude threshold based on the local maximum peak amplitudes of multiple subsegments for the rectified difference signal. As described above, e.g., in conjunction with FIGS. 7B and 8B, control circuit 80 may divide the rectified difference signal into four subsegments and determine the local maximum amplitude of each subsegment. When a local maximum amplitude is less than a percentage, e.g., 20%, of the overall maximum peak amplitude of the rectified difference signal, the overall maximum peak amplitude may be substituted for the local maximum amplitude. The low slope amplitude threshold may be set to a percentage or fraction of the mean of the local maximum amplitudes. In one example, the low slope amplitude threshold is set to between 5% and 10% or about one-sixteenth of the mean of the local maximum amplitudes.

Once the low slope amplitude threshold is established, control circuit 80 may sum all of the sample points of the rectified difference signal that have an amplitude that is less than or equal to the low slope amplitude threshold. Control circuit 80 may determine the LSC by dividing the sum by the total number of sample points in the cardiac signal segment. In other examples, a LSC may be determined for each one of multiple subsegments of the cardiac signal segment, e.g., by summing all sample points of the rectified difference signal having an amplitude less than or equal to the low slope amplitude threshold and dividing by the total number of sample points in the subsegment. The LSC of the overall cardiac signal segment may be determined as the average of the subsegment LSCs.

Additionally or alternatively, control circuit 80 may determine the mean period from the cardiac signal segment at block 504. A method for determining the mean period is described above in conjunction with FIG. 9. In some examples, the mean period may be determined by control circuit 80 for determining noise metrics. In this case, when the cardiac signal segment is determined to be a non-noisy segment, the mean period may be already known for the cardiac signal segment for use in detecting VT/VF. In other examples, the noise metrics may not be determined for detecting a noisy segment. Instead, the mean period may be determined by control circuit 80 at block 504 as a morphology metric used to discriminate between VT/VF and non-VT/VF segments.

Control circuit 80 may use the mean period for determining the spectral width (SW) at block 506. Control circuit 80 may determine the SW as the fundamental period of the cardiac signal segment less the mean period. In some examples, control circuit 80 may determine the fundamental period as the mean of the peak intervals that are determined between identified signal peaks, e.g., as described above in conjunction with FIGS. 7B and 8B. In some examples, the fundamental frequency may be determined as a trimmed mean, e.g., by removing one or more longest and/or one or more of the shortest peak intervals between the signal peaks identified from the rectified difference signal determined from the cardiac signal segment. To illustrate, with reference to FIG. 8B, the peak intervals 380 may be buffered in memory 82. The mean of the peak intervals in the buffer may be determined as the fundamental period of the cardiac signal segment. In some examples, the shortest and the longest peak intervals may be ignored and the mean of all remaining peak intervals may be determined. The SW may then be determined by control circuit 80 by subtracting the mean period from the fundamental period.

At block 508, control circuit 80 may determine if the morphology metrics of the cardiac signal segment meet VT/VF segment criteria. In some examples, the LSC, mean period, and/or SW may each be compared to respective thresholds for identifying the cardiac signal segment as a VT/VF segment. As described below in conjunction with FIGS. 13-15, each of the LSC, SW and mean period may be useful discriminators for identifying VT/VF rhythms and non-VT/VF rhythms. In an illustrative example, when the mean period is at least 60 ms, the SW is less than or equal to 10 ms and the LSC is less than or equal to 0.7 (70%), control circuit 80 may determine that the cardiac signal segment is a VT/VF segment at block 508. When the mean period is less than 60 ms or the SW is greater than 10 ms or the LSC is greater than 0.7, control circuit 80 may determine that the cardiac signal segment is a non-VT/VF segment. In another example, when the mean period is at least 60 ms and the SW normalized by mean period (SW/mean period) is less than or equal to 0.1, the cardiac signal segment is a VT/VF segment at block 508.

In some examples, control circuit 80 determines that the cardiac signal segment is a VT/VF segment when the LSC is less than a threshold set as a linear function of the SW. Accordingly, in some examples the VT/VF segment criteria requires that the LSC be less than a factor of the SW plus an offset. When LSC is plotted as a function of SW, a linear relationship between LSC and SW may discriminate VT/VF rhythm segments from non-VT/VF rhythm segments. In one example, control circuit 80 determines that the cardiac signal segment is a VT/VF rhythm when the LSC falls below the line defined by m*SW+b where m is −0.05 and b is 1.16 in an example. The slope m and the y-intercept b of the linear function of SW may be selected based on patient data to yield a high sensitivity and specificity for VT/VF detection.

When the VT/VF segment criteria are not met at block 508, control circuit 80 may return to block 202 of FIG. 6 (as indicated by connector "A") to obtain the next n-second cardiac signal segment for processing and analysis. VT/VF is not detected. When control circuit 80 determines that the VT/VF segment criteria are met at block 508, control circuit 80 may determine if a threshold number of cardiac signal segments have been detected as VT/VF segments at block 512. In some examples, control circuit 80 may detect VT/VF at block 514 in response to a single cardiac signal segment being detected as a VT/VF segment. In other examples, control circuit 80 may count consecutive or non-consecutive cardiac signal segments that are determined to be VT/VF segments. When a threshold number of consecutive or non-consecutive cardiac signal segments, e.g., at least 2 out of 3 signal segments, are detected as VT/VF segments, control circuit 80 may detect VT/VF at block 514. When the threshold number of consecutive VT/VF segments is not reached, control circuit 80 may return to block 202 of FIG. 6 as indicated by connector "A" to analyze the next cardiac signal segment.

When VT/VF is detected by control circuit 80 at block 514, therapy delivery circuit 84 may deliver tachyarrhythmia therapy at block 516 in response to the VT/VF detection. The therapy may include one or more ATP sequences and/or one or more CV/DF shock pulses. After the delivered therapy has successfully terminated the detected VT/VF, control circuit 80 may return to block 202 of FIG. 6. As described above in conjunction with FIG. 5, after detecting VT/VF, control circuit 80 may continue to analyze cardiac signal segments, e.g., according to the method of FIG. 12, for detecting VT/VF signal segments during high voltage capacitor charging and/or after delivering ATP therapy. In some instances, after a VT/VF detection, control circuit 80 may detect termination of the VT/VF rhythm when less than a threshold number of the most recent cardiac signal segments are VT/VF signal segments. Control circuit 80 may cancel a CV/DF shock before it is delivered if termination is detected first.

Figure 13:
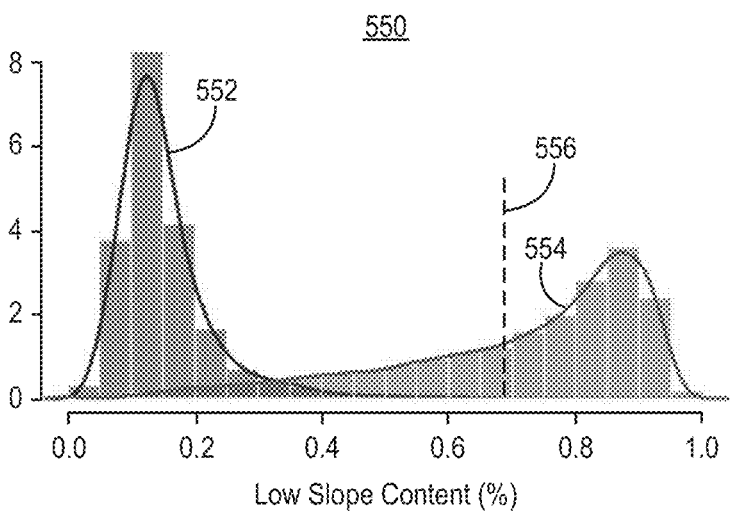
FIG. 13 is a plot of the frequency distribution of values of low slope content that occur during VT/VF signal segments and during non-VT/VF signal segments.

FIG. 13 is a plot 550 of the frequency distribution of values of the LSC determined from cardiac signal segments that are received during VT/VF and from cardiac signal segments that are received during non-VT/VF rhythms. The LSCs of signal segments received during VT/VF are shown by the frequency distribution curve 552. The LSCs of signal segments received during non-VT/VF are shown by frequency distribution curve 554. As observed in FIG. 13, the LSC is a sensitive discriminator between VT/VF and non-VT/VF cardiac signal segments. A hypothetical LSC threshold 556 that detects VT/VF segments with a high sensitivity and discriminates between VT/VF signal segments and non-VT/VF signal segments with a relatively high degree of specificity is shown. The LSC threshold 556 may be between 0.4 and 0.8 in various examples and may be 0.7 in some examples.

Figure 14:
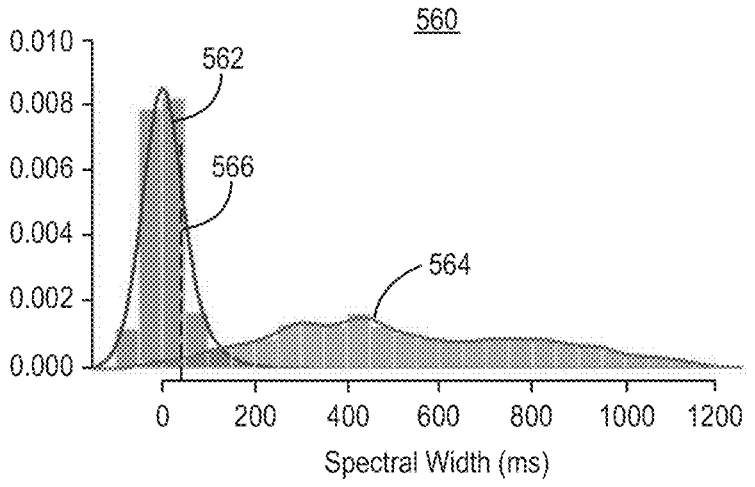
FIG. 14 is a plot of the frequency distribution of values of spectral width that occur during VT/VF signal segments and during non-VT/VF signal segments.

FIG. 14 is a plot 560 of the frequency distribution of values of SW that occur during VT/VF signal segments as shown by frequency distribution curve 562 and during non-VT/VF signal segments as shown by frequency distribution curve 564. As observed in FIG. 14, SW is a relatively sensitive discriminator between VT/VF and non-VT/VF cardiac signal segments. A hypothetical SW threshold 566 that discriminates between VT/VF signal segments and non-VT/VF signal segments with a relatively high degree of specificity is shown. The SW threshold 566 may be between 5 and 200 ms or between 10 and 150 ms and can be 10 ms in an example.

Figure 15:
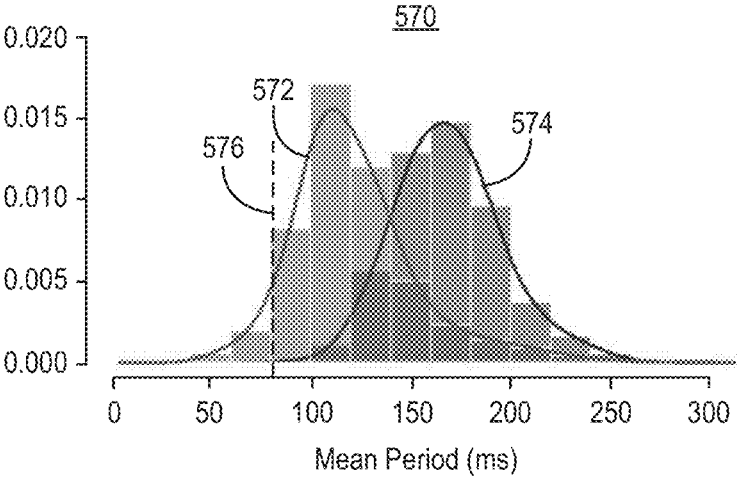
FIG. 15 is a plot of the frequency distribution of values of mean period that occur during VT/VF signal segments and during non-VT/VF signal segments.

FIG. 15 is a plot 570 of the frequency distribution of values of mean period that are determined from non-VT/VF signal segments as shown by frequency distribution curve 572 and determined from VT/VF signal segments as shown by frequency distribution curve 574. As observed in FIG. 15, the mean period can be used as one morphology metric determined from cardiac signal segments for discriminating between VT/VF and non-VT/VF cardiac signal segments but taken alone may be less specific than LSC or SW. A hypothetical mean period threshold 576 that discriminates between VT/VF signal segments and non-VT/VF signal segments with a high sensitivity for detecting VT/VF is shown. The mean period threshold may be between 60 and 170 ms and is 60 ms in an example.

The cardiac signal segment metrics of LSC, SW and/or mean period may be used alone or in combination for detecting VT/VF signal segments based on comparisons to respective individual thresholds 556, 566 and 576 as shown in FIGS. 13, 14 and 15 in some examples. For example, when at least two or when all three metrics meet a VT/VF threshold requirement, the cardiac signal segment may be determined to be a VT/VF segment. When any one of the LSC, SW or mean period does not meet a VT/VF threshold requirement, the cardiac signal segment may be determined to be a non-VT/VF segment. The LSC threshold 556 (FIG. 13), SW threshold 566 (FIG. 14) and mean period threshold 576 (FIG. 15) may each be selected to provide an overall high sensitivity and specificity for detecting VT/VF when used in combination. As such, at least one threshold may be selected to provide high sensitivity while another threshold may be selected to provide high specificity to detecting VT/VF. In other examples, a linear function between two of the metrics, such as between LSC and SW, may be defined for determining a signal segment as a VT/VF segment. In still other examples, a three-dimensional relationship between LSC, SW and mean period may be determined for defining VT/VF segment detection criteria.

Other combinations of morphology metrics may include determining ratios, differences, or other relationships of the morphology metrics. For example, the ratio of SW to mean period may be compared to a respective threshold for detecting a VT/VF segment in some examples. When the mean period is at least 60 ms and the SW/mean period ratio is less than or equal to 0.1, for example, the 3-second cardiac signal segment may be identified as a VT/VF segment in some examples. In another example, when the mean period is at least 65 and the SW/mean period ratio is less than or equal to a variable threshold that may be defined as a function of the mean period, the 3-second cardiac signal segment may be identified as a VT/VF segment. In an illustrative example, the SW/mean period ratio may be compared to a linear function of the mean period given by −0.0035*(mean period)+0.145. When the SW/mean period ratio is less than or equal to this variable threshold, the 3-second cardiac signal segment may be identified as a VT/VF segment. Other coefficients and constants may be used to define a variable threshold as a function of a morphology metric that is applied to another morphology metric or mathematical relationship of two or more morphology metrics. A variable threshold defined as a function of a morphology metric may be tailored to an individual patient or optimized based on data from a population of patients for identifying VT/VF segments with high sensitivity and/or specificity. Other thresholds may be defined depending on the time length of the cardiac signal segment for reliably discriminating between the morphology metrics of a VT/VF segment and a non-VT/VF segment based on mean period and the SW normalized by mean period. The combination of mean period and SW normalized by mean period as morphology metrics used for discriminating between VT/VF segments and non-VT/VF segments can reliably detect VF segments more than 99% of the time, without requiring determining LSC, rate metrics or noise metrics from the cardiac signal segment. It is recognized, however, that numerous criteria may be conceived for discriminating between VT/VF segments and non-VT/VF segments using a variety of combinations of LSC, mean period and/or SW, one or more rate metrics, and/or one or more noise metrics. Such combinations may include mathematical combinations of two or more metrics (e.g., SW normalized by mean period). VT/VF segment criteria may include one or more thresholds applied to a respective metric or mathematical combination of metrics where each threshold can be defined as a constant or as a function, e.g., a linear function, of a metric determined from the cardiac signal segment.

Figure 16:
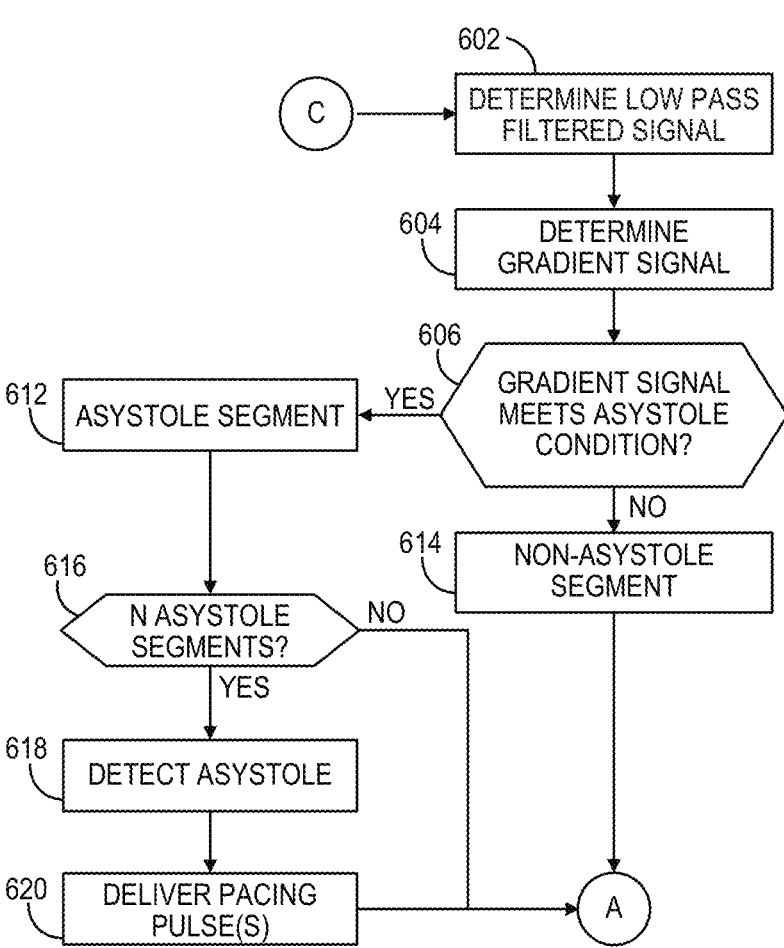
FIG. 16 is a flow chart of a method for detecting asystole based on cardiac signal segment analysis according to some examples.

FIG. 16 is a flow chart 600 of a method for detecting asystole based on cardiac signal segment analysis according to one example. The process of flow chart 600 may begin at block 602 each time an n-second cardiac signal segment is acquired. In some examples, the process of flow chart 600 may be performed when control circuit 80 determines that low amplitude criteria are met as described above in conjunction with FIG. 5. For instance, as described in conjunction with FIG. 6, if the peak amplitude metric determined from identified signal pulses is less than an asystole amplitude threshold, control circuit 80 may identify potential asystole and advance to flow chart 600 as indicated by connector "C" for performing a first analysis of the cardiac signal segment for detecting asystole. When the first analysis for performing asystole is performed, the second analysis for detecting VT/VF as described above may be skipped for the current cardiac signal segment in some examples.

The first analysis of the cardiac signal segment for detecting asystole is performed to determine a signal stability metric that is representative of the degree of signal fluctuations present in the cardiac signal segment. During asystole, the cardiac signal segment is expected to be relatively flat with a low degree of signal fluctuations. At block 602, control circuit 80 may determine a low pass filtered signal to smooth the cardiac signal segment. Signal smoothing by averaging or filtering may result in a relatively flat signal when no ventricular activity is present and enhance any ventricular activity signals relative to attenuated noise signals that may be present in the cardiac signal segment. Control circuit 80 may be configured to determine a low pass filtered signal at block 602 from the wideband and notch filtered cardiac signal received from morphology signal channel 87 by determining a running average of a predetermined number of sample points of the cardiac signal segment. In one example, the low pass filtered signal is determined by summing the most recent 10 to 40 sample points in a moving average window. In one example, each sample of the low pass filtered signal is determined by determining a moving window sum of the most recent 21 sample points of the cardiac signal segment, which may be scaled by dividing by ten or another scaling factor. Other low pass filtering or signal averaging methods may be used.

At block 604, control circuit 80 determines a gradient signal from the low pass filtered signal. The gradient signal may be generated by a central difference method in some examples, e.g., by determining the difference between the i+1 and i−1 sample points and dividing by 2. In this way, a signal representing the gradient or rate of change of the low pass filtered cardiac signal segment is determined. In other examples, a forward difference or backward difference method could be used. Generally the low pass filter applied at block 602 may be followed by a high pass filtering method. In some examples, a bandpass filter may be applied to the wideband and notch filtered cardiac signal received from morphology signal channel 87 and used for determining when an asystole condition is met.

At block 606, control circuit 80 determines if the gradient signal meets an asystole condition for at least a predetermined time interval, which may be all or a portion of the cardiac signal segment and/or include all or a portion of multiple cardiac signal segments. The asystole condition may be met when the gradient signal remains substantially within an asystole detection range for at least a predetermined time interval. When asystole is present, the gradient signal is expected to be a substantially flat signal with small fluctuations. If asystole is not present, ventricular activity will cause fluctuations in the gradient signal that exceed the asystole range. When the gradient signal exceeds the asystole range for a threshold number of sample points of the gradient signal, control circuit 80 may determine that the cardiac signal segment is a non-asystole segment. When the gradient signal is within the asystole range for at least a threshold number of sample points out a predetermined number of consecutive or non-consecutive sample points (or predetermined time interval), control circuit 80 may determine that a persistent asystole condition exists and detect asystole. In some examples, control circuit 80 may apply asystole condition criteria to the gradient signal at block 606 for determining when a predetermined percentage or portion of the gradient signal sample points are within the asystole range and detect the associated cardiac signal segment as an asystole segment at block 612.

In some examples, control circuit 80 may determine that asystole condition criteria are met at block 606 when at least Y consecutive running windows of Z sample points include at least X sample points of the gradient signal that fall within the asystole range. In an illustrative example, when at least 5 sample points out of a running window of 21 sample points are within the asystole range for 100 to 700 consecutive running windows, or other portion of the cardiac signal segment or number of sample points, the asystole condition criteria are met at block 606. The cardiac signal segment can be determined to be an asystole segment by control circuit 80 at block 612 when the asystole condition criteria are met at block 606.

At block 616 control circuit 80 may determine if a threshold number of asystole segments have been detected. Control circuit 80 may detect asystole at block 618 when the asystole condition is met during at least 1, at least 2 or at least 3 consecutive cardiac signal segments, for example. In various examples, when the asystole condition criteria are met for a first cardiac signal segment, which may be a 3-second segment, control circuit 80 may determine if asystole condition criteria are met for at least one additional cardiac signal segment which may have the same or a different duration than the first asystole signal segment. For example, one or more additional cardiac signal segments that may be 0.5, 1, 1.5, 2, 3, 4, or 5 seconds in duration may be analyzed for determining if the asystole condition criteria are met for multiple time segments having a total cumulative time duration of 4 to 8 seconds, for example. For instance, when one 3-second segment and a programmable number of one to ten additional 0.5 second segments meet asystole condition criteria, control circuit 80 may detect asystole at block 618. The asystole condition criteria may be required to be met continuously for a predetermined number of running windows of Z sample points spanning one or more cardiac signal segments at block 616 in order for asystole to be detected at block 618.

Therapy delivery circuit 84 may be configured to deliver one or more pacing pulses at block 620 in response to control circuit 80 detecting asystole. Therapy delivery circuit 84 may deliver a pacing pulse upon detection of asystole, or control circuit 80 may schedule a pacing pulse by starting a pacing escape interval, which may be set to a hysteresis interval or a lower rate pacing interval. The hysteresis interval may be set to 2 to 4 seconds, as examples. The lower rate pacing interval may be set to 1 to 1.5 seconds as examples. In some examples, when asystole is detected based on a relatively longer total cumulative time duration of cardiac signal segment(s) meeting the asystole condition criteria, e.g., a total of five to eight seconds, therapy delivery circuit 84 may deliver an asystole pacing pulse immediately at block 620 in response to the detection of asystole.

In other examples, when asystole can be detected based on one or more cardiac signal segments having a relatively shorter total cumulative time duration, e.g., 3 to 4 seconds total, control circuit 80 may start a pacing escape interval to schedule an asystole pacing pulse. The pacing escape interval may be 2 to 4 seconds long such that, if an intrinsic ventricular event is sensed during the pacing escape interval by sensing circuit 86 and/or the asystole condition is no longer met due to the gradient signal exceeding the asystole range, the scheduled asystole pacing pulse may be withheld (e.g., cancelled or re-scheduled by resetting a pacing escape interval). When control circuit 80 does not receive a ventricular sensed event signal from one of sensing channels 83 or 85 before the pacing escape interval expires and/or the gradient signal continues to meet the asystole condition during the pacing escape interval, the scheduled pacing pulse may be delivered by therapy delivery circuit 84 upon expiration of the pacing escape interval.

In an illustrative example of 3 to 4 seconds of total cumulative time duration of the cardiac signal segment(s) meeting asystole condition criteria at block 616 and a pacing escape interval set to 3 to 4 seconds, a pacing pulse may be delivered after 5 to 8 seconds of asystole. In some examples, control circuit 80 may continue to analyze the amplitude of the gradient signal during the pacing escape interval. If asystole detection criteria become unmet during a pacing escape interval, e.g., the asystole condition criteria are not met during one or more cardiac signal segments, control circuit 80 may cancel the scheduled pacing pulse.

Referring again to block 606, in some examples when the asystole condition criteria are not met for at least a threshold time interval during a cardiac signal segment at block 606, the cardiac signal segment may be determined to be a non-asystole segment at block 614. Control circuit 80 may obtain the next cardiac signal segment to analyze the next segment for asystole. As shown in FIG. 16, control circuit 80 may return to the flow chart of FIG. 6 as indicated by connector "A." It is to be understood however, that the process of FIG. 16 may operate independently of, and in some examples in parallel to, other sensing and detection algorithms such as the VT/VF detection analysis described above and/or sensing ventricular event signals by sensing circuit 86 for controlling bradycardia pacing and/or detecting and counting VT/VF intervals.

For example, control circuit 80 may obtain the next n-second cardiac signal segment and return to block 602 for determining the low pass filtered signal and the gradient signal over running windows of Z sample points for classifying the cardiac signal segment as either an asystole segment or a non-asystole segment and continue to operate in parallel to cardiac signal segment processing and analysis performed for VT/VF detection. In still other examples, the process of FIG. 16 may be performed on an ongoing basis without waiting for an n-second cardiac signal segment to be obtained. Control circuit 80 may determine the averaged signal and the gradient signal of the averaged signal over a running window of Z sample points in a continuous manner without waiting for an n-second cardiac signal segment to be acquired. When a threshold number of Y running windows each include at least X sample points within the asystole range, the asystole condition criteria may be met at block 606. Asystole may be detected at block 618 when the asystole condition determined at block 606 persists for a threshold time interval, e.g., 4 to 6 seconds. Therapy delivery circuit 84 may deliver a pacing pulse or start a pacing interval, e.g., a hysteresis pacing interval or a lower rate pacing interval, for scheduling a pacing pulse in response to the asystole detection. When control circuit 80 does not receive a ventricular sensed event signal during the pacing escape interval and/or the asystole condition continues to be met during the pacing escape interval, therapy delivery circuit 80 may deliver the scheduled pacing pulse.

Figure 17:
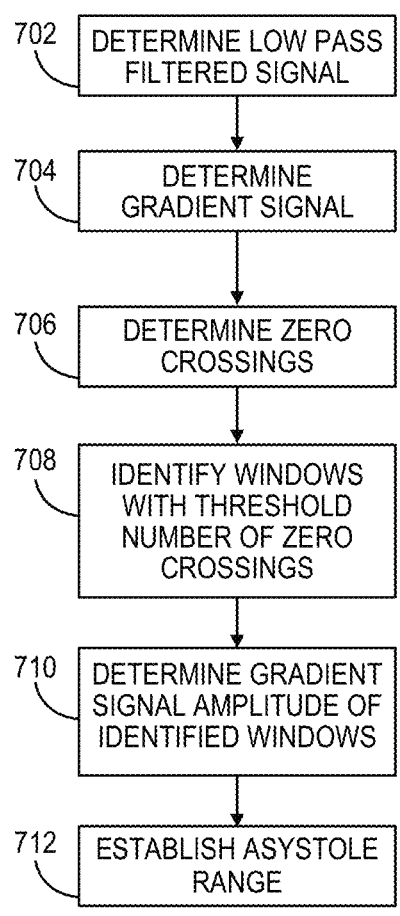
FIG. 17 is a flow chart of a method for establishing an asystole range applied to a gradient signal determined from a cardiac signal segment for determining when asystole condition criteria are met.

FIG. 17 is a flow chart 700 of a method for establishing the asystole range applied to the gradient signal for determining when asystole condition criteria are met at block 606 of FIG. 16. In some examples, the asystole range applied to the gradient signal may be predetermined or programmable by a user. In other examples, the asystole range is established by control circuit 80 based on processing and analysis of one or more cardiac signal segments received from morphology signal channel 87 for determining a patient-specific asystole range. The process of flow chart 700 may be performed upon implantation of ICD 14 and may be repeated periodically to update the asystole range, e.g., once per day, once per hour, or once per minute, as examples. The process for establishing the asystole range may be performed when control circuit 80 has confirmed a normal sinus rhythm, e.g., based on the rate of ventricular sensed event signals received from sensing circuit 86 and/or morphology matching scores between sensed signals and an R-wave template. In some examples, control circuit 80 may perform the process of flow chart 700 on a triggered basis. For example, when a patient physical activity signal, e.g., an activity count determined from an accelerometer signal or other patient physical activity signal, indicates an increased level of activity that may be indicative of increased skeletal muscle myopotential signals contaminating the cardiac electrical signal.

At block 702, control circuit 80 determines the low pass filtered signal as described above in conjunction with FIG. 16. The gradient signal is determined from the low pass filtered signal by control circuit 80 at block 704, using the techniques described above. In other examples, other methods of low pass and high pass or bandpass filtering of the cardiac signal may be performed. At block 706, control circuit 80 identifies zero crossings of the gradient signal. Control circuit 80 may count the number of zero crossings of the gradient signal in each running (e.g., moving) window of Z sample points, e.g., 10 to 40 sample points or 21 sample points as in the example given above. Windows of Z sample points may be running or moving windows of Z sample points that include overlapping sample points between consecutive windows. In other examples, the windows of Z sample points may be non-overlapping windows. For the sake of illustration, zero crossings are counted in each of multiple running windows of Z sample points. At block 708, control circuit 80 identifies each running window of Z sample points that includes a threshold number of zero crossings, e.g., at least five to twelve zero crossings or eight zero crossings as an example when the running window includes 21 sample points. It is to be understood that the running windows may include more or fewer than 21 sample points and the threshold number of zero crossings may be adjusted accordingly.

At block 710, control circuit 80 may determine a representative amplitude of the gradient signal during all running windows identified at block 708 as including at least the threshold number of zero crossings. For example, a maximum, median or mean amplitude of the gradient signal sample points in the running windows identified at block 708 may be determined as a representative amplitude at block 710. When at least the threshold number of zero crossings occurs within a running window, the sample points within the running window may represent a near baseline signal that could be an indication of absent ventricular activity. Few or no zero crossings may indicate that the signal is away from the baseline, which may be indicative of a possible ventricular event signal. Accordingly an asystole range of the gradient signal amplitude may be established at block 712 based on the amplitude of the gradient signal during running (or non-overlapping) windows having at least a threshold number of zero crossings.

In one example, control circuit 80 determines the absolute maximum of the gradient signal during all of the running windows identified at block 708. The asystole range may be set equal to +/− the absolute maximum amplitude of the gradient signal determined from the running windows identified at block 708. In other examples, the asystole range may be determined as the absolute maximum of the gradient signal plus (or minus) a predetermined offset. Additionally or alternatively, the asystole range may be based on a percentage of the absolute maximum of the gradient signal. In still other examples, the asystole range may be set based on the absolute value of another representative value of the gradient signal amplitude, such as a mean or median, determined from the running windows identified at block 708. For instance, a mean amplitude of the absolute amplitude of all non-zero points of the gradient signal during each running window identified at block 708 may be determined. The asystole range may be determined based on the absolute maximum of the mean amplitudes, e.g., by identifying the maximum and setting the asystole range to +/− the maximum of the mean amplitudes plus a predetermined percentage or offset (which could be zero).

Figure 18:
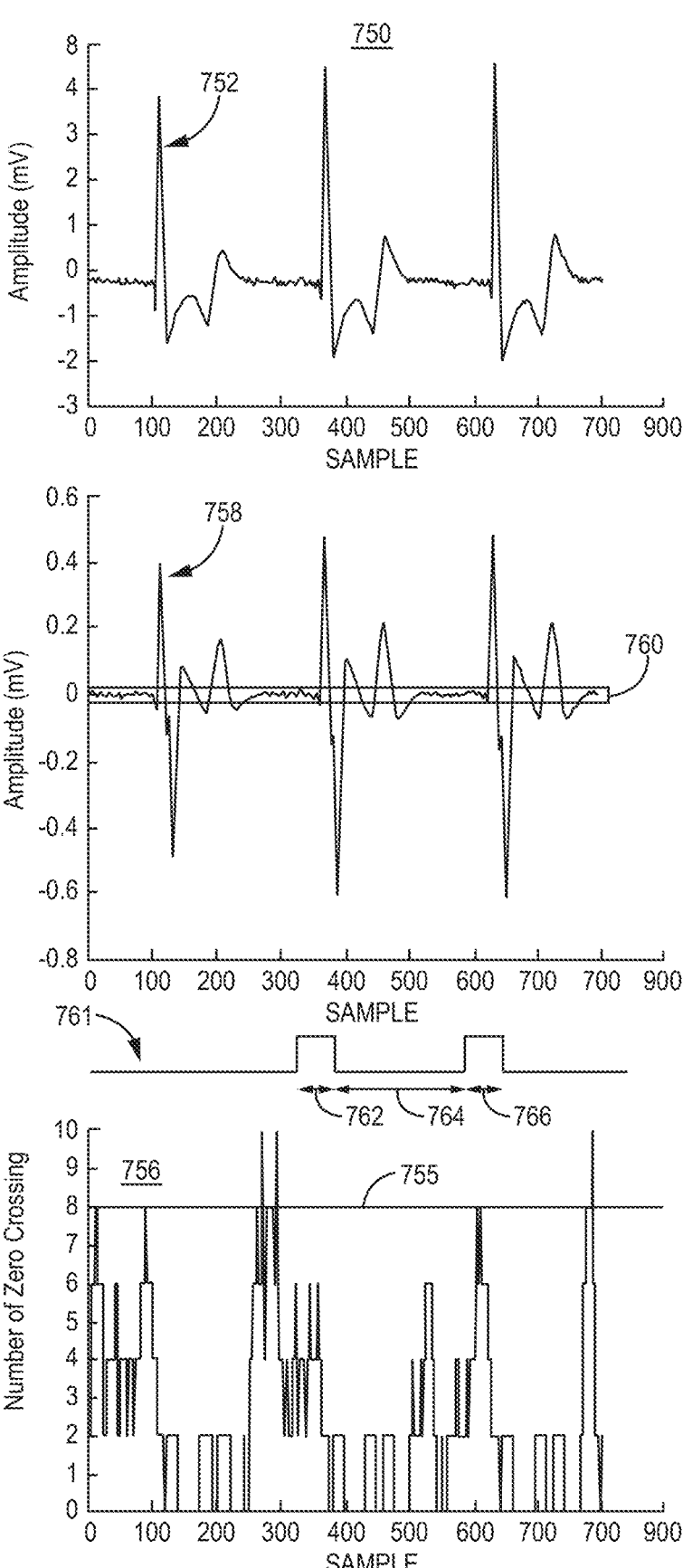
FIG. 18 is a graph of a bandpass and notch filtered cardiac signal segment and the gradient signal determined from the cardiac signal segment.

FIG. 18 is a diagram 750 of a cardiac signal segment 752 and a gradient signal 758 determined from the cardiac signal segment 752 and used by control circuit 80 for detecting asystole. The cardiac signal segment 752 is received over a 3-second time segment in this example and may be the bandpass and notch filtered cardiac signal received from morphology signal channel 87. The gradient signal 758 may be determined from the cardiac signal segment 752, e.g., after low pass filtering cardiac signal segment 752. As described above, each sample point of a low pass filtered signal may be determined by summing 21 consecutive sample point amplitudes and dividing by 10. The gradient signal 758 may be determined from the low pass filtered signal by determining each sample point of the gradient signal by determining the central difference, e.g., as the average of the i+1 and the i−1 sample points.

Control circuit 80 may compare the gradient signal 758 to an asystole range 760 for determining when the asystole condition is met by each window of Z sample points. The windows of Z sample points may be moving windows that are advanced one or more sample points at a time or may be consecutive non-overlapping windows of Z sample points in various examples. The asystole range 760 may be established by control circuit 80 using the techniques described in conjunction with FIG. 17.

For example, control circuit 80 may determine the number of zero crossings in each window of Z sample points. The plot 756 of the number of zero crossings in each moving window of sample points is shown in the bottom graph of FIG. 18. Control circuit 80 identifies the sample points of the gradient signal 758 in each moving window having at least a threshold number of zero crossings (755). The threshold number is 8 zero crossings in the example shown. From the sample points of the identified moving windows, control circuit 80 may determine a representative value of the amplitude of the gradient signal 758 during the identified moving windows, e.g., a maximum or average of the absolute amplitudes of the gradient signal 758 during the identified moving windows. Control circuit 80 may set the asystole range 760 based on the representative value of the amplitude of the gradient signal 758 during the windows of Z sample points identified to have at least the threshold number of zero crossings 755.

Control circuit 80 may determine that asystole condition criteria are met when at least X sample points out of Z consecutive sample points of a sample window are within the asystole range 760 for at least Y consecutive moving windows of Z sample points. In one example, X is 5, Z is 12, and Y is 100. Control circuit 80 may generate a signal 761 that indicates when the asystole condition criteria are met for the required number of consecutive running windows. The asystole condition criteria are determined to be met over time interval 762 and time interval 766. The asystole condition criteria are not met over time interval 764. Control circuit 80 may require that the asystole condition criteria (as indicated by signal 761) be met continuously for an asystole detection threshold time interval, e.g., for at least 4 seconds, at least 5 seconds, 6 seconds, 7 seconds, or 8 seconds as examples, in order to detect asystole. The asystole detection threshold time interval may extend over all or a portion of one or more consecutive cardiac signal segments, which may be equal or unequal in duration.

As such, when the asystole condition signal 761 is high at the end of one cardiac signal segment, it may remain high at the start of the next cardiac signal segment until the asystole condition criteria are no longer met. A count of the number of most recent consecutive moving windows that meet the X of Z sample points within the asystole range 760 at the expiration of the preceding n-second cardiac signal segment may be retained at the start of the next n-second cardiac signal segment. The threshold number of Y consecutive moving windows meeting the asystole condition may span a portion of more than one cardiac signal segment. The asystole condition signal 761 may be set high during an n-second cardiac signal segment before Y moving windows have occurred during the n-second cardiac signal segment when a first portion of the most recent Y consecutive moving windows meet the asystole condition during the preceding n-second cardiac signal segment and a second portion of the most recent Y consecutive windows occur in the current n-second cardiac signal segment.

When the asystole condition criteria are met persistently for at least the asystole detection time interval, e.g., when the asystole condition signal 761 remains high for a predetermined time interval, control circuit 80 may detect asystole. Therapy delivery circuit 84 may immediately deliver a pacing pulse in response to the asystole detection. In other examples, control circuit 80 may schedule a pacing pulse by starting a pacing escape interval. Control circuit 80 may detect expiration of the pacing escape interval without receiving a sensed event signal from sensing channels 83 or 85. Therapy delivery circuit 84 may deliver the scheduled pacing pulse in response to the expiration of the pacing escape interval. If control circuit 80 receives a ventricular sensed event signal during the pacing escape interval, or the asystole condition becomes unmet during the pacing escape interval, control circuit 80 may cancel the pending, scheduled pacing pulse.

Figure 19:
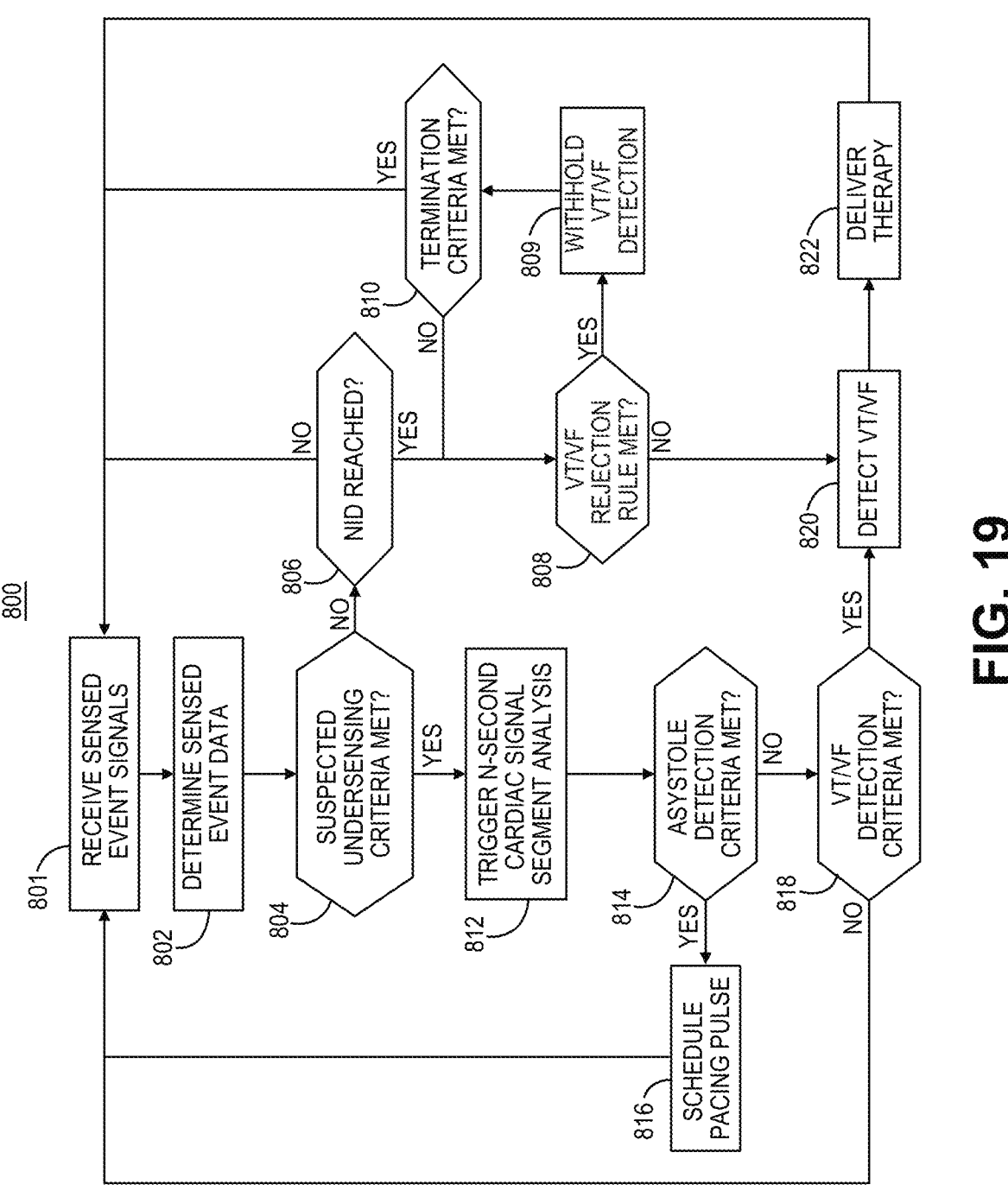
FIG. 19 is a flow chart of a method for detecting asystole and delivering therapy as needed according to one example.

FIG. 19 is a flow chart 800 of a method for detecting arrhythmia and delivering therapy as needed according to one example. Control circuit 80 may receive ventricular sensed event signals from both sensing channels 83 and 85 at block 801. Control circuit 80 may determine sensed event data at block 802 for storing in memory 82 for each respective sensing channel 83 and 85. The sensed event data may include the in-channel RRI determined between the currently received ventricular sensed event signal and the most recent preceding ventricular sensed event signal received from the same sensing channel (or in some cases a preceding pacing pulse). Control circuit 80 may additionally determine the sensed event amplitude, e.g., by determining the maximum peak amplitude of the cardiac signal sensed by the sensing channel 83 or 85 during a post-sense R-wave peak tracking period. Control circuit 80 may additionally determine a morphology matching score corresponding to each ventricular sensed event signal received from the sensing channels 83 and 85. The morphology matching score may be determined between an R-wave template stored in memory 82 and a relatively short time segment of the cardiac signal received from morphology signal channel

87 and buffered in memory 82 in response to receiving a ventricular sensed event signal. For example, a 188 ms segment of the cardiac signal received from the morphology signal channel 87 that encompasses the time of a ventricular sensed event signal received from either sensing channel 83 or 85 may be analyzed by control circuit 80 for determining a morphology matching score between the buffered cardiac signal segment and a previously determined R-wave morphology template stored in memory 82.

Control circuit 80 may store a predetermined number of RRIs, corresponding sensed event amplitudes, and morphology matching scores for each ventricular sensed event signal received from each sensing channel 83 and 85 in memory 82, e.g., in a first-in-first-out (FIFO) buffer. For example, memory 82 may be configured to store the most recent twelve in-channel RRIs for each sensing channel 83 and 85. Each RRI may be stored with an associated sensed event amplitude and morphology matching score corresponding to the ventricular sensed event signal ending the RRI in some examples.

At block 804, control circuit 80 may analyze the sensed event data for determining if suspected undersensing criteria are met. When R-waves or fibrillation waves are undersensed, RRIs determined from ventricular sensed event signals do not reflect the true ventricular rate. A ventricular tachyarrhythmia may go undetected. As such, control circuit 80 may determine when the sensed event data meets suspected undersensing criteria at block 804 for triggering processing and analysis of one or more n-second cardiac signal segments by arrhythmia detection circuit 92 at block 812 using any of the example techniques described above, e.g., as described in conjunction with any of FIGS. 5-18. Example methods for determining when suspected undersensing criteria are met at block 804 are described below in conjunction with FIG. 20. In general, one or more relatively long RRIs buffered for one or both sensing channels 83 and 85, relatively low sensed event amplitudes for both sensing channels, and/or a threshold number of low morphology matching scores may all be indications of possible undersensing of ventricular event signals by sensing channels 83 and 85.

When the suspected undersensing criteria are not met at block 804, control circuit 80 may determine if an NID is reached by the RRIs determined for at least one sensing channel 83 or 85 at block 806. When the RRIs determined for at least one sensing channel has reached an NID for detecting VT or VF, control circuit 80 may advance to block 808 for determining if a VT/VF rejection rule is met for withholding a VT/VF detection when the NID is reached. VT/VF rejection rules may be met based on morphology analysis performed by control circuit 80 on time segments of the cardiac signal received from the morphology signal channel 87 in some examples.

For instance, morphology analysis of relatively short cardiac signal time segments, e.g., 150 to 400 ms segments or 180 to 350 ms segments as examples with no limitation intended, which may include the time of a single ventricular sensed event signal received from sensing channel 83 or 85, may be performed at block 808. For example, morphology analysis of cardiac signal segments buffered in memory 82 in response to receiving a single ventricular sensed event signal from either sensing channel 83 or 85 may be performed for determining if a supraventricular tachyarrhythmia (SVT) rejection rule is met for withholding a VT/VF detection at block 809. Morphology analysis of cardiac signal segments may be performed at block 808 to determine if a cardiac oversensing rejection rule is met, e.g., a T-wave oversensing (TWOS) rejection rule or a P-wave oversensing (PWOS) rejection rule. When a cardiac oversensing rejection rule is met, a VT/VF detection based on the NID being met at block 806 may be withheld at block 809.

Morphology analysis of cardiac signal segments may additionally or alternatively be performed at block 808 to determine if a noise rejection rule is met due to the presence of skeletal muscle myopotentials, EMI or other non-cardiac noise being present in the cardiac electrical signal. When a noise rejection rule is met, control circuit 80 may withhold a VT/VF detection based on the NID being met at block 809. Various morphology analysis and criteria applied at block 808 may include determining whether a VT/VF rejection rule is met due to detecting noise, oversensing of cardiac events such as P-wave or T-waves, and/or evidence of SVT based on the morphology of the cardiac signal segments buffered in response to ventricular sensed event signals. In each of these situations addressed by the VT/VF rejection rules, the NID may be reached at block 806 when a true VT/VF rhythm that is treatable by ATP therapy or a CV/DF shock is not actually present.

The morphology analysis performed at block 808 can be different than the morphology analysis performed on n-second segments as described above in conjunction with FIGS. 5-18 for detecting asystole or VT/VF without relying on ventricular sensed event signals or determination of RRIs from ventricular sensed event signals from sensing channels 83 and 85. Examples of morphology analysis that may be performed for rejecting or withholding a VT/VF detection based on a rejection rule being met when an NID is reached are generally disclosed in U.S. Pat. No. 9,956,423 (Zhang, et al.), U.S. Pat. No. 10,470,681 (Greenhut, et al.), U.S. Pat. No. 10,507,332 (Zhang, et al.), U.S. Pat. No. 10,555,684 (Zhang et al.), U.S. Pat. No. 10,561,332 (Zhang, et al.), and U.S. Pat. No. 10,850,113 (Cao, et al.), all of which are incorporated herein by reference in their entirety.

If a VT/VF rejection rule is met at block 808, control circuit 80 withholds the VT/VF detection at block 809. Control circuit 80 may verify that termination criteria are not met at block 810. If termination criteria are not met, control circuit 80 may detect VT/VF at block 820 after the NID has been reached at block 806 and no VT/VF rejection rules are met at block 808. Control circuit 80 may determine that termination criteria are met when a threshold number of RRIs, sensed or paced, are greater than or equal to the VT detection interval (when VT detection is enabled) and/or the VF detection interval. In another example, if a mean, median or other representative metric of the most recently buffered RRIs remains longer than the VT detection interval and/or VF detection interval for a predetermined termination time interval, control circuit 80 may determine termination of the fast ventricular rhythm at block 810.

In still other examples, control circuit 80 may determine that termination criteria are met at block 810 when a VT or VF interval counter reset condition is met. Control circuit 80 may be configured to identify normal sinus rhythm (NSR) events while processing the morphology signal from the morphology signal channel 87 for determining if the VT/VF morphology criteria become satisfied. NSR events may be identified based on detecting an RRI as an NSR interval and/or determining that the sensed event signal morphology matches an NSR morphology. The reset condition may require that at least X of Y ventricular events sensed by the sensing channel 83 or 85 that produced ventricular sensed event signals that caused the NID to be reached are NSR events. In some examples the reset condition may additionally require that at least one (or other threshold number of)

the detected NSR events occurs within the most recent two (or other predetermined number of) sensed event signals. Examples of VT/VF interval counter reset conditions that may be applied at block 810 are generally disclosed in U.S. Publication No. 2021/0138243 (Zhang, et al.), incorporated herein by reference in its entirety.

When the morphology criteria do become met at block 808 (no rejection rules met) after the NID is reached and before termination criteria are met, control circuit 80 may detect VT/VF at block 820. In some examples, if a VT/VF detection has been withheld for a maximum high rate time out interval and the NID is still met, VT/VF may be detected at block 820. In response to the VT/VF detection, therapy delivery circuit 84 may deliver tachyarrhythmia therapy at block 822 to terminate the VT/VF rhythm. Therapy delivered at block 822 may include one or more sequences of ATP and/or one or more CV/DF shocks.

Returning to block 804, when control circuit 80 determines that suspected undersensing criteria are met, control circuit 80 may perform alternative or parallel processing and analysis of n-second cardiac signal segments received from morphology signal channel 87 to enable detection of VT/VF when ventricular sensed event signals received from sensing channels 83 and 85 may be unreliable due to undersensing. Processing and analysis of one or more n-second cardiac signal segments by control circuit 80 for arrhythmia detection according to the techniques disclosed herein is triggered at block 812 in response to the suspected undersensing criteria being met at block 804. As described above, e.g., in conjunction with FIGS. 5 and 6 and other related flow charts and diagrams presented herein, control circuit 80 may perform a first analysis of a cardiac signal segment for determining if asystole detection criteria are met at block 814. The first analysis may be performed when the cardiac signal segment meets low amplitude criteria, e.g., when a peak amplitude metric of identified signal pulses in the cardiac signal segment is less than an asystole amplitude threshold. Example methods for determining that asystole detection criteria are met at block 814 are described above in conjunction with FIGS. 16-18.

When asystole detection criteria are met, control circuit 80 may schedule a pacing pulse at block 816. The scheduled pacing pulse may be delivered immediately by therapy delivery circuit 84 upon detection of the asystole or upon expiration of a pacing escape interval set by control circuit 80 for scheduling the pacing pulse. When a ventricular sensed event signal is not received from sensing channel 83 or 85 by control circuit 80 during the pacing escape interval, therapy delivery circuit 84 may deliver the scheduled pacing pulse. After delivering the pacing pulse, control circuit 80 may return to block 801 to continue the process of receiving ventricular sensed event signals and determining sensed event data for determining when an NID is reached or when suspected undersensing criteria are met again.

If the low amplitude criteria are not met or the asystole detection criteria are not met based on a first analysis of the cardiac signal segment, control circuit 80 may perform a second analysis of the cardiac signal segment at block 818 for detecting VT/VF. In some examples, when suspected undersensing criteria are met at block 804 control circuit 80 may advance directly to block 818 to determine if VT/VF detection criteria are met, without performing the first analysis for detecting asystole, or the first analysis for detecting asystole and the second analysis for detecting VT/VF may be performed in parallel.

Control circuit 80 may perform the processing and analysis of the n-second cardiac signal segment(s) at block 818 for detecting VT/VF according to any of the example techniques described above in conjunction with FIGS. 5 through 15. When VT/VF detection criteria are not met based on the processing and analysis of one or more n-second cardiac signal segments, control circuit 80 may return to block 801 to continue receiving ventricular sensed event signals from sensing channels 83 and 85 and determining sensed event data. When VT/VF detection criteria are met at block 818, e.g., based on determining a threshold number of VT/VF segments, control circuit 80 may detect VT/VF at block 820. The VT/VF detection may be made by control circuit 80 without requiring an NID to be reached based on RRIs determined from ventricular sensed event signals received from sensing channels 83 and 85. Moreover, when a VT/VF detection is made based on the analysis of the n-second cardiac signal segment(s), control circuit 80 may not be receiving ventricular sensed event signals from sensing channels 83 and 85 due to undersensing. In response to detecting VT/VF at block 820, therapy delivery circuit 84 may deliver one or more ATP therapies and/or one or more CV/DF shocks to terminate the VT/VF rhythm at block 822.

While not illustrated in the example flow chart of FIG. 19, in other examples, when the VT/VF detection criteria are met based on the n-second cardiac signal analysis at block 818, control circuit 80 may advance to block 808 (instead of directly to block 820 as shown) to verify that VT/VF rejection rules are not met before detecting VT/VF at block 820. Some VT/VF rejection rules may be based on an analysis of cardiac signal segments that are buffered in response to ventricular sensed event signals from sensing channels 83 and 85. Those VT/VF rejection rules may be irrelevant or may not be applied when suspected undersensing criteria are met at block 804, triggering the n-second cardiac signal segment analysis for VT/VF detection. Other VT/VF rejection rules, such as a noise rejection rule, may be based on analysis of a cardiac signal segment that is buffered independently of ventricular sensed event signals from sensing channels 83 and 85. When VT/VF detection criteria are met at block 818, but a VT/VF rejection rule is met at block 808, control circuit 80 may withhold the VT/VF detection at block 809.

While not shown explicitly in FIG. 19, it is to be understood that prior to delivering a shock therapy at block 822, in response to a VT/VF detection at block 820, control circuit 80 may determine the VT/VF morphology metrics from one or more cardiac signal segments, e.g., during high voltage capacitor charging, for confirming that VT/VF is still being detected prior to shock delivery. In some examples, when one or more cardiac signal segments are determined to be non-VT/VF segments during capacitor charging based on the most recently determined VT/VF morphology metrics, control circuit 80 may detect termination of the detected VT/VF rhythm and return to block 801 without delivering a shock at block 822. For instance, when less than 2 out of the most recent 3 cardiac signal segments or less than 5 out of the most recent 8 cardiac signal segments are VT/VF signal segments, control circuit 80 may determine that the detected VT/VF rhythm is terminated, e.g., either spontaneously or by ATP therapy that may be delivered during capacitor charging, prior to shock delivery Control circuit 80 may cancel the CV/DF shock and return to block 801 to continue receiving cardiac event signals. If ventricular sensed event signals are being received from sensing circuit 86 by control circuit 80 during capacitor charging, RRIs may be analyzed for use in detecting termination of the VT/VF rhythm.

Figure 20:
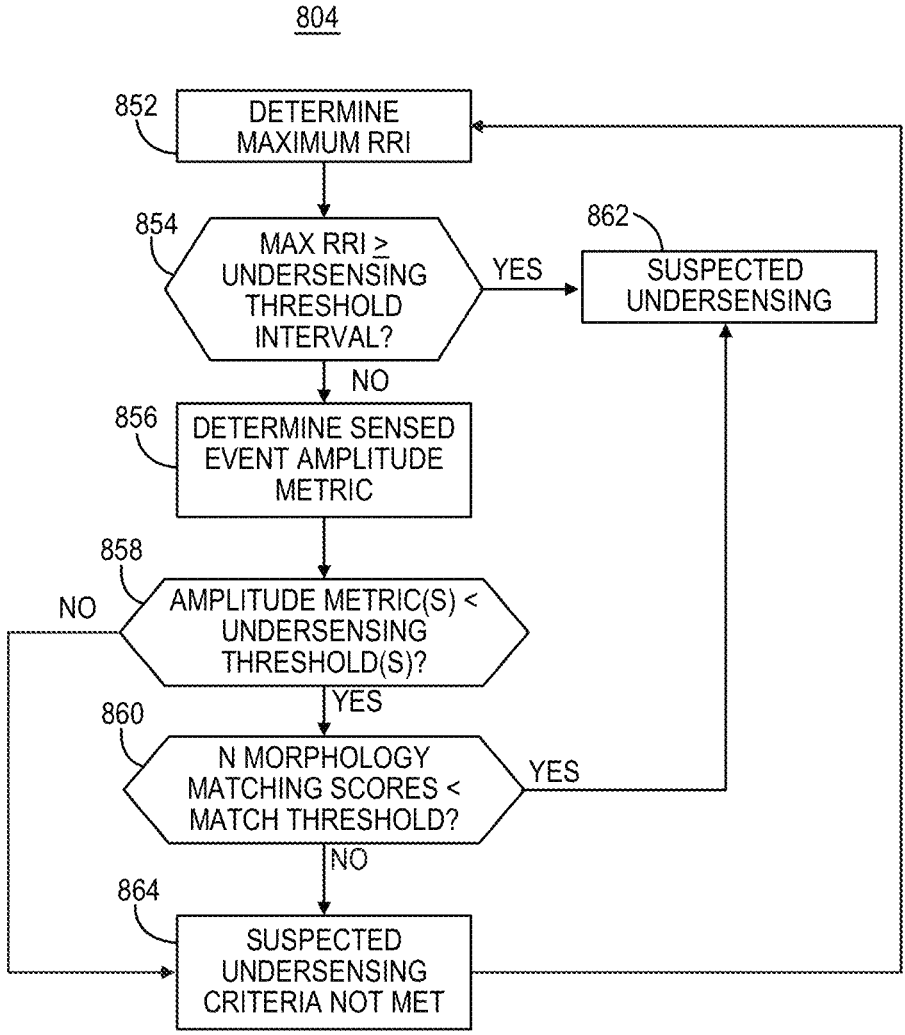
FIG. 20 is a flow chart of a method for determining when suspected undersensing criteria are met according to some examples.

FIG. 20 is a flow chart 804 of a method for determining when suspected undersensing criteria are met at the identically numbered block 804 of flow chart 800 in FIG. 19. Control circuit 80 may analyze the sensed event data buffered in memory 82 at block 802 of FIG. 19 for determining when suspected undersensing criteria are met at block 804. At block 852 of FIG. 20, control circuit 80 may determine a maximum RRI from among all of the RRIs buffered for both sensing channels 83 and 85. The most recent 8 to 20 RRIs may be buffered for each sensing channel 83 and 85, for example. When either sensing channel 83 or sensing channel 85 produces a ventricular sensed event signal at an RRI that is greater than or equal to an undersensing threshold interval as determined at block 854, control circuit 80 may determine that suspected undersensing criteria are met at block 862. The undersensing threshold interval may be, for example, between 2 seconds and 4 seconds and is 2.5 seconds in one example. Processing and analysis of the n-second cardiac signal segment(s) for arrhythmia detection is triggered at block 812 of FIG. 19 in response to an RRI determined based on ventricular sensed event signals received from either sensing channel 83 or 85 that is greater than or equal to the undersensing threshold interval.

Additionally or alternatively, control circuit 80 may determine if a sensed event amplitude metric is less than an undersensing amplitude threshold. At block 856, control circuit 80 may determine a mean, median, minimum, maximum or other representative amplitude of the sensed event amplitudes stored in memory 82 for one or each of sensing channels 83 and 85 as sensed event data. In one example, the median sensed event amplitude is determined for each sensing channel 83 and 85 from twelve (or other selected number of) buffered sensed event amplitudes stored for the respective sensing channel 83 or 85. At block 858, control circuit 80 may compare the median sensed event amplitude determined for each sensing channel 83 and 85 to an undersensing threshold amplitude.

When the median sensed event amplitudes determined from both sensing channels are each less than a respective undersensing threshold amplitude, control circuit 80 may determine that the suspected undersensing criteria are met at block 862.

Control circuit 80 may set the undersensing threshold amplitude to a multiple of the currently programmed sensitivity setting for each respective sensing channel 83 and 85. The sensitivity setting corresponds to the minimum amplitude that a sensing channel 83 or 85 will set the R-wave sensing threshold to for sensing a ventricular event signal. The programmed sensitivity may range from 0.075 mV up to 1.2 mV, as examples. The undersensing threshold amplitudes applied to the representative sensed event signal amplitudes determined from each sensing channel 83 and 85 may be different from each other. Each undersensing threshold amplitude may be set based on the respective sensitivity of the sensing channel 83 or 85 using the same multiple or a different multiple of the sensitivity. The multiple of the sensitivity used to set the undersensing threshold amplitude may range from 2 to 6 and may be between 2.5 and 5 as examples.

In an illustrative example, when the median sensed event amplitude determined from buffered sensed event peak amplitudes for a first sensing channel of sensing channels 83 and 85 is less than 2.6 times the current sensitivity of the first sensing channel and the median sensed event amplitude determined from buffered sensed event peak amplitudes for the second sensing channel of sensing channels 83 and 85 is less than 5 times the current sensitivity for the second sensing channel, control circuit 80 may determine that the amplitude metrics are less than undersensing thresholds at block 858. If the amplitude metric(s) are not less than the respective undersensing threshold(s) ("no" branch of block 858), control circuit 80 may determine that suspected under- sensing criteria are not met at block 864.

When the amplitude metric(s) are less than the respective undersensing threshold(s) at block 858, control circuit 80 may detect suspected undersensing at block 862. In the example shown, suspected undersensing is detected by control circuit 80 when the amplitude metric(s) are less than the undersensing threshold(s) (as determined at block 858) and at least N morphology matching scores buffered with the sensed event data are less than a match threshold as deter- mined by control circuit 80 at block 860.

Control circuit 80 may determine a count of morphology matching scores buffered with the sensed event data for each sensing channel 83 and 85 that are less than a match threshold at block 860. A morphology matching score greater than or equal to the match threshold is indicative of a sensed event signal that matches a normal sinus R-wave with a high degree of confidence. When at least eight (or other selected threshold number of) morphology matching scores out of the twelve buffered matching scores for a given sensing channel 83 or 85 are less than the match threshold, control circuit 80 may determine that suspected undersens- ing criteria are met at block 862. In other examples, the threshold number of morphology matching scores that are less than the match threshold may be met by a total count of morphology matching scores buffered for both sensing chan- nels 83 and 85. For example, if eight morphology matching scores are less than the match threshold out of the twenty- four most recent morphology matching scores buffered collectively for both sensing channels 83 and 85, the sus- pected undersensing criteria may be met at block 862.

In the example shown in FIG. 20, control circuit 80 determines that suspected undersensing criteria are met at block 862 when at least one RRI is greater than or equal to the undersensing threshold interval (decision block 854) or when the sensed event amplitude metrics for both sensing channels are less than respective undersensing thresholds and a threshold number of morphology matching scores determined from both sensing channels are less than the match threshold (combination of decision blocks 858 and 860). In other examples, one or more decision requirements relating to RRIs, sensed event amplitudes, and/or morphology matching scores or any combination thereof may be applied as criteria for determining when suspected undersensing criteria are met. When suspected undersensing criteria are met, control circuit 80 may trigger analysis of one or more n-second cardiac signal segments for processing and analy- sis for detecting VT/VF without requiring an NID to be reached based on ventricular sensed event signals received from sensing channels 83 and 85.

When the criteria applied at block 854 are not met ("no" branch of block 854) and the criteria applied at blocks 858 or 860 are not met ("no" branch of blocks 858 or "no" branch of block 860), control circuit 80 determines that the suspected undersensing criteria are not met at block 864. When undersensing criteria are not met, control circuit 80 may continue to rely on ventricular sensed event signals received from sensing channels 83 and 85 for detecting and counting VT/VF intervals for detecting VT/VF as described above in conjunction with FIG. 19. As shown in FIG. 19, control circuit 80 may determine when an NID is reached for detecting VT/VF when suspected undersensing criteria are not met at block 804.

In the example of FIG. 19, analysis of the n-second cardiac signal segment(s) for detecting arrhythmia without necessarily determining RRIs based on ventricular sensed event signals is performed only when triggered in response to suspected undersensing criteria being met at block 804 based on an analysis of the cardiac electrical signals sensed by sensing circuits 83 and/or 85. By triggering the process- ing and analysis of n-second cardiac signal segments for detecting arrhythmia only when suspected undersensing criteria are met, processing burden and power can be con- served. It is contemplated however that the analysis of n-second cardiac signal segments may be performed on an on-going basis in parallel to the determination of RRIs for counting VT/VF intervals for detecting VT/VF when an NID is reached (and VT/VF rejection rules are not met). In this case, VT/VF may be detected at block 820 in response to VT/VF detection criteria being met at block 818, e.g., when the LSC, SW and/or mean period determined from at least one cardiac signal segment meet respective threshold criteria for detecting a VT/VF segment as described in any of the examples given above. The NID may or may not be reached at block 806. In other instances, VT/VF may be detected at block 820 based on the NID being reached and no VT/VF rejection rules being met. The VT/VF detection criteria applied at block 818 may or may not be met in this parallel processing method for detecting VT/VF based on RRI analysis and/or based on n-second cardiac signal segment analysis.

Further disclosed are the following examples:

Example 1. A medical device including a sensing circuit configured to sense at least one cardiac electrical signal and a control circuit in communication with the sensing circuit. The control circuit can be configured to deter- mine an amplitude metric from a first cardiac signal segment of the at least one cardiac electrical signal sensed by the sensing circuit over a first time interval and determine if the amplitude metric meets an ampli- tude threshold. The medical device may perform one of: a first analysis of the first cardiac electrical signal segment for detecting a first arrhythmia in response to the amplitude metric not meeting the amplitude thresh- old; or a second analysis of the first cardiac electrical signal segment for detecting a second arrhythmia dif- ferent than the first arrhythmia in response to the amplitude metric meeting the amplitude threshold. The medical device further includes a therapy delivery circuit in communication with the control circuit, the therapy delivery circuit configured to deliver one of: a first electrical stimulation therapy in response to the control circuit detecting the first arrhythmia based on at least the first analysis; or a second electrical stimulation therapy different than the first electrical stimulation therapy in response to the control circuit detecting the second arrhythmia based on at least the second analy- sis.

Example 2. The medical device of example 1 wherein the control circuit is further configured to determine the amplitude metric by identifying signal pulses from the first cardiac signal segment, determining a peak ampli- tude of each of the identified signal pulses and deter- mining the amplitude metric based on the determined peak amplitudes.

Example 3. The medical device of example 2 wherein the control circuit is further configured to identify the signal pulses from the first cardiac signal segment by identifying a plurality of subsegments of the first car- diac signal segment, determining a local maximum from each of the plurality of subsegments, determining a signal pulse amplitude threshold based on the local maximums and identifying the signal pulses from the first cardiac signal segment by identifying pulses having an amplitude greater than the signal pulse amplitude threshold.

Example 4. The medical device of any of examples 2-3 wherein the control circuit is further configured to identify the signal pulses by identifying pulses that are at least a minimum time interval apart.

Example 5. The medical device of any of examples 1~4 wherein the control circuit is further configured to perform the second analysis of the first cardiac signal segment for detecting the second arrhythmia by identifying signal pulse peaks from the first cardiac signal segment, determining peak intervals between the identified signal pulse peak, determining a peak interval metric based on the determined peak intervals and determining if the peak interval metric meets a ventricular tachyarrhythmia threshold interval.

Example 6. The medical device of example 5 wherein the control circuit is further configured to determine that the peak interval metric does not meet the ventricular tachyarrhythmia threshold interval and terminate the second analysis of the first cardiac signal segment for detecting the ventricular tachyarrhythmia when the peak interval metric does not meet the ventricular tachyarrhythmia threshold interval.

Example 7. The medical device of any of examples 1-6 wherein the control circuit is further configured to perform the second analysis of the first cardiac signal segment for detecting the second arrhythmia by determining a noise metric from the first cardiac signal segment, determining that the noise metric does not meet noisy segment criteria; and detecting the second arrhythmia based on the second analysis of the first cardiac signal segment at least in response to the noise metric not meeting the noisy segment criteria.

Example 8. The medical device of example 7, wherein the control circuit is further configured to determine the noise metric by determining at least one of a mean rectified amplitude of the first cardiac signal segment, a normalized mean rectified amplitude of the first cardiac signal segment or a mean period of the first cardiac signal segment.

Example 9. The medical device of any of examples 7-8 wherein the control circuit is further configured to determine a subsegment count of noise pulses in each of a plurality of subsegments of the first cardiac signal segment, determine the noise metric by determining a maximum count of the subsegment counts of noise pulses and determine that the noisy segment criteria are not met when the maximum count is less than a first threshold value.

Example 10. The medical device of any of examples 7-9, wherein the control circuit is further configured to determine a subsegment count of noise pulses in each of a plurality of subsegments of the first cardiac signal segment, identify each subsegment of the plurality of subsegments that has a subsegment count of noise pulses that is greater than a second threshold value and determine the noise metric by determining a count of the identified subsegments having the subsegment count of noise pulses that is greater than the second threshold value. The control circuit may determine that the count of the identified subsegments is less than a third threshold value and determine that the noisy segment criteria are not met when the count of the identified subsegments is less than the third threshold value.

Example 11. The medical device of any of examples 1-10 wherein the sensing circuit is configured to sense ventricular event signals. The control circuit can be further configured to determine sensed event data from the at least one cardiac electrical signal in response to each of a plurality of ventricular event signals sensed by the sensing circuit and determine that suspected undersensing criteria are met based on the sensed event data. The control circuit may determine the amplitude metric from the first cardiac signal segment in response to the suspected undersensing criteria being met.

Example 12. The medical device of example 11 wherein the control circuit is further configured to determine the sensed event data by determining a ventricular sensed event interval from the ventricular event signals sensed by the sensing circuit, determine that the ventricular sensed event interval meets an undersensing threshold interval and determine that the suspected undersensing criteria are met in response to the ventricular sensed event interval meeting the undersensing threshold interval.

Example 13. The medical device of any of examples 11-12 wherein the control circuit is further configured to determine the sensed event data by determining a peak amplitude from the ventricular event signals sensed by the sensing circuit;

determine that the peak amplitude is less than an undersensing amplitude threshold; and determine that the suspected undersensing criteria are met in response to the peak amplitude being less than the undersensing threshold amplitude.

Example 14. The medical device of any of examples 11-13, wherein the control circuit is further configured to determine the sensed event data by determining a morphology matching score between each of the plurality of ventricular event signals sensed by the sensing circuit and an R-wave template, determine that a threshold number of the morphology matching scores are less than a match threshold and determine that the suspected undersensing criteria are met in response to the threshold number of the morphology matching scores being less than the match threshold.

Example 15. The medical device of any of examples 1-14 wherein the control circuit is further configured to perform the second analysis of the first cardiac signal segment for detecting the second arrhythmia by determining at least one of a low slope content from the first cardiac signal segment, a spectral width from the first cardiac signal segment; and a mean period from the first cardiac signal segment. The control circuit may determine that at least one of the low slope content, the spectral width and the mean period meet ventricular tachyarrhythmia segment criteria and detect the second arrhythmia by detecting ventricular tachyarrhythmia in response to the at least one of the low slope content, the spectral width and the mean period meeting the ventricular tachyarrhythmia segment criteria.

Example 16. The medical device of any of examples 1-15, wherein the control circuit is further configured to perform the second analysis of the first cardiac signal segment for detecting the second arrhythmia at least by determining a spectral width from the first cardiac signal segment, determining a mean period from the first cardiac signal segment, determining that the mean period meets a first threshold, determining that a ratio of the spectral width and the mean period meet a second threshold. The control circuit may detect the second arrhythmia by detecting ventricular tachyarrhythmia at least in response to the mean period meeting the first threshold and the ratio of the spectral width and the mean period meeting the second threshold.

Example 17. The medical device of any of examples 1-16 wherein the control circuit is further configured to perform the second analysis on a second cardiac signal segment of the at least one cardiac electrical signal sensed by the sensing circuit over a second time interval, determine that the first cardiac signal segment and the second signal segment are tachyarrhythmia signal segments based on the second analysis and detect the second arrhythmia by detecting ventricular tachyarrhythmia in response to the first cardiac signal segment and the second cardiac signal segment being tachyarrhythmia signal segments.

Example 18. The medical device of any of examples 1-17 wherein the control circuit is further configured to detect the first arrhythmia by detecting asystole based on the first analysis of the first cardiac signal segment.

Example 19. The medical device of any of examples 1-18 wherein the control circuit is further configured to perform the first analysis when the amplitude metric does not meet the amplitude threshold by determining a gradient signal from the first cardiac signal segment and determining that the gradient signal is within an asystole amplitude range for a detection time interval. The control circuit may detect the first arrhythmia based on at least the first analysis by detecting asystole at least in response to the gradient signal being within the asystole amplitude range for the detection time interval.

Example 20. The medical device of any of examples 1-19 wherein the therapy delivery circuit is further configured to deliver the first electrical stimulation therapy by delivering at least one pacing pulse in response to the control circuit detecting the first arrhythmia based on at least the first analysis.

Example 21. The medical device of any of examples 1-20, wherein the therapy delivery circuit is further configured to deliver the second electrical stimulation therapy by delivering a tachyarrhythmia therapy in response to the control circuit detecting the second arrhythmia based on at least the second analysis.

Example 22. A method including sensing at least one cardiac electrical signal, determining an amplitude metric from a first cardiac signal segment of the at least one cardiac electrical signal sensed over a first time interval, determining if the amplitude metric meets an amplitude threshold and performing one of: a first analysis of the first cardiac electrical signal segment for detecting a first arrhythmia in response to the amplitude metric not meeting the amplitude threshold or a second analysis of the first cardiac electrical signal segment for detecting a second arrhythmia different than the first arrhythmia in response to the amplitude metric meeting the amplitude threshold. The method may further include delivering one of a first electrical stimulation therapy in response to detecting the first arrhythmia based on at least the first analysis or a second electrical stimulation therapy different than the first electrical stimulation therapy in response to detecting the second arrhythmia based on at least the second analysis.

Example 23. The method of example 22 wherein determining the amplitude metric comprises identifying signal pulses from the first cardiac signal segment, determining a peak amplitude of each of the identified signal pulses and determining the amplitude metric based on the determined peak amplitudes.

Example 24. The method of example 23 wherein identifying the signal pulses from the first cardiac signal segment comprises identifying a plurality of subsegments of the first cardiac signal segment, determining a local maximum from each of the plurality of subsegments, determining a signal pulse amplitude threshold based on the local maximums and identifying the signal pulses from the first cardiac signal segment by identifying pulses having an amplitude greater than the signal pulse amplitude threshold.

Example 25. The method of any of examples 23-24 wherein identifying the signal pulses further comprises identifying pulses that are at least a minimum time interval apart.

Example 26. The method of any of examples 22-25, wherein performing the second analysis of the first cardiac signal segment for detecting the second arrhythmia comprises identifying signal pulse peaks from the first cardiac signal segment, determining peak intervals between the identified signal pulse peaks, determining a peak interval metric based on the determined peak intervals and determining if the peak interval metric meets a ventricular tachyarrhythmia threshold interval.

Example 27. The method of example 26 further comprising determining that the peak interval metric does not meet the ventricular tachyarrhythmia threshold interval and terminating the second analysis of the first cardiac signal segment for detecting the ventricular tachyarrhythmia when the peak interval metric does not meet the ventricular tachyarrhythmia threshold interval.

Example 28. The method of any of examples 22-27 wherein performing the second analysis of the first cardiac signal segment for detecting the second arrhythmia further comprises determining a noise metric from the first cardiac signal segment, determining that the noise metric does not meet noisy segment criteria and detecting the second arrhythmia based on the second analysis of the first cardiac signal segment at least in response to the noise metric not meeting the noisy segment criteria.

Example 29. The method of example 28 wherein determining the noise metric comprises determining at least one of a mean rectified amplitude of the first cardiac signal segment, a normalized mean rectified amplitude of the first cardiac signal segment or a mean period of the first cardiac signal segment.

Example 30. The method of any of examples 28-29, further comprising determining a subsegment count of noise pulses in each of a plurality of subsegments of the first cardiac signal segment, determining the noise metric by determining a maximum count of the subsegment counts of noise pulses and determining that the noisy segment criteria are not met when the maximum count is less than a first threshold value.

Example 31. The method of any of examples 28-30 further comprising determining a subsegment count of noise pulses in each of a plurality of subsegments of the first cardiac signal segment, identifying each subsegment of the plurality of subsegments that has a subsegment count of noise pulses that is greater than a second threshold value, determining the noise metric by determining a count of the identified subsegments having the subsegment count of noise pulses that is greater than the second threshold value and determining that the count of the identified subsegments is less than a third threshold value. The method may further include determining that the noisy segment criteria are not met when the count of the identified subsegments is less than the third threshold value.

Example 32. The method of any of examples 22-31 further comprising sensing ventricular event signals, determining sensed event data from the at least one cardiac electrical signal in response to each of a plurality of sensed ventricular event signals, determining that suspected undersensing criteria are met based on the sensed event data and determining the amplitude metric from the first cardiac signal segment in response to the suspected undersensing criteria being met.

Example 33. The method of example 32 further comprising determining the sensed event data by determining a ventricular sensed event interval from the sensed ventricular event signals, determining that the ventricular sensed event interval meets an undersensing threshold interval and determining that the suspected undersensing criteria are met in response to the ventricular sensed event interval meeting the undersensing threshold interval.

Example 34. The method of any of examples 32-33 further comprising determining the sensed event data by determining a peak amplitude from the sensed ventricular event signals, determining that the peak amplitude is less than an undersensing amplitude threshold and determining that the suspected undersensing criteria are met in response to the peak amplitude being less than the undersensing threshold amplitude.

Example 35. The method of any of examples 32-34 further comprising determining the sensed event data by determining a morphology matching score between each of the plurality of sensed ventricular event signals and an R-wave template, determining that a threshold number of the morphology matching scores are less than a match threshold; and determining that the suspected undersensing criteria are met in response to the threshold number of the morphology matching scores being less than the match threshold.

Example 36. The method of any of examples 22-35 wherein performing the second analysis of the first cardiac signal segment for detecting the second arrhythmia further comprises determining at least one of: a low slope content from the first cardiac signal segment, a spectral width from the first cardiac signal segment or a mean period from the first cardiac signal segment. The method may further include determining that at least one of the low slope content, the spectral width and the mean period meet ventricular tachyarrhythmia segment criteria and detecting the second arrhythmia by detecting ventricular tachyarrhythmia in response to the at least one of the low slope content, the spectral width and the mean period meeting the ventricular tachyarrhythmia segment criteria.

Example 37. The method of any of examples 22-36 wherein performing the second analysis of the first cardiac signal segment for detecting the second arrhythmia further comprises determining a spectral width from the first cardiac signal segment, determining a mean period from the first cardiac signal segment, determining that the mean period meets a first threshold, and determining a ratio of the spectral width and the mean period meet a second threshold. The method may further include detecting the second arrhythmia by detecting ventricular tachyarrhythmia at least in response to the mean period meeting the first threshold and the ratio of the spectral width and the mean period meeting the second threshold.

Example 38. The method of any of examples 22-37 further comprising performing the second analysis on a second cardiac signal segment of the at least one cardiac electrical signal sensed over a second predetermined time interval, determining that the first cardiac signal segment and the second cardiac signal segment are tachyarrhythmia signal segments based on the second analysis and detecting the second arrhythmia by detecting ventricular tachyarrhythmia in response to the first cardiac signal segment and the second cardiac signal segment being tachyarrhythmia signal segments.

Example 39. The method of any of examples 22-38 further comprising detecting the first arrhythmia by detecting asystole based on the first analysis of the first cardiac signal segment.

Example 40. The method of any of examples 22-39 further comprising performing the first analysis when the amplitude metric does not meet the amplitude threshold by determining a gradient signal from the first cardiac signal segment and determining that the gradient signal is within an asystole amplitude range for a detection time interval. The method may further include detecting the first arrhythmia based on the first analysis by detecting asystole in response to the gradient signal being within the asystole amplitude range for the detection time interval.

Example 41. The method of any of examples 22-40 further comprising delivering the first electrical stimulation therapy by delivering at least one pacing pulse in response to detecting the first arrhythmia based on at least the first analysis.

Example 42. The method of any of examples 22-41 further comprising delivering the second electrical stimulation therapy by delivering a tachyarrhythmia therapy in response to detecting the second arrhythmia based on at least the second analysis.

Example 43. A non-transitory, computer readable medium storing a set of instructions that, when executed by a control circuit of a medical device, cause the medical device to sense at least one cardiac electrical signal, determine an amplitude metric from a cardiac signal segment of the at least one cardiac electrical signal sensed over a time interval, determine if the amplitude metric meets an amplitude threshold and perform one of: a first analysis of the cardiac electrical signal segment for detecting a first arrhythmia in response to the amplitude metric not meeting the amplitude threshold; or a second analysis of the cardiac electrical signal segment for detecting a second arrhythmia different than the first arrhythmia in response to the amplitude metric meeting the amplitude threshold. The instructions may further cause the medical device to deliver a first electrical stimulation therapy in response to detecting the first arrhythmia based on at least the first analysis or deliver a second electrical stimulation therapy different than the first electrical stimulation therapy in response to detecting the second arrhythmia based on at least the second analysis.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:
1. A medical device comprising:
a sensing circuit configured to sense at least one cardiac electrical signal including a first cardiac electrical signal;
a memory configured to store an amplitude threshold and a tachyarrhythmia detection interval;
a control circuit in communication with the sensing circuit, the control circuit configured to:
buffer in the memory a cardiac electrical signal segment of the first cardiac electrical signal sensed by the sensing circuit, the cardiac signal segment extending over a time interval that is greater than the tachyarrhythmia detection interval;
determine an amplitude metric from a plurality of peak amplitudes of the cardiac signal segment sensed over the time interval;
determine if the amplitude metric meets the amplitude threshold; and
perform a first analysis of the cardiac electrical signal segment for detecting asystole in response to the amplitude metric not meeting the amplitude thresh- old and detect the asystole based on the first analysis of the cardiac signal segment; and
perform a second analysis of the cardiac electrical signal segment for detecting a ventricular tachyarrhythmia in response to the amplitude metric meeting the amplitude threshold and detect the ventricular tachyarrhythmia based on the second analysis of the cardiac signal segment; and
a therapy delivery circuit in communication with the control circuit, the therapy delivery circuit configured to deliver:
a first electrical stimulation therapy in response to the control circuit detecting the asystole based on at least the first analysis; or
a second electrical stimulation therapy different than the first electrical stimulation therapy in response to the control circuit detecting the ventricular tachyarrhythmia based on at least the second analysis.
2. The medical device of claim 1, wherein the control circuit is further configured to determine the amplitude metric by:
identifying signal pulses from the cardiac signal segment;
determining the plurality of peak amplitudes by determining a peak amplitude of each of the identified signal pulses; and
determining the amplitude metric by computing a representative value of the determined plurality of peak amplitudes.
3. The medical device of claim 2, wherein the control circuit is further configured to identify the signal pulses from the cardiac signal segment by:
identifying a plurality of subsegments of the cardiac signal segment;
determining a local maximum from each of the plurality of subsegments;
determining a signal pulse amplitude threshold based on the local maximums; and
identifying the signal pulses from the cardiac signal segment by identifying pulses having an amplitude greater than the signal pulse amplitude threshold.
4. The medical device of claim 2, wherein the control circuit is further configured to identify the signal pulses by identifying pulses that are at least a minimum time interval apart.
5. The medical device of claim 1, wherein the control circuit is further configured to perform the second analysis of the cardiac signal segment for detecting the ventricular tachyarrhythmia by:
identifying signal pulse peaks from the cardiac signal segment;
determining peak intervals between the identified signal pulse peaks;
determining a peak interval metric based on the determined peak intervals; and
determining if the peak interval metric meets a ventricular tachyarrhythmia threshold interval.
6. The medical device of claim 1, wherein the control circuit is further configured to perform the second analysis of the cardiac signal segment for detecting the ventricular tachyarrhythmia by:
determining a noise metric from the cardiac signal segment;
determining that the noise metric does not meet noisy segment criteria; and detecting the ventricular tachyarrhythmia based on the second analysis of the cardiac signal segment at least in response to the noise metric not meeting the noisy segment criteria.

7. The medical device of claim 1, wherein:

the sensing circuit is configured to sense ventricular event signals; and the control circuit is further configured to:

determine sensed event data from the at least one cardiac electrical signal in response to each of a plurality of ventricular event signals sensed by the sensing circuit;

determine that suspected undersensing criteria are met based on the sensed event data; and determine the amplitude metric from the cardiac signal segment in response to the suspected undersensing criteria being met.

8. The medical device of claim 7, wherein the control circuit is further configured to:

determine the sensed event data by determining a ventricular sensed event interval from the ventricular event signals sensed by the sensing circuit;

determine that the ventricular sensed event interval meets an undersensing threshold interval; and determine that the suspected undersensing criteria are met in response to the ventricular sensed event interval meeting the undersensing threshold interval.

9. The medical device of claim 7, wherein the control circuit is further configured to:

determine the sensed event data by determining a peak amplitude from the ventricular event signals sensed by the sensing circuit;

determine that the peak amplitude is less than an undersensing amplitude threshold; and determine that the suspected undersensing criteria are met in response to the peak amplitude being less than the undersensing threshold amplitude.

10. The medical device of claim 7, wherein the control circuit is further configured to:

determine the sensed event data by determining a morphology matching score between each of the plurality of ventricular event signals sensed by the sensing circuit and an R-wave template;

determine that a threshold number of the morphology matching scores are less than a match threshold; and determine that the suspected undersensing criteria are met in response to the threshold number of the morphology matching scores being less than the match threshold.

11. The medical device of claim 1, wherein the control circuit is further configured to perform the second analysis of the cardiac signal segment for detecting the ventricular tachyarrhythmia by:

determining at least one of:

a low slope content from the cardiac signal segment;

a spectral width from the cardiac signal segment; and a mean period from the cardiac signal segment;

determining that at least one of the low slope content, the spectral width and the mean period meet ventricular tachyarrhythmia segment criteria; and detecting the ventricular tachyarrhythmia at least in response to at least one of the low slope content, the spectral width and the mean period meeting the ventricular tachyarrhythmia segment criteria.

12. The medical device of claim 1, wherein the control circuit is further configured to perform the second analysis of the cardiac signal segment for detecting the ventricular tachyarrhythmia arrhythmia at least by:

determining a spectral width from the cardiac signal segment;

determining a mean period from the cardiac signal segment;

determining that the mean period meets a first threshold;

determining that a ratio of the spectral width and the mean period meets a second threshold; and detecting the ventricular tachyarrhythmia at least in response to the mean period meeting the first threshold and the ratio of the spectral width and the mean period meeting the second threshold.

13. The medical device of claim 1, wherein the control circuit is further configured to detect the asystole based on the first analysis of the cardiac signal segment by:

determining a gradient signal from the cardiac signal segment;

determining that the gradient signal is within an asystole amplitude range for a detection time interval; and detecting the asystole at least in response to the gradient signal being within the asystole amplitude range for the detection time interval.

14. The medical device of claim 1, wherein the therapy delivery circuit is further configured to:

deliver the first electrical stimulation therapy by delivering at least one pacing pulse; and deliver the second electrical stimulation therapy by delivering a tachyarrhythmia therapy.

15. A method comprising:

sensing at least one cardiac electrical signal including a first cardiac electrical signal;

storing an amplitude threshold and a tachyarrhythmia detection interval in a memory;

buffering in the memory a cardiac electrical signal segment of the first cardiac electrical signal, the cardiac signal segment extending over a time interval that is greater than the tachyarrhythmia detection interval;

determining an amplitude metric from a plurality of peak amplitudes of the cardiac signal segment sensed over the time interval;

determining if the amplitude metric meets the amplitude threshold; and performing a first analysis of the first cardiac electrical signal segment for detecting asystole in response to the amplitude metric not meeting the amplitude threshold and detecting the asystole based on the first analysis of the cardiac signal segment; and performing a second analysis of the first cardiac electrical signal segment for detecting a ventricular tachyarrhythmia in response to the amplitude metric meeting the amplitude threshold and detecting the ventricular tachyarrhythmia based on the second analysis of the cardiac signal segment; and delivering:

a first electrical stimulation therapy in response to detecting the asystole based on at least the first analysis; or a second electrical stimulation therapy different than the first electrical stimulation therapy in response to detecting the ventricular tachyarrhythmia based on at least the second analysis.

16. The method of claim 15, wherein determining the amplitude metric comprises:

identifying signal pulses from the cardiac signal segment;

determining the plurality of peak amplitudes by determining a peak amplitude of each of the identified signal pulses; and determining the amplitude metric by computing a representative value of the determined plurality of peak amplitudes.

17. The method of claim 16, wherein identifying the signal pulses from the cardiac signal segment comprises:
identifying a plurality of subsegments of the cardiac signal segment;
determining a local maximum from each of the plurality of subsegments;
determining a signal pulse amplitude threshold based on the local maximums; and
identifying the signal pulses from the cardiac signal segment by identifying pulses having an amplitude greater than the signal pulse amplitude threshold.

18. The method of claim 16, wherein identifying the signal pulses further comprises identifying pulses that are at least a minimum time interval apart.

19. The method of claim 15, wherein performing the second analysis of the cardiac signal segment for detecting the ventricular tachyarrhythmia comprises:
identifying signal pulse peaks from the cardiac signal segment;
determining peak intervals between the identified signal pulse peaks;
determining a peak interval metric based on the determined peak intervals; and
determining if the peak interval metric meets a ventricular tachyarrhythmia threshold interval.

20. The method of claim 15, wherein performing the second analysis of the cardiac signal segment for detecting the ventricular tachyarrhythmia further comprises:
determining a noise metric from the cardiac signal segment;
determining that the noise metric does not meet noisy segment criteria; and
detecting the ventricular tachyarrhythmia based on the second analysis of the cardiac signal segment at least in response to the noise metric not meeting the noisy segment criteria.

21. The method of claim 15, further comprising:
sensing ventricular event signals;
determining sensed event data from the at least one cardiac electrical signal in response to each of a plurality of sensed ventricular event signals;
determining that suspected undersensing criteria are met based on the sensed event data; and
determining the amplitude metric from the cardiac signal segment in response to the suspected undersensing criteria being met.

22. The method of claim 21, further comprising:
determining the sensed event data by determining a ventricular sensed event interval from the sensed ventricular event signals;
determining that the ventricular sensed event interval meets an undersensing threshold interval; and
determining that the suspected undersensing criteria are met in response to the ventricular sensed event interval meeting the undersensing threshold interval.

23. The method of claim 21, further comprising:
determining the sensed event data by determining a peak amplitude from the sensed ventricular event signals;
determining that the peak amplitude is less than an undersensing amplitude threshold; and
determining that the suspected undersensing criteria are met in response to the peak amplitude being less than the undersensing threshold amplitude.

24. The method of claim 21, further comprising:
determining the sensed event data by determining a morphology matching score between each of the plurality of sensed ventricular event signals and an R-wave template;
determining that a threshold number of the morphology matching scores are less than a match threshold; and
determining that the suspected undersensing criteria are met in response to the threshold number of the morphology matching scores being less than the match threshold.

25. The method of claim 15, wherein performing the second analysis of the cardiac signal segment for detecting the ventricular tachyarrhythmia further comprises:
determining at least one of:
a low slope content from the cardiac signal segment;
a spectral width from the cardiac signal segment;
a mean period from the cardiac signal segment;
determining that at least one of the low slope content, the spectral width and the mean period meet ventricular tachyarrhythmia segment criteria; and
detecting the ventricular tachyarrhythmia at least in response to the least one of the low slope content, the spectral width and the mean period meeting the ventricular tachyarrhythmia segment criteria.

26. The method of claim 15, wherein performing the second analysis of the cardiac signal segment for detecting the ventricular tachyarrhythmia arrhythmia further comprises:
determining a spectral width from the cardiac signal segment;
determining a mean period from the cardiac signal segment;
determining that the mean period meets a first threshold;
determining that a ratio of the spectral width and the mean period meet a second threshold; and
detecting the ventricular tachyarrhythmia at least in response to the mean period meeting the first threshold and the ratio of the spectral width and the mean period meeting the second threshold.

27. The method of claim 15, further comprising detecting the asystole based on the first analysis of the cardiac signal segment by:
determining a gradient signal from the cardiac signal segment;
determining that the gradient signal is within an asystole amplitude range for a detection time interval; and
detecting the asystole at least in response to the gradient signal being within the asystole amplitude range for the detection time interval.

28. The method of claim 15, further comprising:
delivering the first electrical stimulation therapy by delivering at least one pacing pulse; and
delivering the second electrical stimulation therapy by delivering a tachyarrhythmia therapy.

29. A non-transitory, computer readable medium storing a set of instructions that, when executed by a control circuit of a medical device, cause the medical device to:
sense at least one cardiac electrical signal including a first cardiac electrical signal;
buffer a cardiac electrical signal segment of the first cardiac electrical signal, the cardiac signal segment extending over a time interval that is greater than a tachyarrhythmia detection interval;
determine an amplitude metric from a plurality of peak amplitudes of the cardiac signal segment sensed over the time interval;

determine if the amplitude metric meets an amplitude threshold; and perform a first analysis of the cardiac electrical signal segment for detecting asystole in response to the amplitude metric not meeting the amplitude threshold and detect asystole based on the first analysis of the cardiac signal segment; and perform a second analysis of the cardiac electrical signal segment for detecting a ventricular tachyarrhythmia in response to the amplitude metric meeting the amplitude threshold and detecting the ventricular tachyarrhythmia based on the second analysis of the cardiac signal segment; and deliver:

a first electrical stimulation therapy in response to detecting the asystole based on at least the first analysis; or a second electrical stimulation therapy different than the first electrical stimulation therapy in response to detecting the ventricular tachyarrhythmia based on at least the second analysis.

30. The medical device of claim 13 wherein the control circuit is further configured to determine that the gradient signal is within the asystole amplitude range for a detection time interval by determining that a first threshold number of sample points of the gradient signal are within the asystole amplitude range during each of a second threshold number of consecutive time windows of the cardiac signal segment, wherein each of the consecutive time windows comprise a specified number of sample points of the gradient signal.

* * * * *